(12) United States Patent
Goehring et al.

(10) Patent No.: US 8,969,358 B2
(45) Date of Patent: Mar. 3, 2015

(54) BUPRENORPHINE ANALOGS

(71) Applicant: Purdue Pharma L.P., Stamford, CT (US)

(72) Inventors: Richard Goehring, Yardley, PA (US); Laykea Tafesse, Robbinsville, NJ (US); Jiangchao Yao, Princeton, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/206,295

(22) Filed: Mar. 12, 2014

(65) Prior Publication Data

US 2014/0275117 A1    Sep. 18, 2014

Related U.S. Application Data

(60) Provisional application No. 61/786,997, filed on Mar. 15, 2013.

(51) Int. Cl.
*A61K 31/497* (2006.01)
*C07D 489/12* (2006.01)

(52) U.S. Cl.
CPC .................................. *C07D 489/12* (2013.01)
USPC .......... 514/255.05; 514/279; 544/406; 546/39

(58) Field of Classification Search
USPC ................ 546/39; 514/279, 255.05; 544/406
See application file for complete search history.

(56) References Cited

U.S. PATENT DOCUMENTS

| | | | |
|---|---|---|---|
| 3,464,994 A | 9/1969 | Bentley | |
| 3,474,101 A | 10/1969 | Bentley | |
| 5,849,915 A | 12/1998 | Kim et al. | |
| 2014/0057931 A1 | 2/2014 | Kyle et al. | |
| 2014/0163058 A1 | 6/2014 | Youngman | |

FOREIGN PATENT DOCUMENTS

| | | |
|---|---|---|
| EP | 0418591 A2 | 3/1991 |
| EP | 0915094 A1 | 5/1999 |
| JP | 2009/196933 A | 9/2009 |
| WO | 2012/038813 A1 | 3/2012 |
| WO | WO-2013/084060 A1 | 6/2013 |

OTHER PUBLICATIONS

David Rennison et al.: "Cinnamoyl Derivatives of 7α-Aminomethyl-6,14-endo-ethanotetrahydrothebaine and 7α-Aminomethyl-6,14-endo-ethanotetrahydrooripavine and Related Opioid Ligands", Journal of Medicinal Chemistry, 2007, vol. 50, No. 21, pp. 5176-5782.
Humphrey A. Moynihan et al.: "Fumaroylamino-4,5-epoxymorphinans and Related Opioids with Irreversible μ Opioid Receptor Antagonist Effects", Journal of Medicinal Chemistry, 2012, vol. 55, No. 22, pp. 9868-9874.
I.Derrick et al.: "Cinnamoylamidoethyloripavines: Preliminary in-vivo evaluation of potential new affinity ligands for opioid receptors", Analgesia Elmsford, NewYork, 1995, 1:4-6, pp. 386-389.
Austrian Search Report mailed Jan. 30, 2014 in U.S. Appl. No. 61/786,997.

*Primary Examiner* — Kristin Vajda
(74) *Attorney, Agent, or Firm* — Weiying Yang; Alan L. Koller

(57) ABSTRACT

The present invention is directed to Buprenorphine Analog compounds of Formula I, II, III, IV or V and including various stereoisomers (such as Formula IA shown below), wherein $R^1$, $R^{3a}$, $R^{3b}$, $R^{16}$, $R^{15}$, G, Q, X, A and Z are as defined herein.

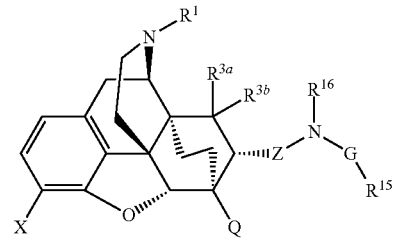

Formula IA

Compounds of the Invention may be useful for preparing medicaments useful for treating pain, constipation, and other conditions modulated by activity of opioid and ORL-1 receptors. Compounds of the Invention may be useful for treating Conditions such as pain, constipation, and others modulated by activity of opioid and ORL-1 receptors.

20 Claims, No Drawings

BUPRENORPHINE ANALOGS

CROSS REFERENCE TO RELATED APPLICATIONS

The application claims priority from U.S. provisional application Ser. No. 61/786,997, filed Mar. 15, 2013, now pending. The content of the afore-mentioned application is incorporated herein by its entirety.

BACKGROUND OF THE INVENTION

The invention is in the field of medicinal chemistry. It relates to novel buprenorphine analogs having activity as opioid receptor agonists and/or antagonists. In certain embodiments, compounds of the invention have activity at more than one opioid receptor.

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone or oxymorphone).

Although the term "narcotic" is often used to refer to opioids, the term is not specifically applicable to opioids. The term "narcotic", derived from the Greek word for "stupor", originally referred to any drug that induced sleep, only later being associated with opioids (Gutstein, Howard B., Akil, Huda, "Chapter 21. Opioid Analgesics" (Chapter 21), Brunton, L L, Lazo, J S, Parker, Kl: Goodman & Gilman's The Pharmacological Basis of Therapeutics, 11$^{th}$ Edition: http://www.accessmedicine.comicontentaspx?aID=940653). In the legal context, the term "narcotic" refers to a variety of mechanistically unrelated substances with abuse or addictive potential (Gutstein, Howard B., Akil, Huda, "Chapter 21. Opioid Analgesics" (Chapter 21), Brunton L L, Lazo J S, Parker Kl: Goodman & Gilman's The Pharmacological Basis of Therapeutics, 11$^{th}$ Edition: http://wwwaccessmedicine.com/contentaspx?aID=940653). Thus, the term "narcotic" not only refers to opioids, but also refers to such drugs as cocaine, methamphetamine, ecstasy, etc., which exert their pharmacological effects via different receptors than opioids. Furthermore, because the term "narcotic" refers to such a wide variety of unrelated drugs, many of which do not possess analgesic properties, it cannot be assumed that a drug that has "narcotic" properties is necessarily analgesic. For example, drugs such as ecstasy and methamphetamine are not analgesic, and are not used to treat pain.

Until recently, there was evidence of three major classes of opioid receptors in the central nervous system (CNS), with each class having subtype receptors. These receptor classes are known as $\mu$, $\delta$ and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL-1 receptor. This characteristic, along with the fact that an endogenous ligand had not yet been discovered, led to the ORL-1 receptor being designated as an "orphan receptor".

Subsequent research led to the isolation and structure of the endogenous ligand of the ORL-1 receptor. This ligand, nociceptin (also known as orphanin FQ (OFQ)), is a seventeen amino acid peptide structurally similar to members of the opioid peptide family. (C. Altier et al., "ORL-1 receptor-mediated internalization of N-type calcium channels." *Nature Neuroscience*, 2005, 9:31).

The discovery of the ORL-1 receptor and its endogenous ligand, presents an opportunity for the discovery of novel compounds that can be administered for pain management or other syndromes influenced by this receptor.

Many publications in the ORL-1/nociceptin field provide evidence that activation of ORL-1 receptors in the brain can inhibit opioid-mediated analgesia (e.g., D. Barlocco et al., "The opioid-receptor-like 1 (ORL-1) as a potential target for new analgesics." *Eur. J. Med. Chem.*, 2000, 35:275; J. S. Mogil et al., "Orphanin FQ is a functional anti-opioid peptide." *Neurosci.*, 1996, 75:333; K. Lutfy et al., "Tolerance develops to the inhibitory effect of orphanin FQ on morphine-induced antinociception in the rat." *NeuroReport*, 1999, 10:103; M. M. Morgan et al., "Antinociception mediated by the periaqueductal gray is attenuated by orphanin FQ." *NeuroReport*, 1997, 8:3431; and J. Tian et al., "Involvement of endogenous Orphanin FQ in electroacupuncture-induced analgesia." *NeuroReport*, 1997, 8:497).

A growing body of evidence supports a more generalized regulatory role for ORL-1 against the actions of the n receptor, possibly contributing to the development of n-agonist tolerance in patients being treated with classical opiates (e.g., J. Tian et al., "Functional studies using antibodies against orphanin FQ/nociceptin." *Peptides*, 2000, 21:1047; and H. Ueda et al., "Enhanced Spinal Nociceptin Receptor Expression Develops Morphine Tolerance and Dependence." *J. Neurosci.*, 2000, 20:7640). Moreover, ORL-1 activation appears to have an inhibitory effect on the rewarding properties of several drugs of abuse, including n agonists.

Certain compounds have been described as at least partial agonists for ORL-1 (e.g., buprenorphine ($IC_{50}$ of 8.4 nM), fentanyl ($IC_{50}$ of about 10,000 nM), 7-benzylidenenaltrexone ($IC_{50}$ about 10,000 nM) (S. Wnendt et al., "Agonistic effect of buprenorphine in a nociceptin/OFQ receptor-triggered reporter gene assay." *Molec. Pharmacol.*, 1999, 56:334-338), and etorphine ($IC_{50}$ of about 2000 nM) (Hawkinson et al., "Opioid activity profiles indicate similarities between the nociceptin/orphanin FQ and opioid receptors." *Eur. J. Pharmacol*, 2000, 389:107-114)). However, buprenorphine's potency is disclosed to be much greater than its ORL-1 potency.

Recent data have shown that the analgesic efficacy of buprenorphine is enhanced by pre-treatment with an ORL-1 receptor antagonist. Using the tail-flick test in mice, Lutfy et al. demonstrated that buprenorphine's typical bell-shaped dose-response curve (wherein low and high doses induce little analgesia, and mid-range doses produce maximal analgesia) is eliminated by pre-treatment with the ORL-1 antagonist J-113397, and analgesic efficacy is improved at the higher range of doses (K. Lutfy et al., "Buprenorphine-induced antinociception is mediated by n-opioid receptors and compromised by concomitant activation of opioid receptor-like receptors." *J. Neurosci.*, 2003, 23:10331-10337).

Recently, a multidisciplinary group of experts in the fields of pharmacology, toxicology, pain management, and anesthesia have recommended buprenorphine as the best opioid for treating chronic severe pain in elderly patients (Pergolizzi, et al. (2008). Opioids and the Management of Chronic Severe Pain in the Elderly: Consensus Statement of an International Expert Panel with Focus on the Six Clinically Most Often Used World Health Organization step IB Opioids (buprenorphine, Fentanyl, Hydromorphone, Methadone, Morphine, Oxycodone. *Pain Practice* 8(4): 287-313). It was found that of the opioids studied, buprenorphine provided the best analgesic-to-side effect profile. Buprenorphine was the most effective opioid for treating neuropathic pain. Buprenorphine was the only opioid for which metabolism was not affected by impaired renal function. Buprenorphine was the only opioid demonstrating a ceiling effect for respiratory depression, indicating that higher doses may be used. Also, buprenorphine was the least likely to induce immunosuppression. The panel of experts attributed the improved therapeutic efficacy of buprenorphine to its unique pharmacological profile.

Buprenorphine has also been shown to have an improved side effect profile in animal models. A review of recent data in animal models of reward and addiction has shown that buprenorphine has a low addictive and dependence-inducing profile compared to other opioids (Tzschentike (2002). Behavioral pharmacology of buprenorphine, with a focus on preclinical models of reward and addiction. *Psychopharmacology* 161: 1-16).

Use of opioid analgesics often leads to constipation as a side effect. Constipation associated with the use of opioid analgesics is presumed to occur primarily and mechanistically as a result of the action of μ opioid agonists directly upon μ opioid receptors located in the bowel (Wood & Galligan (2004), Function of opioids in the enteric nervous system. *Neurogastroenterology & Motility* 16(Suppl. 2): 17-28.). Stimulation of the μ opioid receptors in the bowel causes inhibition of normal gastrointestinal (GI) motility, leading to constipation. The effect of μ opioid agonism on μ opioid receptors in the bowel can be observed via the action of loperamide (Imodium™) in treating diarrhea. Loperamide is a potent μ opioid agonist that is administered orally, but which has little to no absorption into the blood stream. As a result, loperamide exerts its action locally upon the μ opioid receptors in the bowel, and this results in inhibition of GI motility, which treats diarrhea.

There has been recent interest in developing combinations of μ receptor agonists and antagonists having defined biodistribution properties that might serve to limit opioid-induced constipation. For example, the co-administration of an orally bio-available μ opioid receptor agonist (such as morphine, codeine, oxycodone or hydromorphone) together with a potent μ opioid receptor antagonist (such as N-methylnaloxone or N-methylnaltrexone) that is not orally bio-available may serve to prevent or reduce the constipation otherwise associated with μ opioid receptor agonist therapy. The rationale is that the agonist component will be absorbed and distributed throughout the periphery and the central nervous system (CNS), resulting in the desired analgesia, while the antagonist component will remain in the bowel where it will prevent or reduce any agonist-induced constipation that might otherwise occur.

BRIEF SUMMARY OF THE INVENTION

The present invention provides novel buprenorphine analog compounds useful for treating a variety of conditions, including pain, in particular chronic pain, and constipation.

More specifically, the present invention provides compounds of Formula I, Formula IA, Formula IB, Formula II, or Formula III below, and the pharmaceutically acceptable salts and solvates thereof, that exhibit affinity for one or more of the ORL-1, μ, δ, and/or κ opioid receptors. Such compounds, salts, and solvates are collectively referred to hereinafter as "Compounds of the Invention" (each is individually referred to hereinafter as a "Compound of the Invention").

The present invention provides compounds of Formula I or Formula IA:

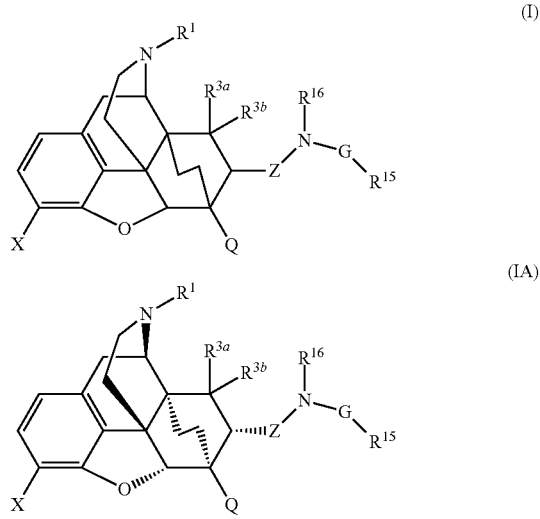

wherein

G is selected from carbonyl C(=O), sulfonyl S(=O)$_2$, or sulfinyl S(=O);

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$), —OH, —O(C=O)R$^9$, —O—(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl-C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ or R$^{14}$; any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from OH, hydroxy(C$_1$-C$_6$)alkyl-, dihydroxy (C$_1$-C$_6$)alkyl-, halogen, —NH$_2$, —NR$^{20}$(C=O)R$^{12}$, —CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O (C$_1$-C$_6$)alkyl, —(OCH$_2$CH$_2$), —OH, —(CH$_2$)$_p$CHOHCH$_2$OH, CN, —NH—SO$_2$R$^9$, —(C$_3$-C$_{12}$) cycloalkyl, ((C$_3$-C$_{12}$)cycloalkyl)-(C$_1$-C$_6$)alkyl-, ((C$_3$-C$_{12}$) cycloalkyl)-(C$_1$-C$_6$)alkoxy-, -(5- to 12-membered)aryl, ((5- to 12-membered)aryl)-(C$_1$-C$_6$)alkyl-, ((5- to 12-membered) aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, or ((7- to 12-membered)bicycloheterocycle)-($C_1$-$C_6$)alkoxy-; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

Z is —(CH$_2$)$_m$—, optionally substituted with 1 or 2-($C_1$-$C_6$)alkyl;

m is an integer 1, 2, 3, 4, 5, or 6;

p is an integer 0, 1 or 2;

s is an integer 1, 2, 3, 4, 5, 6, 7, 8, 9, 10, 11, 12, or 13;

R$^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

R$^{3a}$ and R$^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$)alkoxy-($C_1$-$C_6$)alkyl-, or together form (=O);

R$^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, or ((7- to 12-membered)bicycloheterocycle)-($C_1$-$C_6$)alkyl-;

R$^5$ and R$^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or R$^5$ and R$^6$ together with the nitrogen atom to which they are attached form a (4- to 8-membered)heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

R$^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, or (($C_4$-$C_{12}$)cycloalkenyl)-($C_1$-$C_6$)alkyl-;

R$^9$ and R$^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-;

each R$^{11}$ is independently selected from hydrogen, —($C_1$-$C_{10}$)alkyl, (($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

R$^{12}$ and R$^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —(C$_1$-C$_6$)alkyl-CO—OR$^7$, —C(=O)—(C$_1$-C$_6$)alkyl-COOR$^7$, —(C$_1$-C$_6$)alkyl-C(=O)—(C$_1$-C$_6$)alkyl-COOR$^7$, —CONH$_2$, or (C$_1$-C$_6$)alkyl-CONH—;

$R^{15}$ is selected from $R^{20}$ or $R^{21}$;

$R^{16}$ is selected from hydrogen, —(C$_1$-C$_6$)alkyl, —(C$_2$-C$_6$)alkenyl, —(C$_2$-C$_6$)alkynyl, —(C$_1$-C$_{10}$)alkoxy, —C(=O)—(C$_1$-C$_6$)alkyl, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, ((C$_3$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, or ((3- to 12-membered)heterocycle)-(C$_1$-C$_6$)alkyl; any of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^{20}$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—(C$_1$-C$_6$)alkyl, —(CH$_2$CH$_2$O)$_s$—(C$_1$-C$_6$)alkyl, —NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —CN, —SH, —OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

$R^{21}$ is selected from $R^{20}$ or an alpha-amino compound of structure:

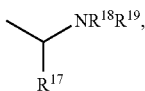

wherein each $R^{17}$ is independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkyl-CN, —(C$_1$-C$_6$)alkyl-CONR$^9$R$^{10}$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, ((3- to 12 membered)heterocycle)-(C$_1$-C$_6$)alkoxy-(C$_1$-C$_6$)alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and $R^{18}$ and $R^{19}$ are each independently selected from hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, ((C$_3$-C$_{12}$)cycloalkenyl)-(C$_1$-C$_6$)alkyl-, —C(=O)—(C$_1$-C$_6$)alkyl; any of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or $R^{19}$ may optionally be a peptide-forming moiety having the structure

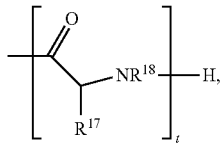

where t is an integer 1, 2 or 3;

provided that when $R^1$ is cyclopropylmethyl, G is C=O, Q and X are both —$OCH_3$, Z is —$CH_2$—, $R^{15}$ is —$C(NH_2)CH_3$, and $R^{16}$ is hydrogen, then either:

a) at least one of $R^{3a}$ and $R^{3b}$ is a substituent other than hydrogen; or b) at least one of $R^{18}$ and $R^{19}$ is a substituent other than hydrogen;

and further provided that when $R^1$ is cyclopropylmethyl, G is S(=O)$_2$, X and Q are both —$OCH_3$, Z is —$CH_2$—, $R^{15}$ is —$CH_3$, and $R^{16}$ is benzyl, then at least one of $R^{3a}$ and $R^{3b}$ is a substituent other than hydrogen;

or a pharmaceutically acceptable salt or solvate thereof.

The present invention further provides compounds of Formula IB:

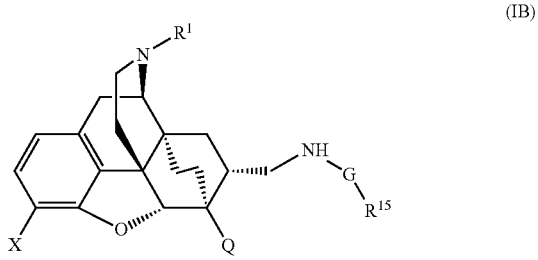

wherein

G is selected from carbonyl C(=O), sulfonyl S(=O)$_2$, or sulfinyl S(=O);

Q is selected from OH, ($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ or R$^{14}$; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from OH, hydroxy($C_1$-$C_6$)alkyl-, dihydroxy($C_1$-$C_6$)alkyl-, halogen, —NH$_2$, —NR$^{20}$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN, —NH—SO$_2$R$^5$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, or ((7- to 12-membered)bicycloheterocycle)-($C_1$-$C_6$)alkoxy-; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

p is an integer 0, 1 or 2;

s is an integer 1, 2, 3, 4, 5, 6, 7, 8, 9, 10, 11, 12, or 13;

$R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, or ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^7$ is selected from hydrogen, —$(C_1$-$C_6)$alkyl, —$(C_2$-$C_6)$alkenyl, —$(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, or $((C_4$-$C_{12})$cycloalkenyl)-$(C_1$-$C_6)$alkyl-;

$R^9$ and $R^{10}$ are each independently selected from hydrogen, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_3$-$C_{12})$cycloalkenyl, $((C_3$-$C_{12})$cycloalkyl)-$(C_1$-$C_6)$alkyl-, $((C_3$-$C_{12})$cycloalkenyl)-$(C_1$-$C_6)$alkyl-;

each $R^{11}$ is independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, $((C_1$-$C_6)$alkyl)sulfonyl$(C_1$-$C_6)$alkyl-, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, or $((C_4$-$C_{12})$cycloalkenyl)-$(C_1$-$C_6)$alkyl-;

$R^{12}$ and $R^{13}$ are each independently selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(OCH_2CH_2)_s$—$O(C_1$-$C_6)$alkyl, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, phenyl, benzyl, NH$_2$, —NH$(C_1$-$C_6)$alkyl, CN, SH, OR$^4$, —CONR$^5$R$^6$, —COOR$^7$, —$(C_3$-$C_{12})$cycloalkyl, $((C_3$-$C_{12})$cycloalkyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{14}$ is selected from —COOR$^7$, —$(C_1$-$C_6)$alkyl-CO—OR$^7$, —C(=O)—$(C_1$-$C_6)$alkyl-COOR$^7$, —$(C_1$-$C_6)$alkyl-C(=O)—$(C_1$-$C_6)$alkyl-COOR$^7$, —CONH$_2$, or $(C_1$-$C_6)$alkyl-CONH—;

$R^{15}$ is selected from $R^{20}$ or $R^{21}$;

$R^{20}$ is selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(OCH_2CH_2)_s$—$O(C_1$-$C_6)$alkyl, —$(CH_2CH_2O)_s$—$(C_1$-$C_6)$alkyl, —NH$_2$, —NH$(C_1$-$C_6)$alkyl, CN, —CONR$^5$R$^6$, —$(C_1$-$C_6)$alkyl-CO—NR$^5$R$^6$, —COOR$^7$, —$(C_1$-$C_6)$alkyl-CO—OR$^7$, —$(C_1$-$C_6)$alkoxy-COOR$^7$, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of —OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$alkyl-, —$(C_1$-$C_6)$alkoxy, $((C_1$-$C_6)$alkoxy)CO$(C_1$-$C_6)$alkoxy-, phenyl, benzyl, —NH$_2$, —NH$(C_1$-$C_6)$alkyl, —$(C_1$-$C_6)$alkyl-NH$(C_1$-$C_6)$alkyl-R$^{14}$, —CN, —SH, —OR$^4$, —CONR$^5$R$^6$, —$(C_1$-$C_6$alkyl)-CO—NR$^5$R$^6$, —COOR$^7$, —$(C_1$-$C_6)$alkyl-CO—OR$^7$, —$(C_1$-$C_6)$alkoxy-COOR$^7$, —$(OCH_2CH_2)_s$—$O(C_1$-$C_6)$alkyl, —$(CH_2CH_2O)_s$—$(C_1$-$C_6)$alkyl, $((C_1$-$C_6)$alkyl)sulfonyl$(C_1$-$C_6)$alkyl-, —NH—SO$_2$$(C_1$-$C_6)$alkyl, —N$(SO_2$$(C_1$-$C_6)$alkyl)$_2$, —C(=NH)NH$_2$, —NH—CO—$(C_1$-$C_6)$alkyl, —NH—CO—NH$_2$, —NH—C(=O)—NH—$(C_1$-$C_6)$alkyl, —NH—C(=O)-(5- to 12-membered)aryl, —NH—C(=O)—$(C_1$-$C_6)$alkyl-(5- to 12-membered)aryl, —NH—$(C_1$-$C_6)$alkyl-CO—OR$^7$, —NH—C(=O)—$(C_1$-$C_6)$alkyl-CO—OR$^7$, —NH—C(=O)—CH(NH$_2$)—$(C_1$-$C_6)$alkyl-CO—OR$^7$, —$(C_3$-$C_{12})$cycloalkyl, $((C_3$-$C_{12})$cycloalkyl)-$(C_1$-$C_6)$alkyl-, -(5- to 12-membered)aryl, -(5- to 12-membered)aryloxy, —$(C_1$-$C_6)$alkoxyC(O)NR$^5$R$^6$, —NH—$(C_1$-$C_6)$alkylC(O)—NR$^5$R$^6$, —C(O)NH—$(C_1$-$C_6)$alkyl-COOR$^7$, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{21}$ is selected from $R^{20}$ or an alpha-amino compound of structure:

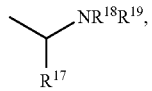

wherein each $R^{17}$ is independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, OH, hydroxy$(C_1$-$C_6)$alkyl-, —C(halo)$_3$, —CH(halo)$_2$, —CH$_2$(halo), —$(C_1$-$C_6)$alkyl-C(=O)—$(C_1$-$C_6)$alkoxy, —$(C_1$-$C_6)$alkoxy-C(=O)—$(C_1$-$C_6)$alkyl, —$(C_1$-$C_6)$alkyl-CN, —$(C_1$-$C_6)$alkyl-COOR$^7$, —$(C_1$-$C_6)$alkyl-CN, —$(C_1$-$C_6)$alkyl-CONR$^9$R$^{10}$, —$(C_1$-$C_6)$alkoxy-COOR$^7$, —$(C_3$-$C_{12})$cycloalkyl, $((C_3$-$C_{12})$cycloalkyl)-$(C_1$-$C_6)$alkyl-, $((C_3$-$C_{12})$cycloalkyl)-$(C_1$-$C_6)$alkoxy-, $((C_3$-$C_{12})$cycloalkyl)-$(C_1$-$C_6)$alkoxy-$(C_1$-$C_6)$alkyl-, —$(C_4$-$C_{12})$cycloalkenyl, $((C_4$-$C_{12})$cycloalkenyl)-$(C_1$-$C_6)$alkyl-, $((C_4$-$C_{12})$cycloalkenyl)-$(C_1$-$C_6)$alkoxy-, $((C_4$-$C_{12})$cycloalkenyl)-$(C_1$-$C_6)$alkoxy-$(C_1$-$C_6)$alkyl-, -(5- to 12-membered)aryl, ((5- to 12-membered)aryl)-$(C_1$-$C_6)$alkyl-, ((5- to 12-membered)aryl)-$(C_1$-$C_6)$alkoxy-, ((5- to 12-membered)aryl)-$(C_1$-$C_6)$alkoxy-$(C_1$-$C_6)$alkyl-, -(5- to 12-membered)heteroaryl, ((5- to 12-membered)heteroaryl)-$(C_1$-$C_6)$alkyl-, ((5- to 12-membered)heteroaryl)-$(C_1$-$C_6)$alkoxy-, ((5- to 12-membered)heteroaryl)-$(C_1$-$C_6)$alkoxy-$(C_1$-$C_6)$alkyl-, -(3- to 12-membered)heterocycle, ((3- to 12 membered)heterocycle)-$(C_1$-$C_6)$alkyl-, ((3- to 12 membered)heterocycle)-$(C_1$-$C_6)$alkoxy-, ((3- to 12 membered)heterocycle)-$(C_1$-$C_6)$alkoxy-$(C_1$-$C_6)$ alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and $R^{18}$ and $R^{19}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, —C(=O)—($C_1$-$C_6$)alkyl; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or $R^{19}$ may optionally be a peptide-forming moiety having the structure

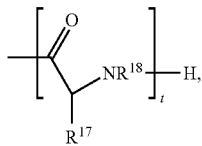

where t is an integer 1, 2 or 3;

provided that when $R^1$ is cyclopropylmethyl, G is C=O, and Q and X are both —OCH$_3$, then either:
a) $R^{15}$ is a substituent other than —C(NH$_2$)CH$_3$ or
b) at least one of $R^{18}$ and $R^{19}$ is a substituent other than hydrogen.
or a pharmaceutically acceptable salt or solvate thereof.

In another embodiment, the present invention provides compounds of Formula II:

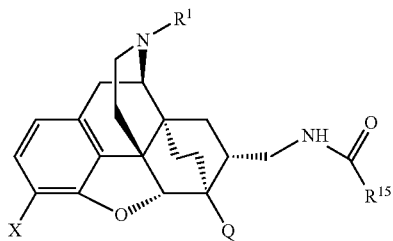

(II)

wherein

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ or R$^{14}$; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from OH, hydroxy($C_1$-$C_6$)alkyl-, dihydroxy($C_1$-$C_6$)alkyl-, halogen, —NH$_2$, —NR$^{20}$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$), —OH, —(CH$_2$)$_p$CHOHCH$_2$OH, CN, —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, or ((7- to 12-membered)bicycloheterocycle)-($C_1$-$C_6$)alkoxy-; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

p is an integer 0, 1 or 2;

s is an integer 1, 2, 3, 4, 5, 6, 7, 8, 9, 10, 11, 12, or 13;

$R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, or ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, or (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-;

each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_6$-$C_{14}$)bicycloalkyl, (($C_6$-$C_{14}$)bicycloalkyl)-($C_1$-$C_6$)alkyl-, (($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered) bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), ($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, or ($C_1$-$C_6$)alkyl-CONH—;

$R^{15}$ is selected from $R^{20}$ or $R^{21}$;

$R^{20}$ is selected from hydrogen, —($C_1$-$C_{10}$)alkyl, —($C_2$-$C_{12}$)alkenyl, (($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$($C_1$-$C_6$)alkyl, —NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, ($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, ($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —NH$_2$, —NH($C_1$-$C_6$)alkyl, —($C_1$-$C_6$)alkyl-NH ($C_1$-$C_6$)alkyl-R$^{14}$, —CN, —SH, —OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O ($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{21}$ is selected from $R^{20}$ or an alpha-amino compound of structure:

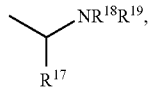

wherein each $R^{17}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkyl-CN, —($C_1$-$C_6$)alkyl-CONR$^9$R$^{10}$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-

$(C_1-C_6)$alkoxy-$(C_1-C_6)$alkyl-, —$(C_4-C_{12})$cycloalkenyl, $((C_4-C_{12})$cycloalkenyl$)$-$(C_1-C_6)$alkyl-, $((C_4-C_{12})$cycloalkenyl$)$-$(C_1-C_6)$alkoxy-, $((C_4-C_{12})$cycloalkenyl$)$-$(C_1-C_6)$alkoxy-$(C_1-C_6)$alkyl-, -(5- to 12-membered)aryl, ((5- to 12-membered)aryl)-$(C_1-C_6)$alkyl-, ((5- to 12-membered)aryl)-$(C_1-C_6)$alkoxy-, ((5- to 12-membered)aryl)-$(C_1-C_6)$alkoxy-$(C_1-C_6)$alkyl-, -(5- to 12-membered)heteroaryl, ((5- to 12-membered)heteroaryl)-$(C_1-C_6)$alkyl-, ((5- to 12-membered)heteroaryl)-$(C_1-C_6)$alkoxy-, ((5- to 12-membered)heteroaryl)-$(C_1-C_6)$alkoxy-$(C_1-C_6)$alkyl-, -(3- to 12-membered)heterocycle, ((3- to 12 membered)heterocycle)-$(C_1-C_6)$alkyl-, ((3- to 12 membered)heterocycle)-$(C_1-C_6)$alkoxy-, ((3- to 12 membered)heterocycle)-$(C_1-C_6)$alkoxy-$(C_1-C_6)$alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —$(C_1-C_6)$alkyl, OH, halo, —C(halo)$_3$, —CH(halo)$_2$, —CH$_2$(halo), —$(C_1-C_6)$alkyl-COOR$^7$, —COOR$^7$, NH$_2$, —NH$(C_1-C_6)$alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and $R^{18}$ and $R^{19}$ are each independently selected from hydrogen, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_3-C_{12})$cycloalkenyl, $((C_3-C_{12})$cycloalkyl$)$-$(C_1-C_6)$alkyl-, $((C_3-C_{12})$cycloalkenyl$)$-$(C_1-C_6)$alkyl-, —C(=O)—$(C_1-C_6)$alkyl; any of which is optionally substituted with 1 or 2 substituents independently selected from the group consisting of —$(C_1-C_6)$alkyl, OH, halo, —C(halo)$_3$, —CH(halo)$_2$, —CH$_2$(halo), —$(C_1-C_6)$alkyl-COOR$^7$, —COOR$^7$, NH$_2$, —NH$(C_1-C_6)$alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or $R^{19}$ may optionally be a peptide-forming moiety having the structure

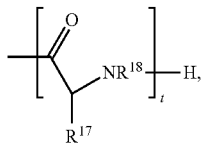

where t is an integer 1, 2 or 3;

provided that when $R^1$ is cyclopropylmethyl, G is C=O, and Q and X are both —OCH$_3$, then either:

a) $R^{15}$ is a substituent other than —C(NH$_2$)CH$_3$ or b) at least one of $R^{18}$ and $R^{19}$ is a substituent other than hydrogen.

or a pharmaceutically acceptable salt or solvate thereof.

In another embodiment, the present invention provides compounds of Formula III:

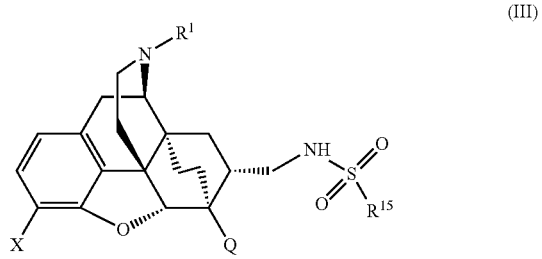

(III)

wherein

Q is selected from OH, —$(C_1-C_{10})$alkoxy, —$(C_1-C_{10})$alkyl, —$(C_3-C_{12})$cycloalkyl, -(5- to 12-membered)aryl, $((C_3-C_{12})$cycloalkyl$)$-$(C_1-C_6)$alkyl-, ((5- to 12-membered)aryl)-$(C_1-C_6)$alkyl-, —(OCH$_2$CH$_2$)$_s$—O$(C_1-C_6)$alkyl, —(CH$_2$CH$_2$O)$_s$—$(C_1-C_6)$alkyl, —(OCH$_2$CH$_2$)$_s$—OH, —O(C=O)R$^9$, —O—$(C_1-C_6)$alkyl-COOR$^7$, —NH—$(C_1-C_6)$alkyl-COOR$^7$, —O—C(O)—$(C_1-C_6)$alkyl-C(O)OR$^7$, —NH—C(O)—$(C_1-C_6)$alkyl-C(O)OR$^7$, —O—$(C_1-C_6)$alkyl-C(O)NR$^9$R$^{10}$, —NH—$(C_1-C_6)$alkyl-C(O)NR$^9$R$^{10}$, —O—C(O)—$(C_1-C_6)$alkyl-C(O)NR$^9$R$^{10}$, —NH—C(O)—$(C_1-C_6)$alkyl-C(O)NR$^9$R$^{10}$ or $R^{14}$; any of which may optionally be substituted with 1, 2, or 3 substituents independently selected from the group consisting of —$(C_1-C_6)$alkyl, OH, halo, —C(halo)$_3$, —CH(halo)$_2$, —CH$_2$(halo), —$(C_1-C_6)$alkyl-COOR$^7$, —COOR$^7$, NH$_2$, —NH$(C_1-C_6)$alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from OH, hydroxy$(C_1-C_6)$alkyl-, dihydroxy$(C_1-C_6)$alkyl-, halogen, —NH$_2$, —NR$^{20}$(C=O)R$^{12}$, —CONR$^{12}$R$^{13}$, —$(C_1-C_6)$alkyl-CONH$_2$, —$(C_1-C_6)$alkyl-COOH, —COOH, —O—$(C_1-C_6)$alkyl-COOH, —O—$(C_1-C_6)$alkyl-CONH$_2$, —$(C_1-C_{10})$alkyl, —$(C_2-C_{10})$alkenyl, —$(C_2-C_{10})$alkynyl, —$(C_1-C_{10})$alkoxy, —(OCH$_2$CH$_2$)$_s$—O$(C_1-C_6)$alkyl, —(OCH$_2$CH$_2$)$_s$—OH, —(CH$_2$)$_p$CHOHCH$_2$OH, CN, —NH—SO$_2$R$^9$, —$(C_3-C_{12})$cycloalkyl, $((C_3-C_{12})$cycloalkyl$)$-$(C_1-C_6)$alkyl-, $((C_3-C_{12})$cycloalkyl$)$-$(C_1-C_6)$alkoxy-, -(5- to 12-membered)aryl, ((5- to 12-membered)aryl)-$(C_1-C_6)$alkyl-, ((5- to 12-membered)aryl)-$(C_1-C_6)$alkoxy-, -(5- to 12-membered)heteroaryl, ((5- to 12-membered)heteroaryl)-$(C_1-C_6)$alkyl-, ((5- to 12-membered)heteroaryl)-$(C_1-C_6)$alkoxy-, -(3- to 12-membered)heterocycle, ((3- to 12-membered)heterocycle)-$(C_1-C_6)$alkyl-, ((3- to 12-membered)heterocycle)-$(C_1-C_6)$alkoxy-, -(7- to 12-membered)bicycloheterocycle, ((7- to 12-membered)bicycloheterocycle)-$(C_1-C_6)$alkyl-, or ((7- to 12-membered)bicycloheterocycle)-$(C_1-C_6)$alkoxy-; any of which may optionally be substituted with 1, 2, or 3 substituents independently selected from the group consisting of —$(C_1-C_6)$alkyl, OH, halo, —C(halo)$_3$, —CH(halo)$_2$, —CH$_2$(halo), —$(C_1-C_6)$alkyl-COOR$^7$, —COOR$^7$, NH$_2$, —NH$(C_1-C_6)$alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

p is an integer 0, 1 or 2;

s is an integer 1, 2, 3, 4, 5, 6, 7, 8, 9, 10, 11, 12, or 13;

$R^1$ is selected from hydrogen, —$(C_1-C_{10})$alkyl, —$(C_2-C_{12})$alkenyl, —$(C_2-C_{12})$alkynyl, —$(C_1-C_{10})$alkoxy, —$(C_3-C_{12})$cycloalkyl, —$(C_4-C_{12})$cycloalkenyl, $((C_3-C_{12})$cycloalkyl$)$-$(C_1-C_6)$alkyl-, $((C_4-C_{12})$cycloalkenyl$)$-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, phenyl, and benzyl; any of which is optionally substituted with 1, 2, or 3 substituents independently selected from the group consisting of —$(C_1-C_6)$alkyl, OH, halo, —C(halo)$_3$, —CH(halo)$_2$, —CH$_2$(halo), —$(C_1-C_6)$alkyl-COOR$^7$, —COOR$^7$, NH$_2$, —NH$(C_1-C_6)$alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^4$ is selected from —$(C_1-C_6)$alkyl, —$(C_2-C_6)$alkenyl, —$(C_2-C_6)$alkynyl, —C(halo)$_3$, —CH(halo)$_2$, —CH$_2$(halo), hydroxy$(C_1-C_6)$alkyl-, —$(C_3-C_{12})$cycloalkyl, $((C_3-C_{12})$cycloalkyl$)$-$(C_1-C_6)$alkyl-, —$(C_6-C_{14})$bicycloalkyl, $((C_6-C_{14})$ bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, or ((7- to 12-membered)bicycloheterocycle)-$(C_1$-$C_6)$alkyl-;

$R^5$ and $R^6$ are each independently hydrogen, —$(C_1$-$C_6)$ alkyl, —$(C_3$-$C_8)$cycloalkyl, $((C_3$-$C_8)$cycloalkyl)-$(C_1$-$C_6)$ alkyl-, —$COOR^7$, —$(C_1$-$C_6)$alkyl-CO—$OR^7$, —$CONH_2$, or $(C_1$-$C_6)$alkyl-CONH—, or $R^5$ and $R^6$ together with the nitrogen atom to which they are attached form a (4- to 8-membered)heterocycle; any of which is optionally substituted with 1 or 2 substituents independently selected from the group consisting of —$(C_1$-$C_6)$alkyl, OH, halo, —$C(halo)_3$, —$CH(halo)_2$, —$CH_2(halo)$, —$(C_1$-$C_6)$alkyl-$COOR^7$, —$COOR^7$, $NH_2$, —$NH(C_1$-$C_6)$alkyl, —$NR^9R^{10}$, —CN, —$OR^4$, —$CONR^9R^{10}$, —$NR^9COR^{10}$, —$SR^{11}$, -(3- to 12-membered)carbocyclic ring, -(5- to 12-membered)heterocycle, phenyl, and benzyl;

$R^7$ is selected from hydrogen, —$(C_1$-$C_6)$alkyl, —$(C_2$-$C_6)$ alkenyl, —$(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, or $((C_4$-$C_{12})$cycloalkenyl)-$(C_1$-$C_6)$alkyl-;

$R^9$ and $R^{10}$ are each independently selected from hydrogen, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_3$-$C_{12})$cycloalkenyl, $((C_3$-$C_{12})$cycloalkyl)-$(C_1$-$C_6)$alkyl-, $((C_3$-$C_{12})$cycloalkenyl)-$(C_1$-$C_6)$alkyl-;

each $R^{11}$ independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, $((C_1$-$C_6)$alkyl)sulfonyl$(C_1$-$C_6)$alkyl-, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, or $((C_4$-$C_{12})$cycloalkenyl)-$(C_1$-$C_6)$alkyl-;

$R^{12}$ and $R^{13}$ are each independently selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(OCH_2CH_2)_s$—$O(C_1$-$C_6)$alkyl, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$ alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)$(C_1$-$C_6)$alkyl-, -(7- to 12-membered)bicyclic ring system, ((7- to 12-membered) bicyclic ring system)-$(C_1$-$C_6)$alkyl-, -(7- to 12-membered) bicyclic aryl, ((7- to 12-membered)bicyclic aryl)-$(C_1$-$C_6)$ alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of OH, (═O), halo, —$C(halo)_3$, —CH$(halo)_2$, —$CH_2(halo)$, —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, phenyl, benzyl, $NH_2$, —$NH(C_1$-$C_6)$alkyl, CN, SH, $OR^4$, —$CONR^5R^6$, —$COOR^7$, —$(C_3$-$C_{12})$cycloalkyl, $((C_3$-$C_{12})$ cycloalkyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{14}$ is selected from —$COOR^7$, —$(C_1$-$C_6)$alkyl-CO—$OR^7$, —$C(═O)$—$(C_1$-$C_6)$alkyl-$COOR^7$, —$(C_1$-$C_6)$alkyl-C$(═O)$—$(C_1$-$C_6)$alkyl-$COOR^7$, —$CONH_2$, or $(C_1$-$C_6)$alkyl-CONH—;

$R^{15}$ is selected from $R^{20}$;

$R^{20}$ is selected from hydrogen, —$(C_1$-$C_{10})$alkyl, —$(C_2$-$C_{12})$alkenyl, $((C_2$-$C_{12})$alkynyl, —$(C_1$-$C_{10})$alkoxy, —$(OCH_2CH_2)_s$—$O(C_1$-$C_6)$alkyl, —$(CH_2CH_2O)_s(C_1$-$C_6)$ alkyl, —$NH_2$, —$NH(C_1$-$C_6)$alkyl, CN, —$CONR^5R^6$, —$(C_1$-$C_6)$alkyl-CO—$NR^5R^6$, —$COOR^7$, $((C_1$-$C_6)$alkyl-CO—$OR^7$, —$(C_1$-$C_6)$alkoxy-$COOR^7$, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, $((C_6$-$C_{14})$bicycloalkyl, $((C_6$-$C_{14})$bicycloalkyl)-$(C_1$-$C_6)$alkyl-, —$(C_8$-$C_{20})$ tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$ alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of —OH, (═O), halo, —$C(halo)_3$, —$CH(halo)_2$, —$CH_2(halo)$, —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$ alkyl-, —$(C_1$-$C_6)$alkoxy, $((C_1$-$C_6)$alkoxy)$CO(C_1$-$C_6)$ alkoxy-, phenyl, benzyl, —$NH_2$, —$NH(C_1$-$C_6)$alkyl, —$(C_1$-$C_6)$alkyl-$NH(C_1$-$C_6)$alkyl-$R^{14}$, —CN, —SH, —$OR^4$, —$CONR^5R^6$, —$(C_1$-$C_6$alkyl)-CO—$NR^5R^6$, —$COOR^7$, —$(C_1$-$C_6)$alkyl-CO—$OR^7$, —$(C_1$-$C_6)$alkoxy-$COOR^7$, —$(OCH_2CH_2)_s$—$O(C_1$-$C_6)$alkyl, —$(CH_2CH_2O)_s$—$(C_1$-$C_6)$ alkyl, $((C_1$-$C_6)$alkyl)sulfonyl$(C_1$-$C_6)$alkyl-, —$NH$—$SO_2$ $(C_1$-$C_6)$alkyl, —$N(SO_2(C_1$-$C_6)$alkyl)$_2$, —$C(═NH)NH_2$, —NH—CO—$(C_1$-$C_6)$alkyl, —NH—CO—$NH_2$, —NH—C$(═O)$—NH—$(C_1$-$C_6)$alkyl, —NH—C$(═O)$-(5- to 12-membered)aryl, —NH—C$(═O)$—$(C_1$-$C_6)$alkyl-(5- to 12-membered)aryl, —NH—$(C_1$-$C_6)$alkyl-CO—$OR^7$, —NH—C$(═O)$—$(C_1$-$C_6)$alkyl-CO—$OR^7$, —NH—C$(═O)$—$CH(NH_2)$—$(C_1$-$C_6)$alkyl-CO—$OR^7$, —$(C_3$-$C_{12})$ cycloalkyl, $((C_3$-$C_{12})$cycloalkyl)-$(C_1$-$C_6)$alkyl-, -(5- to 12-membered)aryl, -(5- to 12-membered)aryloxy, —$(C_1$-$C_6)$ alkoxy$C(O)NR^5R^6$, —NH—$(C_1$-$C_6)$alkyl$C(O)$—$NR^5R^6$, —$C(O)NH$—$(C_1$-$C_6)$alkyl-$COOR^7$, ((5- to 12-membered) aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

or a pharmaceutically acceptable salt or solvate thereof.

The present invention also provides compounds of Formula IV or Formula V:

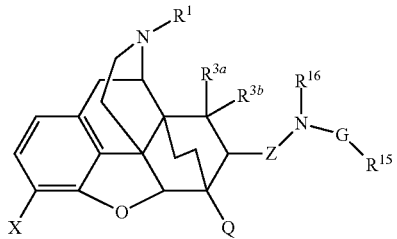

(IV)

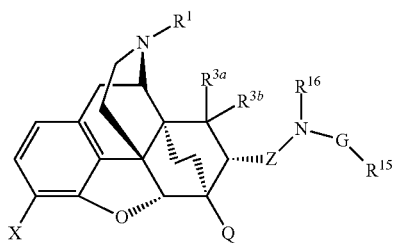

(V)

wherein

G is selected from the group consisting of carbonyl C(=O), sulfonyl S(=O)$_2$, and sulfinyl S(=O);

Q is selected from the group consisting of OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O), —(C$_1$-C$_6$)alkyl, —(OCH$_2$CH$_2$), —OH, —O(C=O)R$^9$, —O—(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl-C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ and R$^{14}$; any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from the group consisting of OH, hydroxy(C$_1$-C$_6$)alkyl-, dihydroxy(C$_1$-C$_6$)alkyl-, halogen, —NH$_2$, —NR$^{20}$(C=O)R$^{12}$, —CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O(C$_1$-C$_6$)alkyl, —(OCH$_2$CH$_2$), —OH, —(CH$_2$)$_p$CHOHCH$_2$OH, CN, —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-; any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

Z is —(CH$_2$)$_m$—, optionally substituted with 1 or 2-(C$_1$-C$_6$)alkyl;

m is an integer 1, 2, 3, 4, 5, or 6;

p is an integer 0, 1 or 2;

s is an integer 1, 2, 3, 4, 5, 6, 7, 8, 9, 10, 11, 12, or 13;

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

R$^{3a}$ and R$^{3b}$ are each independently selected from the group consisting of hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, and ((3- to 12 membered)heterocycle)-(C$_1$-C$_6$)alkoxy-(C$_1$-C$_6$)alkyl-; or R$^{3a}$ and R$^{3b}$ together form (=O);

R$^4$ is selected from the group consisting of —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

$R^5$ and $R^6$ are each independently hydrogen, $-(C_1-C_6)$alkyl, $-(C_3-C_8)$cycloalkyl, $((C_3-C_8)$cycloalkyl$)-(C_1-C_6)$alkyl-, $-COOR^7$, $-(C_1-C_6)$alkyl-CO-$OR^7$, $-CONH_2$, or $(C_1-C_6)$alkyl-CONH—, or $R^5$ and $R^6$ together with the nitrogen atom to which they are attached form a (4- to 8-membered)heterocycle; any of which is optionally substituted with 1 or 2 substituents independently selected from the group consisting of $-(C_1-C_6)$alkyl, OH, halo, $-C(halo)_3$, $-CH(halo)_2$, $-CH_2(halo)$, $-(C_1-C_6)$alkyl-$COOR^7$, $-COOR^7$, $NH_2$, $-NH(C_1-C_6)$alkyl, $-NR^9R^{10}$, $-CN$, $-OR^4$, $-CONR^9R^{10}$, $-NR^9COR^{10}$, $-SR^{11}$, -(3- to 12-membered)carbocyclic ring, -(5- to 12-membered)heterocycle, phenyl, and benzyl;

$R^7$ is selected from the group consisting of hydrogen, $-(C_1-C_6)$alkyl, $-(C_2-C_6)$alkenyl, $-(C_2-C_6)$alkynyl, $-(C_3-C_{12})$cycloalkyl, $-(C_4-C_{12})$cycloalkenyl, $((C_3-C_{12})$cycloalkyl$)-(C_1-C_6)$alkyl-, and $((C_4-C_{12})$cycloalkenyl$)-(C_1-C_6)$alkyl-;

$R^9$ and $R^{10}$ are each independently selected from the group consisting of hydrogen, $-(C_1-C_6)$alkyl, $-(C_2-C_6)$alkenyl, $-(C_2-C_6)$alkynyl, $-(C_1-C_{10})$alkoxy, $-(C_3-C_{12})$cycloalkyl, $-(C_3-C_{12})$cycloalkenyl, $((C_3-C_{12})$cycloalkyl$)-(C_1-C_6)$alkyl-, and $((C_3-C_{12})$cycloalkenyl$)-(C_1-C_6)$alkyl-;

each $R^{11}$ is independently selected from the group consisting of hydrogen, $-(C_1-C_{10})$alkyl, $-(C_2-C_{10})$alkenyl, $-(C_2-C_{10})$alkynyl, $-(C_1-C_{10})$alkoxy, $((C_1-C_6)$alkyl)sulfonyl$(C_1-C_6)$alkyl-, $-(C_3-C_{12})$cycloalkyl, $((C_3-C_{12})$cycloalkyl$)-(C_1-C_6)$alkyl-, $-(C_4-C_{12})$cycloalkenyl, and $((C_4-C_{12})$cycloalkenyl$)-(C_1-C_6)$alkyl-;

$R^{12}$ and $R^{13}$ are each independently selected from the group consisting of hydrogen, $-(C_1-C_{10})$alkyl, $-(C_2-C_{12})$alkenyl, $-(C_2-C_{12})$alkynyl, $-(C_1-C_{10})$alkoxy, $-(OCH_2CH_2)$, $-O(C_1-C_6)$alkyl, $-(C_3-C_{12})$cycloalkyl, $((C_3-C_{12})$cycloalkyl$)-(C_1-C_6)$alkyl-, $-(C_4-C_{12})$cycloalkenyl, $((C_4-C_{12})$cycloalkenyl$)-(C_1-C_6)$alkyl-, $-(C_6-C_{14})$bicycloalkyl, $((C_6-C_{14})$bicycloalkyl$)-(C_1-C_6)$alkyl-, $-(C_8-C_{20})$tricycloalkyl, $((C_8-C_{20})$tricycloalkyl$)-(C_1-C_6)$alkyl-, $-(C_7-C_{14})$bicycloalkenyl, $((C_7-C_{14})$bicycloalkenyl$)-(C_1-C_6)$alkyl-, $-(C_8-C_{20})$tricycloalkenyl, $((C_8-C_{20})$tricycloalkenyl$)-(C_1-C_6)$alkyl-, -(5- to 12-membered)aryl, $((5-$ to 12-membered)aryl$)(C_1-C_6)$alkyl-, -(7- to 12-membered)bicyclic ring system, $((7-$ to 12-membered)bicyclic ring system$)-(C_1-C_6)$alkyl-, -(7- to 12-membered)bicyclic aryl, $((7-$ to 12-membered)bicyclic aryl$)-(C_1-C_6)$alkyl-, -(5- to 12-membered)heteroaryl, $((5-$ to 12-membered)heteroaryl$)-(C_1-C_6)$alkyl-, -(3- to 12-membered)heterocycle, $((3-$ to 12-membered)heterocycle$)-(C_1-C_6)$alkyl-, -(7- to 12-membered)bicycloheterocycle, $((7-$ to 12-membered)bicycloheterocycle$)-(C_1-C_6)$alkyl-, phenyl, benzyl and naphthyl; each of which is optionally substituted with one or two substituents independently selected from the group consisting of OH, (=O), halo, $-C(halo)_3$, $-CH(halo)_2$, $-CH_2(halo)$, $(C_1-C_6)$alkyl, halo$(C_1-C_6)$alkyl-, $-(C_2-C_6)$alkenyl, $-(C_2-C_6)$alkynyl, hydroxy$(C_1-C_6)$alkyl-, phenyl, benzyl, $NH_2$, $-NH(C_1-C_6)$alkyl, CN, SH, $OR^4$, $-CONR^5R^6$, $-COOR^7$, $-(C_3-C_{12})$cycloalkyl, $((C_3-C_{12})$cycloalkyl$)-(C_1-C_6)$alkyl-, -(5- to 12-membered)aryl, $((5-$ to 12-membered)aryl$)-(C_1-C_6)$alkyl-, -(5- to 12-membered)heteroaryl, $((5-$ to 12-membered)heteroaryl$)-(C_1-C_6)$alkyl-, -(3- to 12-membered)heterocycle, $((3-$ to 12-membered)heterocycle$)-(C_1-C_6)$alkyl-, -(7- to 12-membered)bicycloheterocycle, and $((7-$ to 12-membered)bicycloheterocycle$)-(C_1-C_6)$alkyl-;

$R^{14}$ is selected from the group consisting of $-COOR^7$, $-(C_1-C_6)$alkyl-CO-$OR^7$, $-C(=O)-(C_1-C_6)$alkyl-$COOR^7$, $-(C_1-C_6)$alkyl-C(=O)-$(C_1-C_6)$alkyl-$COOR^7$, $-CONH_2$, and $(C_1-C_6)$alkyl-CONH—;

$R^{15}$ is selected from the group consisting of $R^{20}$, $R^{21}$, and $R^{22}$;

$R^{16}$ is selected from the group consisting of hydrogen, $-(C_1-C_6)$alkyl, $-(C_2-C_6)$alkenyl, $-(C_2-C_6)$alkynyl, $-(C_1-C_{10})$alkoxy, $-C(=O)-(C_1-C_6)$alkyl, $-(C_3-C_{12})$cycloalkyl, $((C_3-C_{12})$cycloalkenyl, $((C_3-C_{12})$cycloalkyl$)-(C_1-C_6)$alkyl-, $((C_3-C_{12})$cycloalkenyl$)-(C_1-C_6)$alkyl-, -(5- to 12-membered)aryl, $((5-$ to 12-membered)aryl$)-(C_1-C_6)$alkyl-, -(5- to 12-membered)heteroaryl, $((5-$ to 12-membered)heteroaryl$)-(C_1-C_6)$alkyl-, -(3- to 12-membered)heterocycle, and $((3-$ to 12-membered)heterocycle$)-(C_1-C_6)$alkyl; any of which is optionally substituted with 1 or 2 substituents independently selected from the group consisting of $-(C_1-C_6)$alkyl, OH, halo, $-C(halo)_3$, $-CH(halo)_2$, $-CH_2(halo)$, $-(C_1-C_6)$alkyl-$COOR^7$, $-COOR^7$, $NH_2$, $-NH(C_1-C_6)$alkyl, $-NR^9R^{10}$, $-CN$, $-OR^4$, $-CONR^9R^{10}$, $-NR^9COR^{10}$, $-SR^{11}$, -(3- to 12-membered)carbocyclic ring, -(5- to 12-membered)heterocycle, phenyl, and benzyl;

$R^{20}$ is selected from the group consisting of hydrogen, $-(C_1-C_{10})$alkyl, $-(C_2-C_{12})$alkynyl, $-(C_1-C_{10})$alkoxy, $-(OCH_2CH_2)_s-O(C_1-C_6)$alkyl, $-(CH_2CH_2O)_s-(C_1-C_6)$alkyl, CN, $-CONR^5R^6$, $-(C_1-C_6)$alkyl-CO-$NR^5R^6$, $-COOR^7$, $-(C_1-C_6)$alkyl-CO-$OR^7$, $-(C_1-C_6)$alkoxy-$COOR^7$, $-(C_3-C_{12})$cycloalkyl, $((C_3-C_{12})$cycloalkyl$)-(C_1-C_6)$alkyl-, $-(C_4-C_{12})$cycloalkenyl, $((C_4-C_{12})$cycloalkenyl$)-(C_1-C_6)$alkyl-, $-(C_6-C_{14})$bicycloalkyl, $((C_6-C_{14})$bicycloalkyl$)-(C_1-C_6)$alkyl-, $-(C_8-C_{20})$tricycloalkyl, $((C_8-C_{20})$tricycloalkyl$)-(C_1-C_6)$alkyl-, $-(C_7-C_{14})$bicycloalkenyl, $((C_7-C_{14})$bicycloalkenyl$)-(C_1-C_6)$alkyl-, $-(C_8-C_{20})$tricycloalkenyl, $((C_8-C_{20})$tricycloalkenyl$)-(C_1-C_6)$alkyl-, -(5- to 12-membered)aryl, $((5-$ to 12-membered)aryl$)-(C_1-C_6)$alkyl-, -(7- to 12-membered)bicyclic ring system, $((7-$ to 12-membered)bicyclic ring system$)-(C_1-C_6)$alkyl-, -(7- to 12-membered)bicyclic aryl, $((7-$ to 12-membered)bicyclic aryl$)-(C_1-C_6)$alkyl-, -(5- to 12-membered)heteroaryl, $((5-$ to 12-membered)heteroaryl$)-(C_1-C_6)$alkyl-, -(3- to 12-membered)heterocycle, $((3-$ to 12 membered)heterocycle$)-(C_1-C_6)$alkyl-, -(7- to 12-membered)bicycloheterocycle, $((7-$ to 12-membered)bicycloheterocycle$)-(C_1-C_6)$alkyl-, phenyl, benzyl and naphthyl; each of which is optionally substituted with one or two substituents independently selected from the group consisting of $-OH$, (=O), halo, $-C(halo)_3$, $-CH(halo)_2$, $-CH_2(halo)$, $(C_1-C_6)$alkyl, halo$(C_1-C_6)$alkyl-, $-(C_2-C_6)$alkenyl, $-(C_2-C_6)$alkynyl, hydroxy$(C_1-C_6)$alkyl-, dihydroxy$(C_1-C_6)$alkyl-, $-(C_1-C_6)$alkoxy, $((C_1-C_6)$alkoxy$)CO(C_1-C_6)$alkoxy-, phenyl, benzyl, $-NH_2$, $-NH(C_1-C_6)$alkyl, $-(C_1-C_6)$alkyl-NH$(C_1-C_6)$alkyl-$R^{14}$, $-CN$, $-SH$, $-OR^4$, $-CONR^5R^6$, $-(C_1-C_6$alkyl$)-CO-NR^5R^6$, $-COOR^7$, $-(C_1-C_6)$alkyl-CO-$OR^7$, $-(C_1-C_6)$alkoxy-$COOR^7$, $-(OCH_2CH_2)_s-O(C_1-C_6)$alkyl, $-(CH_2CH_2O)_s-(C_1-C_6)$alkyl, $((C_1-C_6)$alkyl)sulfonyl$(C_1-C_6)$alkyl-, $-NH-SO_2(C_1-C_6)$alkyl, $-N(SO_2(C_1-C_6)$alkyl$)_2$, $-C(=NH)NH_2$, $-NH-CO-(C_1-C_6)$alkyl, $-NH-CO-NH_2$, $-NH-C(=O)-NH-(C_1-C_6)$alkyl, $-NH-C(=O)$-(5- to 12-membered)aryl, $-NH-C(=O)-(C_1-C_6)$alkyl-(5- to 12-membered)aryl, $-NH-(C_1-C_6)$alkyl-CO-$OR^7$, $-NH-C(=O)-(C_1-C_6)$alkyl-CO-$OR^7$, $-NH-C(=O)-CH(NH_2)-(C_1-C_6)$alkyl-CO-$OR^7$, $-(C_3-C_{12})$cycloalkyl, $((C_3-C_{12})$cycloalkyl$)-(C_1-C_6)$alkyl-, -(5- to 12-membered)aryl, -(5- to 12-membered)aryloxy, $-(C_1-C_6)$alkoxyC(O)$NR^5R^6$, $-NH-(C_1-C_6)$alkylC(O)-$NR^5R^6$, $-C(O)NH-(C_1-C_6)$alkyl-$COOR^7$, $((5-$ to 12-membered)aryl$)-(C_1-C_6)$alkyl-, -(5- to 12-membered)heteroaryl, $((5-$ to 12-membered)heteroaryl$)-(C_1-C_6)$alkyl-, -(3- to 12-membered)heterocycle, $((3-$ to 12-membered)heterocycle$)-(C_1-C_6)$alkyl-, -(7- to 12-membered)

bicycloheterocycle, and ((7- to 12-membered)bicycloheterocycle)-($C_1$-$C_6$)alkyl-;

$R^{22}$ is an amino group unsubstituted or substituted one or two times with substituents independently selected from the group consisting of —($C_1$-$C_{10}$)alkyl, —($C_2$-$C_{12}$)alkenyl, —($C_3$-$C_{12}$)cycloalkyl, (($C_3$-$C_{12}$)cycloalkyl)-($C_1$-$C_6$)alkyl-, -(5- to 12-membered)aryl (e.g. phenyl or naphthyl), ((5- to 12-membered)aryl)-($C_1$-$C_6$)alkyl- (e.g. benzyl), -(5- to 12-membered)heteroaryl, ((5- to 12-membered)heteroaryl)-($C_1$-$C_6$)alkyl-, -(3- to 12-membered)heterocycle, or ((3- to 12 membered)heterocycle)-($C_1$-$C_6$)alkyl-; each of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, and -(5- to 12-membered)heterocycle;

$R^{21}$ is $R^{20}$ or an alpha-amino compound of structure:

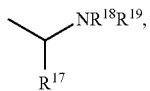

wherein each $R^{17}$ is independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkyl-CN, —($C_1$-$C_6$)alkyl-CONR$^9$R$^{10}$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), ($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered) carbocyclic ring, -(5- to 12-membered)heterocycle, phenyl, and benzyl; and $R^{18}$ and $R^{19}$ are each independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, and —C(=O)—($C_1$-$C_6$)alkyl; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), ($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or $R^{19}$ may optionally be a peptide-forming moiety having the structure

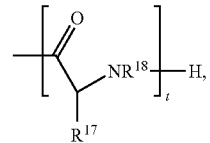

wherein t is an integer 1, 2 or 3;

provided that 1) when $R^1$ is cyclopropylmethyl, G is C=O, Q and X are both —OCH$_3$, Z is —CH$_2$—, $R^{15}$ is —CH(NH$_2$)CH$_3$, and $R^{16}$ is hydrogen, then either:

a) at least one of $R^{3a}$ and $R^{3b}$ is a substituent other than hydrogen; or b) at least one of $R^{18}$ and $R^{19}$ is a substituent other than hydrogen;

2) when $R^1$ is cyclopropylmethyl, G is S(=O)$_2$, X and Q are both —OCH$_3$, Z is —CH$_2$—, $R^{15}$ is —CH$_3$, and $R^{16}$ is benzyl, then at least one of $R^{3a}$ and $R^{3b}$ is a substituent other than hydrogen; and 3) when $R^1$ is cyclopropylmethyl, G is C=O, Q and X are both —OCH$_3$, Z is —CH$_2$—, $R^{15}$ is $R^{20}$, and $R^{20}$ is unsubstituted ($C_1$-$C_{10}$)alkyl, then $R^{16}$ is hydrogen;

or a pharmaceutically acceptable salt or solvate thereof.

In certain embodiments, the present invention provides compounds of Formula IV or Formula V, wherein, in addition or as an alternative to the above proviso 3), the proviso 3') applies that when $R^1$ is cyclopropylmethyl, G is C(=O), X and Q are both —OCH$_3$, Z is —CH$_2$—, $R^{15}$ is —CH$_3$, and $R^{16}$ is benzyl, then at least one of $R^{3a}$ and $R^{3b}$ is a substituent other than hydrogen.

Many variations and specific embodiments are described later.

In another aspect, the invention relates to pharmaceutical compositions comprising an effective amount of a Compound of the Invention, as described herein, and one or more pharmaceutically acceptable carriers or excipients.

It is an object of certain embodiments of the present invention to provide new Compounds of the Invention that have activity at one or more of the opioid receptors, including the ORL-1, μ, δ, and/or κ opioid receptors. Some compounds with activity at these receptors are known in the literature and include, e.g., JTC-801 (described in WO 99/48492; and Shinkai et al., "4-aminoquinolines: Novel nociceptin antagonists with analgesic activity", *J. Med. Chem.*, 2000, 43:4667-4677) and J-113397 (described in WO 98/54168; and Kawamoto et al., "Discovery of the first potent and selective small molecule opioid receptor-like (ORL-1) antagonist: 1-[(3R,4R)-1-cyclooctylmethyl-3-hydroxymethyl-4-piperidyl]-3-ethyl-1,3-dihydro-2H-benzimidazol-2-one (J-113397)", *J. Med. Chem.*, 1999, 42:5061-6063).

Certain Compounds of the Invention may have agonist activity at the ORL-1, μ, δ and/or κ receptors. Certain Compounds of the Invention may have antagonist activity at the ORL-1, μ, δ and/or κ receptors. A given Compound of the Invention may have agonist activity at one or more opioid receptor(s), while having agonist or antagonist activity at one or more other opioid receptor(s).

Compounds of the Invention may be useful as analgesics to treat, ameliorate, or prevent pain; or as agents to treat, ameliorate, or prevent addictive disorders; or as agents to treat, ameliorate, or prevent withdrawal from alcohol and/or drugs of addiction; or as agents to treat, ameliorate, or prevent pruritic conditions; or as agents to treat or prevent constipation; or as agents to treat or prevent diarrhea (each of pain, alcohol withdrawal, drug withdrawal, addictive disorders, pruritis, constipation, and diarrhea being a "Condition").

In a further aspect, the present invention provides methods for treating a Condition, comprising administering to a subject in need thereof a therapeutically effective amount of a Compound of the Invention. In certain embodiments, the Condition is pain (chronic or acute pain). The Compounds of the Invention are particularly useful for treating chronic pain. Alternatively, the Compounds of the Invention may be used in the preparation of a medicine useful for treating a Condition.

Compounds of the Invention can be used to treat, ameliorate, or prevent acute or chronic pain. Examples of pain that can be treated, ameliorated, or prevented using a Compound of the Invention include, but are not limited to, cancer pain, neuropathic pain, labor pain, myocardial infarction pain, pancreatic pain, colic pain, post operative pain, headache pain, migraine pain, muscle pain, arthritic pain, and pain associated with a periodontal disease, including gingivitis and periodontitis.

Compounds of the Invention can also be used to treat, ameliorate, or prevent pain associated with inflammation or with an inflammatory disease in an animal. Such pain can arise where there is an inflammation of the body tissue which can be a local inflammatory response or a systemic inflammation. For example, a Compound of the Invention can be used to treat, ameliorate, or prevent pain associated with inflammatory diseases including, but not limited to, organ transplant rejection; reoxygenation injury resulting from organ transplantation (see Grupp et al., J. Mol, Cell Cardiol. 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. Compounds of the Invention can also be used to treat, ameliorate, or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

Compounds of the Invention can also be used to treat, ameliorate, or prevent pain associated with nerve injury (i.e., neuropathic pain). Chronic neuropathic pain is a heterogeneous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

Compounds of the Invention can be used to treat, ameliorate, or prevent pain associated with migraine including, but not limited to, migraine without aura ("common migraine"), migraine with aura ("classic migraine"), migraine without headache, basilar migraine, familial hemiplegic migraine, migrainous infarction, and migraine with prolonged aura.

The present invention further provides methods for treating a Condition, comprising administering to a subject in need thereof a therapeutically effective amount of a Compound of the Invention. In certain embodiments, the Condition is pain (chronic or acute pain). The Compounds of the Invention are particularly useful for treating chronic pain. In certain embodiments, the Compound of the Invention is an ORL-1 receptor antagonist. In other embodiments, the Compound of the Invention is an agonist at one or more of the μ, δ and/or κ receptor. In other embodiments, the Compound of the Invention is both an ORL-1 receptor antagonist and an agonist at one or more of the μ, δ and/or κ receptor. In other embodiments, the Compound of the Invention is both an ORL-1 receptor antagonist and an agonist at the u receptor. In certain non-limiting embodiments, the Compound of the Invention produces fewer side effects and/or less severe side effects than currently available analgesic opioid compounds when administered at doses producing equivalent levels of analgesia and/or anti-hyperalgesia.

In certain non-limiting embodiments, the Compound of the Invention exhibits a substantially linear dose response curve, such that the bell-shaped dose response curve observed for most opioid analgesics (i.e. low and high doses do not produce significant analgesia, whereas mid-range doses produce analgesia) is not observed for the Compound of the Invention. It is expected, therefore, that it will be easier to titrate to an effective dose of the Compound of the Invention in a patient than it is for conventional opioid analgesics. It is further expected that the Compound of the Invention will produce effective analgesia and/or anti-hyperalgesia in a patient who has become tolerant to conventional opioids, and for whom a conventional opioid is no longer an effective treatment. It is further expected that a Compound of the Invention will produce effective analgesia and/or anti-hyperalgesia at doses that do not induce side effects such as respiratory depression in patients for whom a dose of a conventional opioid that is high enough to be an effective treatment also induces significant side effects such as respiratory depression.

The present invention further provides methods for preventing a Condition, comprising administering to an animal in need thereof a Condition-preventing effective amount of a Compound of the Invention.

Another object of the invention is to provide buprenorphine analog compounds useful for treating or preventing constipation, preferably μ opioid receptor-induced constipation. More specifically, the present invention provides compounds of Formula I below, and the pharmaceutically acceptable salts and solvates thereof having activity as μ receptor agonists or antagonists. In certain embodiments, Compounds of the Invention may have activity at two or more opioid receptors, and that activity may, but need not be, the same (agonist or antagonist). Certain Compounds of the Invention are expected to be substantially restricted to the GI tract.

Compounds of the Invention that have μ antagonist activity and are substantially restricted to the GI tract will significantly reduce or prevent constipation that would otherwise occur in a patient as a result of treatment with a μ agonist. In one embodiment, the reduction or prevention of constipation is obtained without reducing the desired analgesic effect of the μ agonist. Compounds of the Invention that also exhibit lc agonist activity should additionally stimulate GI motility via a non-μ receptor mediated mechanism.

The present invention provides a method for treating a Condition in an animal. In certain embodiments, the Condition treated will be pain (acute or chronic pain). The present invention further provides a method for treating or preventing constipation, preferably constipation associated with μ-opioid agonist therapy, by administering an effective amount of a Compound of the Invention to a patient in need of such treatment or prevention. In one embodiment, the Compound of the Invention is a μ antagonist that is substantially restricted to the GI tract. In another embodiment, the Compound of the Invention is both a μ antagonist and a κ agonist, and is substantially restricted to the GI tract. In another embodiment, the method comprises co-administering to a patient both an effective amount of a Compound of the Invention that is a μ antagonist and is substantially restricted to the GI tract, and an analgesically effective amount of a μ agonist.

In another embodiment, the method comprises co-administration to a patient of both an effective amount of a Compound of the Invention that is both a μ antagonist and a agonist, and which is substantially restricted to the GI tract, and an analgesically effective amount of a μ agonist.

The present invention further provides pharmaceutical compositions comprising a therapeutically effective amount of a Compound of the Invention admixed with a pharmaceutically acceptable carrier or excipient. Such compositions are useful for treating or preventing a Condition in an animal. The pharmaceutical compositions of the present invention may be formulated as immediate release formulations, or as controlled release formulations. Pharmaceutical compositions of the present invention may be formulated for administration by any of a number of different routes known in the art, including but not limited to, oral, intradermal, intramuscular, intraperitoneal, parenteral, intravenous, subcutaneous, intranasal, epidural, sublingual, intracerebral, intravaginal, transdermal, transmucosal, rectal, by inhalation, or topical (particularly to the ears, nose, eyes, or skin).

The present invention further provides methods for preparing a composition, comprising the step of admixing a Compound of the Invention and a pharmaceutically acceptable carrier or excipient to form a pharmaceutical composition.

The invention still further relates to a kit comprising a container containing an effective amount of a Compound of the Invention. A kit may further comprise instructions for use of the Compound of the Invention.

Further aspects of this invention will become apparent to those skilled in the art from the following detailed description of various embodiments.

DETAILED DESCRIPTION

The Compounds of the Invention are novel buprenorphine analogs. They are useful for treating one or more Conditions, such as pain or constipation. Compounds of the Invention may provide a reduced liability for developing analgesic tolerance and physical dependence.

The Compounds of the Invention are useful for modulating a pharmacodynamic response from opioid receptors either centrally or peripherally, or both. The Compounds of the Invention may also be useful for modulating a pharmacodynamic response from one or more opioid receptors (ORL-1, μ, δ, κ) either centrally or peripherally, or both. The pharmacodynamic response may be attributed to the compound stimulating (agonizing) or inhibiting (antagonizing) the one or more receptors. Certain Compounds of the Invention may inhibit (antagonize) one or more receptor(s), while also stimulating (agonizing) or inhibiting (antagonizing) one or more other receptor(s). Compounds of the Invention having agonist activity may be either full or partial agonists.

In certain embodiments, Compounds of the Invention can be used in combination with at least one other therapeutic agent. The other therapeutic agent can be, but is not limited to, a μ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof. Embodiments of such combinations are discussed in the later section on Pharmaceutical Compositions and Administration.

Illustrative Embodiments

The invention relates to compounds of Formula I or IA (shown below):

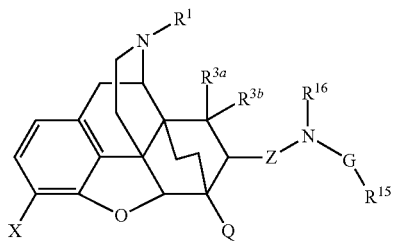

(I)

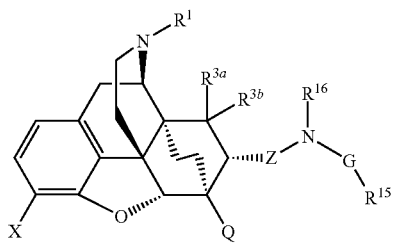

(IA)

wherein

G is selected from the group of carbonyl C(=O), sulfonyl S(=O)$_2$, and sulfinyl S(=O);

Q is selected from the group of OH, (C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O), —(C$_1$-C$_6$)alkyl, —(OCH$_2$CH$_2$), —OH, —O(C=O)R$^9$, —O—(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl-C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ and R$^{14}$; any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from the group of OH, hydroxy(C$_1$-C$_6$)alkyl-, dihydroxy(C$_1$-C$_6$)alkyl-, halogen, —NH$_2$, —NR$^{20}$(C=O)R$^{12}$, —CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O(C$_1$-C$_6$)alkyl, —(OCH$_2$CH$_2$), —OH, —(CH$_2$)$_p$CHOHCH$_2$OH, CN, —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-; any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

Z is —(CH$_2$)$_m$—, optionally substituted with 1 or 2-(C$_1$-C$_6$)alkyl;

m is an integer 1, 2, 3, 4, 5, or 6;

p is an integer 0, 1 or 2;

s is an integer 1, 2, 3, 4, 5, 6, 7, 8, 9, 10, 11, 12, or 13;

R$^1$ is selected from the group of hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

R$^{3a}$ and R$^{3b}$ are each independently selected from the group of hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, and ((3- to 12 membered)heterocycle)-(C$_1$-C$_6$)alkoxy-(C$_1$-C$_6$)alkyl-; or R$^{3a}$ and R$^{3b}$ together form (=O);

R$^4$ is selected from the group of —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^7$ is selected from the group of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-;

each $R^{11}$ is independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl-($C_1$-$C_6$)alkyl-, —($C_3$-$C_{12}$)cyclo alkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$), —O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl, and naphthyl; each of which is optionally substituted with one or two substituents independently selected from the group consisting of OH, (═O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from the group consisting of —COOR$^7$, —($C_1$-$C_6$)alkyl-CO—OR$^7$, —C(═O)—($C_1$-$C_6$)alkyl-COOR$^7$, —($C_1$-$C_6$)alkyl-C(═O)—($C_1$-$C_6$)alkyl-COOR$^7$, —CONH$_2$, and ($C_1$-$C_6$)alkyl-CONH—;

$R^{15}$ is $R^{20}$ or $R^{21}$;

$R^{16}$ is selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —C(═O)—($C_1$-$C_6$)alkyl, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, and ((3- to 12-membered)heterocycle)-($C_1$-$C_6$)alkyl; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^{20}$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O), —($C_1$-$C_6$)alkyl, —NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of —OH, (═O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —CN, —SH, —OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(═NH)NH$_2$, —NH—CO—($C_1$-$C_6$)alkyl, —NH—CO—NH$_2$, —NH—C(═O)—NH—($C_1$-$C_6$)alkyl, —NH—C(═O)-(5- to 12-membered)aryl, —NH—C(═O)—($C_1$-$C_6$)alkyl-(5- to 12-membered)aryl, —NH—($C_1$-$C_6$)alkyl-CO—OR$^7$, —NH—C(═O)—($C_1$-$C_6$)alkyl-CO—OR$^7$, —NH—C(═O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{21}$ is R$^{20}$ or an alpha-amino compound of structure:

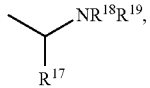

wherein each R$^{17}$ is independently selected from the group consisting of hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkyl-CN, —(C$_1$-C$_6$)alkyl-CONR$^9$R$^{10}$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, and ((3- to 12 membered)heterocycle)-(C$_1$-C$_6$)alkoxy-(C$_1$-C$_6$)alkyl-; or R$^{17}$ together with R$^{18}$ or R$^{19}$ and the N to which they are attached may form a 3- to 12-membered heterocycle; any of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), (C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and R$^{18}$ and R$^{19}$ are each independently selected from the group consisting of hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, ((C$_3$-C$_{12}$)cycloalkenyl)-(C$_1$-C$_6$)alkyl-, —C(=O)—(C$_1$-C$_6$)alkyl; any of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), (C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or R$^{19}$ may optionally be a peptide-forming moiety having the structure

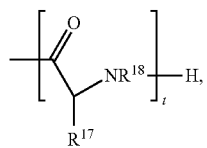

where t is an integer 1, 2 or 3;

provided that when R$^1$ is cyclopropylmethyl, G is C=O, Q and X are both —OCH$_3$, Z is —CH$_2$—, R$^{15}$ is —CH(NH$_2$)CH$_3$, and R$^{16}$ is hydrogen, then either:

a) at least one of R$^{3a}$ and R$^{3b}$ is a substituent other than hydrogen; or b) at least one of R$^{18}$ and R$^{19}$ is a substituent other than hydrogen;

and further provided that when R$^1$ is cyclopropylmethyl, G is S(=O)$_2$, X and Q are both —OCH$_3$, Z is —CH$_2$—, R$^{15}$ is —CH$_3$, and R$^{16}$ is benzyl, then at least one of R$^{1a}$ and R$^{3b}$ is a substituent other than hydrogen;

or a pharmaceutically acceptable salt or solvate thereof.

The present invention further provides compounds of Formula IB:

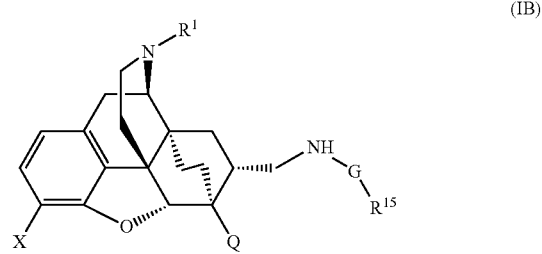

(IB)

wherein

G is selected from the group consisting of carbonyl C(=O), sulfonyl S(=O)$_2$, and sulfinyl S(=O);

Q is selected from the group consisting of OH, —(C$_1$-C$_{10}$)alkoxy, ((C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O), —(C$_1$-C$_6$)alkyl, —(OCH$_2$CH$_2$), —OH, —O(C=O)R$^9$, —O(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl-C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ and R$^{14}$; any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from the group consisting of OH, hydroxy (C$_1$-C$_6$)alkyl-, dihydroxy(C$_1$-C$_6$)alkyl-, halogen, —NH$_2$, —NR$^{20}$(C=O)R$^{12}$, —CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O(C$_1$-C$_6$)alkyl, —(OCH$_2$CH$_2$), —OH, —(CH$_2$)$_p$CHOHCH$_2$OH, CN, —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-($C_1$-$C_6$)alkyl-, and ((7- to 12-membered)-bicycloheterocycle)-($C_1$-$C_6$)alkoxy-; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered) carbocyclic ring, -(5- to 12-membered)heterocycle, phenyl, and benzyl;

p is an integer 0, 1 or 2;

s is an integer 1, 2, 3, 4, 5, 6, 7, 8, 9, 10, 11, 12, or 13;

$R^1$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^4$ is selected from the group consisting of —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—; or $R^5$ and $R^6$ together with the nitrogen atom to which they are attached form a (4- to 8-membered)heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^7$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, and (($C_3$-$C_{12}$)cycloalkenyl)-($C_1$-$C_6$)alkyl-;

each $R^{11}$ independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)-sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, and (($C_4$-$C_{12}$)cycloalkenyl)-($C_1$-$C_6$)alkyl-;

$R^{12}$ and $R^{13}$ are each independently selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from the group consisting of —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, and ($C_1$-$C_6$)alkyl-CONH—;

$R^{15}$ is $R^{20}$ or $R^{21}$;

$R^{20}$ is selected from the group consisting of hydrogen, —($C_1$-$C_{10}$)alkyl, (($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O), —($C_1$-$C_6$)alkyl, —NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, (($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy) CO(C$_1$-C$_6$)alkoxy-, phenyl, benzyl, —NH$_2$, —NH(C$_1$-C$_6$) alkyl, —(C$_1$-C$_6$)alkyl-NH(C$_1$-C$_6$)alkyl-R$^{14}$, —CN, —SH, —OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O), —(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$) alkyl-;

R$^{21}$ is R$^{20}$ or an alpha-amino compound of structure:

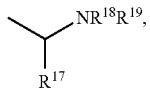

wherein each R$^{17}$ is independently selected from the group consisting of hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$) alkyl-, —C(halo)$_3$, —CH(halo)$_2$, —CH$_2$(halo), —(C$_1$-C$_6$) alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkyl-CN, —(C$_1$-C$_6$)alkyl-CONR$^9$R$^{10}$, (C$_1$-C$_6$) alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$) alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered) aryl)-(C$_1$-C$_6$)alkoxy-(C$_1$-C$_6$)alkyl-, -(5- to 12-membered) heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, and ((3- to 12 membered)heterocycle)-(C$_1$-C$_6$)alkoxy-(C$_1$-C$_6$)alkyl-; or R$^{17}$ together with R$^{18}$ or R$^{19}$ and the N to which they are attached may form a 3- to 12-membered heterocycle; any of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and R$^{18}$ and R$^{19}$ are each independently selected from the group consisting of hydrogen, —(C$_1$-C$_6$)alkyl, —(C$_2$-C$_6$) alkenyl, —(C$_2$-C$_6$)alkynyl, —(C$_1$-C$_{10}$)alkoxy, —(C$_3$-C$_{12}$) cycloalkyl, —(C$_3$-C$_{12}$)cycloalkenyl, ((C$_3$-C$_{12}$)cycloalkyl)-(C$_1$-C$_6$)alkyl-, ((C$_3$-C$_{12}$)cycloalkenyl)-(C$_1$-C$_6$)alkyl-, and —C(=O)—(C$_1$-C$_6$)alkyl; any of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or R$^{19}$ may optionally be a peptide-forming moiety having the structure

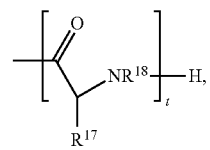

wherein t is an integer 1, 2 or 3;

provided that when R$^1$ is cyclopropylmethyl, G is C=O, and Q and X are both —OCH$_3$, then either:

a) R$^{15}$ is a substituent other than —CH(NH$_2$)CH$_3$ or b) at least one of R$^{18}$ and R$^{19}$ is a substituent other than hydrogen.

or a pharmaceutically acceptable salt or solvate thereof.

In another embodiment, the invention provides compounds of Formula II:

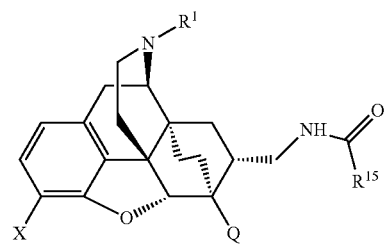

(II)

wherein

Q is selected from the group consisting of OH, —(C$_1$-C$_{10}$) alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O (C$_1$-C$_6$)alkyl, —(CH$_2$CH$_2$O), —(C$_1$-C$_6$)alkyl, —(OCH$_2$CH$_2$), —OH, —O(C=O)R$^9$, —O—(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl-C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ and R$^{14}$; any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from the group consisting of OH, hydroxy($C_1$-$C_6$)alkyl-, dihydroxy($C_1$-$C_6$)alkyl-, halogen, —$NH_2$, —$NR^{20}$(C=O)$R^{12}$, —$CONR^{12}R^{13}$, —($C_1$-$C_6$)alkyl-$CONH_2$, —($C_1$-$C_6$)alkyl-COOH, —COOH, —O—($C_1$-$C_6$)alkyl-COOH, —O—($C_1$-$C_6$)alkyl-$CONH_2$, —($C_1$-$C_{10}$)alkyl, —($C_2$-$C_{10}$)alkenyl, —($C_2$-$C_{10}$)alkynyl, —($C_1$-$C_{10}$)alkoxy, —($OCH_2CH_2$)$_s$—O($C_1$-$C_6$)alkyl, —($OCH_2CH_2$)$_s$—OH, —($CH_2$)$_p$CHOHCH$_2$OH, CN, —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

p is an integer 0, 1 or 2;

s is an integer 1, 2, 3, 4, 5, 6, 7, 8, 9, 10, 11, 12, or 13;

$R^1$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^4$ is selected from the group consisting of —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—; or $R^5$ and $R^6$ together with the nitrogen atom to which they are attached form a (4- to 8-membered)heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^7$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, and (($C_3$-$C_{12}$)cycloalkenyl)-($C_1$-$C_6$)alkyl-;

each $R^{11}$ is independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)-sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, and (($C_4$-$C_{12}$)cycloalkenyl)-($C_1$-$C_6$)alkyl-;

$R^{12}$ and $R^{13}$ are each independently selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($OCH_2CH_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from the group consisting of —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, and ($C_1$-$C_6$)alkyl-CONH—;

$R^{15}$ is $R^{20}$ or $R^{21}$;

$R^{20}$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($OCH_2CH_2$)$_s$—O($C_1$-$C_6$)alkyl, —(CH$_2$CH$_2$O)$_s$—($C_1$-$C_6$)alkyl, —NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —NH$_2$, —NH($C_1$-$C_6$)alkyl, -($C_1$-$C_6$)alkyl-NH($C_1$-$C_6$)alkyl-$R^{14}$, —CN, —SH, —OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{21}$ is $R^{20}$ or an alpha-amino compound of structure:

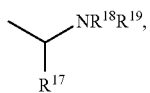

wherein each $R^{17}$ independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkyl-CN, —($C_1$-$C_6$)alkyl-CONR$^9$R$^{10}$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and $R^{18}$ and $R^{19}$ are each independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, —C(=O)—($C_1$-$C_6$)alkyl; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or $R^{19}$ may optionally be a peptide-forming moiety having the structure

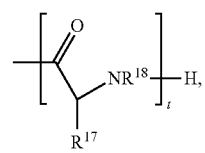

wherein t is an integer 1, 2 or 3;

provided that when $R^1$ is cyclopropylmethyl, G is C=O, and Q and X are both —OCH$_3$, then either:

a) $R^{15}$ is a substituent other than —CH(NH$_2$)CH$_3$ or b) at least one of $R^{18}$ and $R^{19}$ is a substituent other than hydrogen.

or a pharmaceutically acceptable salt or solvate thereof.

In another embodiment, the present invention provides compounds of Formula III:

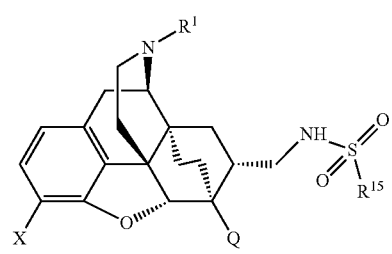

(III)

wherein

Q is selected from the group consisting of OH, —($C_1$-$C_{10}$)alkoxy, —($C_1$-$C_{10}$)alkyl, —($C_3$-$C_{12}$)cycloalkyl, -(5- to 12-membered)aryl, ((C$_3$-$C_{12}$)cycloalkyl)-($C_1$-$C_6$)alkyl-, -(5- to 12-membered)aryl)-($C_1$-$C_6$)alkyl-, —(OCH$_2$CH$_2$)$_s$—O($C_1$-$C_6$)alkyl, —(CH$_2$CH$_2$O), —($C_1$-$C_6$)alkyl, —(OCH$_2$CH$_2$), —OH, —O(C═O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

X is selected from the group consisting of OH, hydroxy($C_1$-$C_6$)alkyl-, dihydroxy($C_1$-$C_6$)alkyl-, halogen, —NH$_2$, —NR$^{20}$(C═O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$), —OH, —(CH$_2$)$_p$CHOHCH$_2$OH, CN, —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

p is an integer 0, 1 or 2;

s is an integer 1, 2, 3, 4, 5, 6, 7, 8, 9, 10, 11, 12, or 13;

R$^1$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, (($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

R$^4$ is selected from the group consisting of —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)-bicycloheterocycle)-($C_1$-$C_6$)alkyl-;

R$^5$ and R$^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—; or R$^5$ and R$^6$ together with the nitrogen atom to which they are attached form a (4- to 8-membered)heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

R$^7$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

R$^9$ and R$^{10}$ are each independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, and (($C_3$-$C_{12}$)cycloalkenyl)-($C_1$-$C_6$)alkyl-;

each R$^{11}$ is independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl-($C_1$-$C_6$)alkyl-, —($C_3$-$C_{12}$)cyclo alkyl, (($C_3$-$C_{12}$)cycloalkyl)-($C_1$-$C_6$)alkyl-, —($C_4$-$C_{12}$)cycloalkenyl, and (($C_4$-$C_{12}$)cycloalkenyl)-($C_1$-$C_6$)alkyl-;

R$^{12}$ and R$^{13}$ are each independently selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of OH, (═O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH ($C_1$-$C_6$)alkyl, CN, SH, $OR^4$, —$CONR^5R^6$, —$COOR^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from the group consisting of —$COOR^7$, —($C_1$-$C_6$)alkyl-CO—$OR^7$, —C(═O)—($C_1$-$C_6$)alkyl-$COOR^7$, —($C_1$-$C_6$)alkyl-C(═O)—($C_1$-$C_6$)alkyl-$COOR^7$, —$CONH_2$, and ($C_1$-$C_6$)alkyl-CONH—;

$R^{15}$ is $R^{20}$;

$R^{20}$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O), —($C_1$-$C_6$)alkyl, —$NH_2$, —NH($C_1$-$C_6$)alkyl, CN, —$CONR^5R^6$, —($C_1$-$C_6$)alkyl-CO—$NR^5R^6$, —$COOR^7$, —($C_1$-$C_6$)alkyl-CO—$OR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of —OH, (═O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —$NH_2$, —NH($C_1$-$C_6$)alkyl, —($C_1$-$C_6$)alkyl-NH($C_1$-$C_6$)alkyl-$R^{14}$, —CN, —SH, —$OR^4$, —$CONR^5R^6$, —($C_1$-$C_6$alkyl)-CO—$NR^5R^6$, —$COOR^7$, —($C_1$-$C_6$)alkyl-CO—$OR^7$, —($C_1$-$C_6$)alkoxy-$COOR^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(═NH)NH$_2$, —NH—CO—($C_1$-$C_6$)alkyl, —NH—CO—NH$_2$, —NH—C(═O)—NH—($C_1$-$C_6$)alkyl, —NH—C(═O)-(5- to 12-membered)aryl, —NH—C(═O)—($C_1$-$C_6$)alkyl-(5- to 12-membered)aryl, —NH—($C_1$-$C_6$)alkyl-CO—$OR^7$, —NH—C(═O)—($C_1$-$C_6$)alkyl-CO—$OR^7$, —NH—C(═O)—CH(NH$_2$)—($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)$NR^5R^6$, —NH—($C_1$-$C_6$)alkylC(O)—$NR^5R^6$, —C(O)NH—($C_1$-$C_6$)alkyl-$COOR^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

or a pharmaceutically acceptable salt or solvate thereof.

The present invention also provides compounds of Formula IV or Formula V:

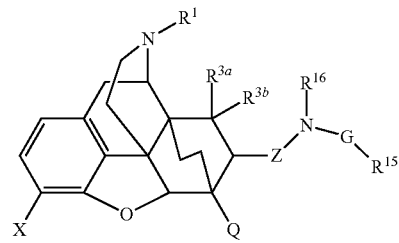

(IV)

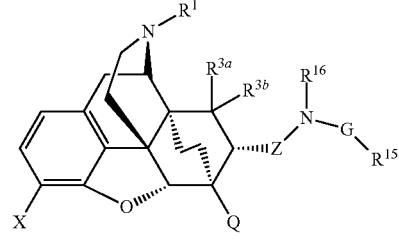

(V)

wherein

G is selected from the group consisting of carbonyl C(═O), sulfonyl S(═O)$_2$, and sulfinyl S(═O);

Q is selected from the group consisting of OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O), —($C_1$-$C_6$)alkyl, —(OCH$_2$CH$_2$), —OH, —O(C═O)$R^9$, —O—($C_1$-$C_6$)alkyl-$COOR^7$, —NH—($C_1$-$C_6$)alkyl-$COOR^7$, —O—C(O)—($C_1$-$C_6$)alkyl-C(O)$OR^7$, —NH—C(O)—($C_1$-$C_6$)alkyl-C(O)$OR^7$, —O—($C_1$-$C_6$)alkyl-C(O)$NR^9R^{10}$, —NH—($C_1$-$C_6$)alkyl-C(O)$NR^9R^{10}$, —O—C(O)—($C_1$-$C_6$)alkyl-C(O)$NR^9R^{10}$, —NH—C(O)—($C_1$-$C_6$)alkyl-C(O)$NR^9R^{10}$ and $R^{14}$; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-$COOR^7$, —$COOR^7$, $NH_2$, —NH($C_1$-$C_6$)alkyl, —$NR^9R^{10}$, —CN, —$OR^4$, —$CONR^9R^{10}$, —$NR^9COR^{10}$, —$SR^{11}$, -(3- to 12-membered)carbocyclic ring, -(5- to 12-membered)heterocycle, phenyl, and benzyl;

X is selected from the group consisting of OH, hydroxy($C_1$-$C_6$)alkyl-, dihydroxy($C_1$-$C_6$)alkyl-, halogen, —$NH_2$, —$NR^{20}$(C═O)$R^{12}$, —$CONR^{12}R^{13}$, —($C_1$-$C_6$)alkyl-$CONH_2$, —($C_1$-$C_6$)alkyl-COOH, —COOH, —O—($C_1$-$C_6$)alkyl-COOH, —O—($C_1$-$C_6$)alkyl-$CONH_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$), —OH, —(CH$_2$)$_p$CHOHCH$_2$OH, CN, —NH—SO$_2R^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-; any of which may optionally be substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

Z is —(CH$_2$)$_m$—, optionally substituted with 1 or 2-($C_1$-$C_6$)alkyl;

m is an integer 1, 2, 3, 4, 5, or 6;

p is an integer 0, 1 or 2;

s is an integer 1, 2, 3, 4, 5, 6, 7, 8, 9, 10, 11, 12, or 13;

R$^1$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

R$^{3a}$ and R$^{3b}$ are each independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; or R$^{3a}$ and R$^{3b}$ together form (=O);

R$^4$ is selected from the group consisting of —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^5$ and R$^6$ are each independently the group consisting of hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, and ($C_1$-$C_6$)alkyl-CONH—; or R$^5$ and R$^6$ together with the nitrogen atom to which they are attached form a (4- to 8-membered)heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

R$^7$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

R$^9$ and R$^{10}$ are each independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, and (($C_3$-$C_{12}$)cycloalkenyl)-($C_1$-$C_6$)alkyl-;

each R$^{11}$ is independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, and (($C_4$-$C_{12}$)cycloalkenyl)-($C_1$-$C_6$)alkyl-;

R$^{12}$ and R$^{13}$ are each independently selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$), —O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{14}$ is selected from the group consisting of —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, and ($C_1$-$C_6$)alkyl-CONH—;

$R^{15}$ is selected from the group consisting of $R^{20}$, $R^{21}$ and $R^{22}$;

$R^{16}$ is selected from the group consisting of hydrogen, —$(C_1$-$C_6)$alkyl, —$(C_2$-$C_6)$alkenyl, —$(C_2$-$C_6)$alkynyl, —$(C_1$-$C_{10})$alkoxy, —C(=O)—$(C_1$-$C_6)$alkyl, —$(C_3$-$C_{12})$cycloalkyl, (($C_3$-$C_{12})$cycloalkenyl, (($C_3$-$C_{12})$cycloalkyl)-$(C_1$-$C_6)$alkyl-, (($C_3$-$C_{12})$cycloalkenyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, and ((3- to 12-membered)heterocycle)-$(C_1$-$C_6)$alkyl; any of which is optionally substituted with 1 or 2 substituents independently selected from the group consisting of —$(C_1$-$C_6)$alkyl, OH, halo, —C(halo)$_3$, —CH(halo)$_2$, —CH$_2$(halo), —$(C_1$-$C_6)$alkyl-COOR$^7$, —COOR$^7$, NH$_2$, —NH$(C_1$-$C_6)$alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

$R^{20}$ is selected from the group consisting of hydrogen, —$(C_1$-$C_{10})$alkyl, —$(C_2$-$C_{12})$alkynyl, —$(C_1$-$C_{10})$alkoxy, —(OCH$_2$CH$_2$)$_s$—O$(C_1$-$C_6)$alkyl, —(CH$_2$CH$_2$O)$_s$—$(C_1$-$C_6)$alkyl, CN, —CONR$^5$R$^6$, —$(C_1$-$C_6)$alkyl-CO—NR$^5$R$^6$, —COOR$^7$, —$(C_1$-$C_6)$alkyl-CO—OR$^7$, —$(C_1$-$C_6)$alkoxy-COOR$^7$, —$(C_3$-$C_{12})$cycloalkyl, (($C_3$-$C_{12})$cycloalkyl)-$(C_1$-$C_6)$alkyl-, —$(C_4$-$C_{12})$cycloalkenyl, (($C_4$-$C_{12})$cycloalkenyl)-$(C_1$-$C_6)$alkyl-, —$(C_6$-$C_{14})$bicycloalkyl, (($C_6$-$C_{14})$bicycloalkyl)-$(C_1$-$C_6)$alkyl-, —$(C_8$-$C_{20})$tricycloalkyl, (($C_8$-$C_{20})$tricycloalkyl)-$(C_1$-$C_6)$alkyl-, —$(C_7$-$C_{14})$bicycloalkenyl, (($C_7$-$C_{14})$bicycloalkenyl)-$(C_1$-$C_6)$alkyl-, —$(C_8$-$C_{20})$tricycloalkenyl, (($C_8$-$C_{20})$tricycloalkyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl and naphthyl; each of which is optionally substituted with one or two substituents independently selected from the group consisting of —OH, (=O), halo, —C(halo)$_3$, —CH(halo)$_2$, —CH$_2$(halo), $(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$alkyl-, —$(C_1$-$C_6)$alkoxy, (($C_1$-$C_6)$alkoxy)CO$(C_1$-$C_6)$alkoxy-, phenyl, benzyl, —NH$_2$, —NH$(C_1$-$C_6)$alkyl, —$(C_1$-$C_6)$alkyl-NH$(C_1$-$C_6)$alkyl-R$^{14}$, —CN, —SH, —OR$^4$, —CONR$^5$R$^6$, —$(C_1$-$C_6$alkyl)-CO—NR$^5$R$^6$, —COOR$^7$, —$(C_1$-$C_6)$alkyl-CO—OR$^7$, —$(C_1$-$C_6)$alkoxy-COOR$^7$, —(OCH$_2$CH$_2$)$_s$—O$(C_1$-$C_6)$alkyl, —(CH$_2$CH$_2$O)$_s$—$(C_1$-$C_6)$alkyl, (($C_1$-$C_6)$alkyl)sulfonyl$(C_1$-$C_6)$alkyl-, —NH—SO$_2$$(C_1$-$C_6)$alkyl, —N(SO$_2$$(C_1$-$C_6)$alkyl)$_2$, —C(=NH)NH$_2$, —NH—CO—$(C_1$-$C_6)$alkyl, —NH—CO—NH$_2$, —NH—C(=O)—NH—$(C_1$-$C_6)$alkyl, —NH—C(=O)-(5- to 12-membered)aryl, —NH—C(=O)—$(C_1$-$C_6)$alkyl-(5- to 12-membered)aryl, —NH—$(C_1$-$C_6)$alkyl-CO—OR$^7$, —NH—C(=O)—$(C_1$-$C_6)$alkyl-CO—OR$^7$, —NH—C(=O)—CH(NH$_2$)—$(C_1$-$C_6)$alkyl-CO—OR$^7$, —$(C_3$-$C_{12})$cycloalkyl, (($C_3$-$C_{12})$cycloalkyl)-$(C_1$-$C_6)$alkyl-, -(5- to 12-membered)aryl, -(5- to 12-membered)aryloxy, —$(C_1$-$C_6)$alkoxyC(O)NR$^5$R$^6$, —NH—$(C_1$-$C_6)$alkylC(O)—NR$^5$R$^6$, —C(O)NH—$(C_1$-$C_6)$alkyl-COOR$^7$, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{22}$ is an amino group unsubstituted or substituted one or two times with substituents independently selected from the group consisting of —$(C_1$-$C_{10})$alkyl, —$(C_2$-$C_{12})$alkenyl, —$(C_3$-$C_{12})$cycloalkyl, (($C_3$-$C_{12})$cycloalkyl)-$(C_1$-$C_6)$alkyl-, -(5- to 12-membered)aryl (e.g. phenyl or naphthyl), ((5- to 12-membered)aryl)-$(C_1$-$C_6)$alkyl- (e.g. benzyl), -(5- to 12-membered)heteroaryl, ((5- to 12-membered)heteroaryl)-$(C_1$-$C_6)$alkyl-, -(3- to 12-membered)heterocycle, or ((3- to 12 membered)heterocycle)-$(C_1$-$C_6)$alkyl-; each of which is optionally substituted with 1 or 2 substituents independently selected from the group consisting of —$(C_1$-$C_6)$alkyl, OH, halo, —C(halo)$_3$, —CH(halo)$_2$, —CH$_2$(halo), —$(C_1$-$C_6)$alkyl-COOR$^7$, —COOR$^7$, NH$_2$, —NH$(C_1$-$C_6)$alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, and -(5- to 12-membered)heterocycle;

$R^{21}$ is $R^{20}$ or an alpha-amino compound of structure:

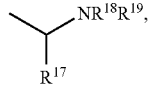

wherein each $R^{17}$ is independently selected from the group consisting of hydrogen, —$(C_1$-$C_{10})$alkyl, —$(C_2$-$C_{10})$alkenyl, —$(C_2$-$C_{10})$alkynyl, —$(C_1$-$C_{10})$alkoxy, OH, hydroxy$(C_1$-$C_6)$alkyl-, —C(halo)$_3$, —CH(halo)$_2$, —CH$_2$(halo), —$(C_1$-$C_6)$alkyl-C(=O)—$(C_1$-$C_6)$alkoxy, —$(C_1$-$C_6)$alkoxy-C(=O)—$(C_1$-$C_6)$alkyl, —$(C_1$-$C_6)$alkyl-CN, —$(C_1$-$C_6)$alkyl-COOR$^7$, —$(C_1$-$C_6)$alkyl-CN, —$(C_1$-$C_6)$alkyl-CONR$^9$R$^{10}$, —$(C_1$-$C_6)$alkoxy-COOR$^7$, —$(C_3$-$C_{12})$cycloalkyl, (($C_3$-$C_{12})$cycloalkyl)-$(C_1$-$C_6)$alkyl-, (($C_3$-$C_{12})$cycloalkyl)-$(C_1$-$C_6)$alkoxy-, (($C_3$-$C_{12})$cycloalkyl)-$(C_1$-$C_6)$alkoxy-$(C_1$-$C_6)$alkyl-, —$(C_4$-$C_{12})$cycloalkenyl, (($C_4$-$C_{12})$cycloalkenyl)-$(C_1$-$C_6)$alkyl-, (($C_4$-$C_{12})$cycloalkenyl)-$(C_1$-$C_6)$alkoxy-, (($C_4$-$C_{12})$cycloalkenyl)-$(C_1$-$C_6)$alkoxy-$(C_1$-$C_6)$alkyl-, -(5- to 12-membered)aryl, ((5- to 12-membered)aryl)-$(C_1$-$C_6)$alkyl-, ((5- to 12-membered)aryl)-$(C_1$-$C_6)$alkoxy-, ((5- to 12-membered)aryl)-$(C_1$-$C_6)$alkoxy-$(C_1$-$C_6)$alkyl-, -(5- to 12-membered)heteroaryl, ((5- to 12-membered)heteroaryl)-$(C_1$-$C_6)$alkyl-, ((5- to 12-membered)heteroaryl)-$(C_1$-$C_6)$alkoxy-, ((5- to 12-membered)heteroaryl)-$(C_1$-$C_6)$alkoxy-$(C_1$-$C_6)$alkyl-, -(3- to 12-membered)heterocycle, ((3- to 12 membered)heterocycle)-$(C_1$-$C_6)$alkyl-, ((3- to 12 membered)heterocycle)-$(C_1$-$C_6)$alkoxy-, and ((3- to 12 membered)heterocycle)-$(C_1$-$C_6)$alkoxy-$(C_1$-$C_6)$alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —$(C_1$-$C_6)$alkyl, OH, halo, —C(halo)$_3$, —CH(halo)$_2$, —CH$_2$(halo), $(C_1$-$C_6)$alkyl-COOR$^7$, —COOR$^7$, NH$_2$, —NH$(C_1$-$C_6)$alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and $R^{18}$ and $R^{19}$ are each independently selected from the group consisting of hydrogen, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_3$-$C_{12})$cycloalkenyl, (($C_3$-$C_{12})$cycloalkyl)-$(C_1$-$C_6)$alkyl-, (($C_3$-$C_{12})$cycloalkenyl)-$(C_1$-$C_6)$alkyl-, and —C(=O)—$(C_1$-$C_6)$alkyl; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), ($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or R$^{19}$ may optionally be a peptide-forming moiety having the structure

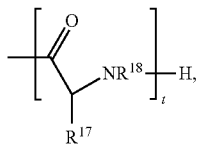

where t is an integer 1, 2 or 3;

provided that 1) when R$^1$ is cyclopropylmethyl, G is C=O, Q and X are both —OCH$_3$, Z is —CH$_2$—, R$^{15}$ is —CH(NH$_2$) CH$_3$, and R$^{16}$ is hydrogen, then either:

a) at least one of R$^{3a}$ and R$^{3b}$ is a substituent other than hydrogen; or b) at least one of R$^{18}$ and R$^{19}$ is a substituent other than hydrogen;

2) when R$^1$ is cyclopropylmethyl, G is S(=O)$_2$, X and Q are both —OCH$_3$, Z is —CH$_2$—, R$^{15}$ is —CH$_3$, and R$^{16}$ is benzyl, then at least one of R$^{3a}$ and R$^{3b}$ is a substituent other than hydrogen; and 3) when R$^1$ is cyclopropylmethyl, G is C=O, Q and X are both —OCH$_3$, Z is —CH$_2$—, R$^{15}$ is R$^{20}$, and R$^{20}$ is unsubstituted —($C_1$-$C_{10}$)alkyl, then R$^{16}$ is hydrogen;

or a pharmaceutically acceptable salt or solvate thereof.

In certain embodiments, the present invention provides compounds of Formula IV or Formula V, wherein, in addition or as an alternative to the above proviso 3), the proviso 3') applies that when R$^1$ is cyclopropylmethyl, G is C(=O), X and Q are both —OCH$_3$, Z is —CH$_2$—, R$^{15}$ is —CH$_3$, and R$^{16}$ is benzyl, then at least one of R$^{3a}$ and R$^{3b}$ is a substituent other than hydrogen.

Structural moiety G appears in Formulas I, IA, IB, IV and V above. In some embodiments G is carbonyl, C(=O). In other embodiments G is sulfonyl, S(=O)$_2$. In still other embodiments G is sulfinyl, S(=O).

Certain embodiments of Formula I or IA provide that when R$^1$ is cyclopropylmethyl, G is C=O, Q and X are both —OCH$_3$, Z is —CH$_2$—, R$^{15}$ is R$^{20}$, and R$^{20}$ is unsubstituted —($C_1$-$C_{10}$)alkyl, then R$^{16}$ is hydrogen.

Alternative embodiments of Formula I and IA provide that when R$^1$ is cyclopropylmethyl, G is C(=O), X and Q are both —OCH$_3$, Z is —CH$_2$—, R$^{15}$ is —CH$_3$, and R$^{16}$ is benzyl, then at least one of R$^{3a}$ and R$^{3b}$ is a substituent other than hydrogen.

Thus, certain embodiments of Formula I and IA provide that when R$^1$ is cyclopropylmethyl, G is C=O, Q and X are both —OCH$_3$, Z is —CH$_2$—, R$^{15}$ is R$^{20}$, and R$^{20}$ is unsubstituted —($C_1$-$C_{10}$)alkyl, then R$^{16}$ is hydrogen, or that when R$^1$ is cyclopropylmethyl, G is C(=O), X and Q are both —OCH$_3$, Z is —CH$_2$—, R$^{15}$ is —CH$_3$, and R$^{16}$ is benzyl, then at least one of R$^{3a}$ and R$^{3b}$ is a substituent other than hydrogen.

Separate embodiments of Formula I or IA provide that R$^{15}$ is R$^{20}$, and R$^{20}$ is selected from those defined in Formula I or IA, provided that R$^{20}$ is a moiety other than substituted or unsubstituted —($C_2$-$C_{12}$)alkenyl.

Substituent Q appears in all Formulas above. In some embodiments, Q is selected from the group consisting of —OH, —($C_1$-$C_{10}$)alkoxy, -(5- to 12-membered)aryl, ((C$_3$-C$_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —O—C(O)—($C_1$-$C_6$)alkyl-C(O)OR$^7$, —O—($C_1$-$C_6$)alkyl, —C(O)NR$^9$R$^{10}$, —C(O)—($C_1$-$C_6$)alkyl-C(O)NR$^9$R$^{10}$, and R$^{14}$. For example, Q is —(OCH$_2$CH$_2$)$_s$—O($C_1$-$C_6$)alkyl, —(CH$_2$CH$_2$O)$_s$—($C_1$-$C_6$)alkyl, or —(OCH$_2$CH$_2$)$_s$—OH and s is selected from 1, 2, 3, 4, 5, 6, or 7 in some embodiments. In other embodiments, Q is (OCH$_2$CH$_2$)$_5$OCH$_3$ or (OCH$_2$CH$_2$)$_3$OCH$_3$. In still other embodiments, Q is -(5- to 12-membered)aryl. In still other embodiments, Q is —O—CH$_2$—COOH, —NH—CH$_2$—COOH, —O—C(O)—CH$_2$—C(O)OH, or —NH—C(O)—CH$_2$—C(O)OH.

In certain embodiments, Q carries an optional substituent. For example —($C_1$-$C_6$)alkyl, ($C_1$-$C_{10}$)alkoxy, and -(5- to 12-membered)aryl are among the Q groups that can easily carry 1 or 2 additional substituents, such as, but not limited to, NH$_2$, —CH$_3$, —CH$_2$CH$_3$, —OH, halogen, etc.

For example, in certain specific embodiments Q is:
—OH or ($C_1$-$C_{10}$)alkoxy, such as OCH$_3$;
-(5- to 12-membered)aryl or ((5- to 12-membered)aryl)-($C_1$-$C_6$)alkyl-, such as benzyl or phenyl;
—(OCH$_2$CH$_2$)$_s$—O($C_1$-$C_6$)alkyl, or —(CH$_2$CH$_2$O)$_s$—($C_1$-$C_6$)alkyl;
—(OCH$_2$CH$_2$)$_s$—OH;
—O(C=O)R$^9$, or —O—($C_1$-$C_6$)alkyl; or
—C(O)NR$^9$R$^{10}$ or —O—C(O)—($C_1$-$C_6$)alkyl-C(O) NR$^9$R$^{10}$.

Substituent X appears in all Formulas above. In some embodiments, X is —OH, hydroxy($C_1$-$C_6$)alkyl-, or dihydroxy($C_1$-$C_6$)alkyl-. In another embodiment, X is halogen, such as Cl, F or Br. In still other embodiments, X is —NH$_2$, or —NR$^2$(C=O)R$^{12}$. In other embodiments, X is CONR$^{12}$R$^{13}$ or —($C_1$-$C_6$)alkyl-CONH$_2$. X is —($C_1$-$C_6$)alkyl-COOH, —COOH, or —O—($C_1$-$C_6$)alkyl-COOH in some embodiments, while in others X is —O—($C_1$-$C_6$)alkyl-CONH$_2$. Embodiments of X may include unsaturated hydrocarbons such as —($C_2$-$C_{10}$)alkenyl or —($C_2$-$C_{10}$)alkynyl. Embodiments of X may include oxygenated substituents, such as —($C_1$-$C_{10}$)alkoxy, —(OCH$_2$CH$_2$)$_s$—O($C_1$-$C_6$)alkyl, —(OCH$_2$CH$_2$)$_s$—OH, or —(CH$_2$)$_p$CHOHCH$_2$OH.

Some embodiments of X are carbocyclic or heterocyclic rings, with or without an alkyl or alkoxy tether. For example, in some embodiments, X is —(C$_3$-C$_{12}$)cycloalkyl, or ((C$_3$-C$_{12}$)cycloalkyl)-($C_1$-$C_6$)alkyl-. In other embodiments, X is -(5- to 12-membered)aryl or ((5- to 12-membered)aryl)-($C_1$-$C_6$)alkyl-. In still other cyclic embodiments, X is -(5- to 12-membered)heteroaryl, ((5- to 12-membered)heteroaryl)-($C_1$-$C_6$)alkyl, -(3- to 12-membered)heterocycle, or ((3- to 12-membered)heterocycle)-($C_1$-$C_6$)alkyl-.

For example, in certain specific embodiments X is:
—OH;
—CN;
—NH—SO$_2$R$^9$;
—($C_1$-$C_6$)alkoxy;
—OCH$_3$;
-halogen, such as F, or Br or Cl;
—NH$_2$;
—NR$^2$(C=O)R$^8$ or
—CONR$^2$R$^8$.

Structural moiety Z appears in Formulas I, IA, IV and V above. In some embodiments, Z is substituted. In other embodiments Z is unsubstituted. In some embodiments of Z, m is 1. In other embodiments m is 2, or 3. In one embodiment Z is unsubstituted and m is 1, i.e. —CH$_2$— or methylene.

Substituent $R^1$ appears in all Formulas above. In some embodiments, $R^1$ is hydrogen. In other embodiments, $R^1$ is —$(C_1-C_{10})$alkyl or —$(C_2-C_{12})$alkenyl, which may carry 1 or 2 optional substituents, such as —$(C_1-C_6)$alkyl, —OH, halo, —C(halo)$_3$, —COOR$^7$, NH$_2$, or —NH$(C_1-C_6)$alkyl, NR$^9$R$^{10}$. In other embodiments, $R^1$ is —$(C_3-C_{12})$cycloalkyl or $((C_3-C_{12})$cycloalkyl$)$-$(C_1-C_6)$alkyl-. In still other embodiments, $R^1$ is ((5- to 12-membered)aryl)-$(C_1-C_6)$alkyl-, ((5- to 12-membered)heteroaryl)-$(C_1-C_6)$alkyl-, or ((3- to 12 membered)heterocycle)-$(C_1-C_6)$alkyl-, any of which is optionally substituted with 1 or 2 substituents, for example, —$(C_1-C_6)$alkyl, —OH, halo, —C(halo)$_3$, —COOR$^7$, NH$_2$, —NH$(C_1-C_6)$alkyl, NR$^9$R$^{10}$ and SR$^{11}$.

For example, in certain specific embodiments $R^1$ is:
- —$(C_1-C_{10})$alkyl optionally substituted with 1, 2, or 3 substituents independently selected from the group consisting of —$(C_1-C_6)$alkyl, OH, halo, —C(halo)$_3$, —CH(halo)$_2$, —CH$_2$(halo), NH$_2$, NH$(C_1-C_6)$alkyl-, CN, SH, -(3- to 12-membered)carbocyclic ring, -(5- to 12-membered)heterocycle, phenyl, and benzyl;
- -methyl, -ethyl, or -isopropyl, and preferably methyl, each of which is optionally substituted with 1, 2, or 3 substituents independently selected from the group consisting of —$(C_1-C_6)$alkyl, OH, halo, —C(halo)$_3$, —CH(halo)$_2$, —CH$_2$(halo), NH$_2$, NH$(C_1-C_6)$alkyl-, CN, SH, -(3- to 12-membered)carbocyclic ring, -(5- to 12-membered)heterocycle, phenyl, and benzyl;
- —$(C_3-C_{12})$cycloalkyl optionally substituted with 1, 2, or 3 substituents independently selected from the group consisting of —$(C_1-C_6)$alkyl, OH, halo, —C(halo)$_3$, —CH(halo)$_2$, —CH$_2$(halo), NH$_2$, NH$(C_1-C_6)$alkyl-, CN, SH, -(3- to 12-membered)carbocyclic ring, -(5- to 12-membered)heterocycle, phenyl, and benzyl.

In another embodiment, $R^1$ is $((C_3-C_{12})$cycloalkyl$)$-$(C_1-C_6)$alkyl-, each of which is optionally substituted.

In another embodiment, $R^1$ is selected from the group consisting of cyclopropylmethyl, cyclobutylmethyl, cyclopentylmethyl, and cyclohexylmethyl, and preferably cyclopropylmethyl, each of which is optionally substituted.

In another embodiment, $R^1$ is -(5- to 12-membered)aryl, -(5- to 12-membered)heteroaryl, or -(3- to 12-membered)heterocycle, each of which is optionally substituted with 1, 2, or 3 substituents independently selected from the group consisting of —$(C_1-C_6)$alkyl, OH, halo, —C(halo)$_3$, —CH(halo)$_2$, —CH$_2$(halo), NH$_2$, NH$(C_1-C_6)$alkyl-, CN, SH, -(3- to 12-membered)carbocyclic ring, -(5- to 12-membered)heterocycle, phenyl, and benzyl.

Substituents $R^{3a}$ and $R^{3b}$ appear in Formulas I, IA, IV, and V above. In some embodiments, at least one of $R^{3a}$ or $R^{3b}$ is hydrogen; in other embodiments both $R^{3a}$ and $R^{3b}$ are hydrogen. In other embodiments, at least one of $R^{3a}$ or $R^{3b}$ is OH, while in other embodiments at least one of $R^{3a}$ or $R^{3b}$ is —$(C_1-C_6)$alkyl. In another embodiment, at least one of $R^{3a}$ or $R^{3b}$ is selected from the group consisting of methyl, ethyl and isopropyl.

In another embodiment, at least one of $R^{3a}$ and $R^{3b}$ is selected from the group consisting of —$(C_1-C_6)$alkyl-C(=O)—$(C_1-C_6)$alkoxy, —$(C_1-C_6)$alkyl-CN, —$(C_1-C_6)$alkyl-COOR$^7$, and ((5- to 12-membered)aryl)-$(C_1-C_6)$alkoxy-$(C_1-C_6)$alkyl-. In another embodiment, at least one of $R^{3a}$ and $R^{3b}$ is selected from the group consisting of CH$_2$CH$_2$C(O)OCH$_2$CH$_3$, CH$_2$CN, CH$_2$CH$_2$C(O)OH, and CH$_2$OCH$_2$C$_6$H$_5$.

In another embodiment, both $R^{3a}$ and $R^{3b}$ are —$(C_1-C_6)$alkyl. In another embodiment, at least one of $R^{3a}$ or $R^{3b}$ is —CH$_2$(halo). In another embodiment, at least one of $R^{3a}$ or $R^{3b}$ is selected from the group consisting of CH$_2$F and CH$_2$Cl.

Substituent $R^{15}$ appears in all Formulas above and is attached to G. In some embodiments, G is S(=O)$_2$ or S(=O) and $R^{15}$ is $R^{20}$ selected from the group consisting of —$(C_1-C_{10})$alkyl, —$(C_2-C_{12})$alkenyl, —$(C_2-C_{12})$alkynyl, —$(CH_2CH_2O)_s$—$(C_1-C_6)$alkyl, NH$_2$, —NH$(C_1-C_6)$alkyl, CN, —CONR$^5$R$^6$, —$(C_1-C_6)$alkyl-CO—NR$^5$R$^6$, —COOR$^7$, —$(C_1-C_6)$alkyl-CO—OR$^7$, —$(C_3-C_{12})$cycloalkyl, $((C_3-C_{12})$cycloalkyl$)$-$(C_1-C_6)$alkyl-, —$(C_4-C_{12})$cycloalkenyl, $((C_4-C_{12})$cycloalkenyl$)$-$(C_1-C_6)$alkyl-, —$(C_6-C_{14})$bicycloalkyl, $((C_6-C_{14})$bicycloalkyl$)$-$(C_1-C_6)$alkyl-, —$(C_8-C_{20})$tricycloalkyl, $((C_8-C_{20})$tricycloalkyl$)$-$(C_1-C_6)$alkyl-, —$(C_7-C_{14})$bicycloalkenyl, $((C_7-C_{14})$bicycloalkenyl$)$-$(C_1-C_6)$alkyl-, —$(C_8-C_{20})$tricycloalkenyl, $((C_8-C_{20})$tricycloalkenyl$)$-$(C_1-C_6)$alkyl-, -(5- to 12-membered)aryl, ((5- to 12-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl and naphthyl; each of which is optionally substituted with one or two substituents independently selected from the group consisting of OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, dihydroxy$(C_1-C_6)$alkyl-, —$(C_1-C_6)$alkoxy, $((C_1-C_6)$alkoxy$)$CO$(C_1-C_6)$alkoxy-, phenyl, benzyl, NH$_2$, —NH$(C_1-C_6)$alkyl, —$(C_1-C_6)$alkyl-NH$(C_1-C_6)$alkyl-R$^{14}$, CN, SH, OR$^4$, —CONR$^5$R$^6$, —$(C_1-C_6$alkyl$)$-CO—NR$^5$R$^6$, —COOR$^7$, —$(C_1-C_6)$alkyl-CO—OR$^7$, —$(C_1-C_6)$alkoxy-COOR$^7$, —$(OCH_2CH_2)_s$—O$(C_1-C_6)$alkyl, —$(CH_2CH_2O)_s$—$(C_1-C_6)$alkyl, $((C_1-C_6)$alkyl$)$sulfonyl$(C_1-C_6)$alkyl-, —NH—SO$_2$$(C_1-C_6)$alkyl, —N(SO$_2$$(C_1-C_6)$alkyl$)_2$, —C(=NH)NH$_2$, —NH—CO—$(C_1-C_6)$alkyl, —NH—CO—NH$_2$, —NH—C(=O)—NH—$(C_1-C_6)$alkyl, —NH—C(=O)-(5- to 12-membered)aryl, —NH—C(=O)—$(C_1-C_6)$alkyl-(5- to 12-membered)aryl, —NH—$(C_1-C_6)$alkyl-CO—OR$^7$, —NH—C(=O)—$(C_1-C_6)$alkyl-CO—OR$^7$, —NH—C(=O)—CH(NH$_2$)—$(C_1-C_6)$alkyl-CO—OR$^7$, —$(C_3-C_{12})$cycloalkyl, $((C_3-C_{12})$cycloalkyl$)$-$(C_1-C_6)$alkyl-, -(5- to 12-membered)aryl, -(5- to 12-membered)aryloxy, —$(C_1-C_6)$alkoxyC(O)NR$^5$R$^6$, —NH—$(C_1-C_6)$alkylC(O)—NR$^5$R$^6$, —C(O)NH—$(C_1-C_6)$alkyl-COOR$^7$, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-.

For example, in certain embodiments where G is S(=O)$_2$ or S(=O), $R^{15}$ is
- —$(C_1-C_{10})$alkyl unsubstituted;
- —$(C_1-C_{10})$alkyl substituted with 1, 2 or 3 substituents independently selected from the group consisting of —$(C_1-C_6)$alkyl, OH, halo, —C(halo)$_3$, —CH(halo)$_2$, —CH$_2$(halo), NH$_2$, NH$(C_1-C_6)$alkyl-, CN, SH, -(3- to 12-membered)carbocyclic ring, -(5- to 12-membered)heterocycle, phenyl, and benzyl;
- —$(C_2-C_{12})$alkenyl optionally substituted with 1 or 2 substituents independently selected from the group consisting of —$(C_1-C_6)$alkyl, OH, halo, —C(halo)$_3$, —CH(halo)$_2$, —CH$_2$(halo), NH$_2$, NH$(C_1-C_6)$alkyl-, CN, SH, -(3- to 12-membered)carbocyclic ring, -(5- to 12-membered)heterocycle, phenyl, and benzyl —($C_3$-$C_{12}$)cycloalkyl, optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, -(3- to 12-membered)carbocyclic ring, -(5- to 12-membered)heterocycle, phenyl, and benzyl (($C_3$-$C_{12}$)cycloalkyl)-($C_1$-$C_6$)alkyl- optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, -(3- to 12-membered)carbocyclic ring, -(5- to 12-membered)heterocycle, phenyl, and benzyl -(5- to 12-membered)aryl, optionally substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, and NH($C_1$-$C_6$)alkyl-;

((5- to 12-membered)aryl)-($C_1$-$C_6$)alkyl- optionally substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, and NH($C_1$-$C_6$)alkyl-;

In other embodiments, G is C(=O), and $R^{15}$ is selected from the group consisting of $R^{20}$, $R^{21}$ and $R^{22}$. Thus, when G is C(=O), additional options are possible for $R^{15}$. In some embodiments of Formula I or IA, $R^{15}$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-.

For example, in certain embodiments where G is C(=O), $R^{15}$ is

-hydrogen;

—($C_1$-$C_{10}$)alkyl unsubstituted, for example methyl, ethyl, or propyl;

—($C_1$-$C_{10}$)alkyl substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, -(3- to 12-membered)carbocyclic ring, -(5- to 12-membered)heterocycle, phenyl, and benzyl;

—($C_2$-$C_{12}$)alkenyl optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, -(3- to 12-membered)carbocyclic ring, -(5- to 12-membered)heterocycle, phenyl, and benzyl;

—($C_3$-$C_{12}$)cycloalkyl, optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, -(3- to 12-membered)carbocyclic ring, -(5- to 12-membered)heterocycle, phenyl, and benzyl;

(($C_3$-$C_{12}$)cycloalkyl)-($C_1$-$C_6$)alkyl- optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, -(3- to 12-membered)carbocyclic ring, -(5- to 12-membered)heterocycle, phenyl, and benzyl;

-(5- to 12-membered)aryl, optionally substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, and NH($C_1$-$C_6$)alkyl-;

—NH-(5- to 12-membered)aryl, optionally substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, and NH($C_1$-$C_6$)alkyl-;

((5- to 12-membered)aryl)-($C_1$-$C_6$)alkyl- optionally substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, and NH($C_1$-$C_6$)alkyl-;

—($C_1$-$C_{10}$)alkoxy;

—(OCH$_2$CH$_2$)$_s$—O($C_1$-$C_6$)alkyl;

—CONR$^5$R$^6$, —COOR$^7$, or —($C_1$-$C_6$)alkyl-CO—OR$^7$, —($C_1$-$C_6$)alkoxy-COOR$^7$; or -an alpha-amino compound of structure:

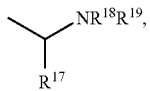

wherein $R^{17}$, $R^{18}$ and $R^{19}$ are as defined elsewhere herein.

In one embodiment of Formulas I, IA, IB, II, and III, $R^{15}$ is $R^{20}$, and $R^{20}$ is selected from those defined in Formula I or IA, provided that $R^{20}$ is a moiety other than substituted or unsubstituted —($C_2$-$C_{12}$)alkenyl.

Substituent $R^{16}$ appears in Formulas I, IA, IV and V above. In some embodiments, $R^{16}$ is hydrogen. In other embodiments, $R^{16}$ is —($C_1$-$C_6$)alkyl or —($C_2$-$C_6$)alkenyl, optionally substituted with 1 or 2 substituents independently selected from —($C_1$-$C_6$)alkyl, OH, halo, —C(halo)$_3$, —CH(halo)$_2$, —CH$_2$(halo), —COOR$^7$, NH$_2$, —NH($C_1$-$C_6$)alkyl, —NR$^9$R$^{10}$, —OR$^4$, —CONR$^9$R$^{10}$, —NR$^9$COR$^{10}$, —SR$^{11}$, -(3- to 12-membered)carbocyclic ring, -(5- to 12-membered) heterocycle, phenyl, and benzyl.

In some embodiments, $R^{16}$ is —C(=O)—($C_1$-$C_6$)alkyl, such as acetyl (ethanoyl) or propanoyl, or the like.

In some embodiments, $R^{16}$ is —($C_3$-$C_{12}$)cycloalkyl or (($C_3$-$C_{12}$)cycloalkyl)-($C_1$-$C_6$)alkyl-, while in other embodiments, $R^{16}$ is -(5- to 12-membered)aryl or ((5- to 12-membered)aryl)-($C_1$-$C_6$)alkyl-, -(5- to 12-membered)heteroaryl, or ((5- to 12-membered)heteroaryl)-($C_1$-$C_6$)alkyl-; in each case the rings may optionally be substituted with 1, 2 or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, —NH$_2$, —NH($C_1$-$C_6$)alkyl, —NR$^9$R$^{10}$), —CN, —OR$^4$, —CONR$^9$R$^{10}$NR$^9$COR$^{10}$, and —SR$^{11}$.

Substituent $R^{17}$ appears in the structure of an "alpha-amino compound" found among the options for $R^{15}$ via $R^{21}$ above, and also in the structure of a "peptide-forming moiety" found among the options for $R^{19}$ discussed below. By virtue of the peptide-forming moiety, $R^{17}$ may repeat. Each $R^{17}$ is independently selected from the group consisting of hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkyl-CN, —($C_1$-$C_6$)alkyl-CONR$^9$R$^{10}$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl.

In some embodiments, $R^{17}$ is hydrogen. In other embodiments, $R^{17}$ is —($C_1$-$C_{10}$)alkyl, optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl. In still other embodiments, $R^{17}$ is ((5- to 12-membered)aryl)-($C_1$-$C_6$)alkyl-, or ((5- to 12-membered)heteroaryl)-($C_1$-$C_6$)alkyl-, optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, and —SR$^{11}$.

For example, in certain specific embodiments $R^{17}$ is:
- —($C_1$-$C_{10}$)alkyl unsubstituted, for example methyl, ethyl, or propyl;
- —($C_1$-$C_{10}$)alkyl substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, SR$^{11}$, -(3- to 12-membered)carbocyclic ring, -(5- to 12-membered)heterocycle, phenyl, and benzyl;
- -methyl, ethyl, propyl, or butyl, optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, SH, SR$^{11}$, -(3- to 12-membered)carbocyclic ring, -(5- to 12-membered)heterocycle, phenyl, and benzyl;
- —($C_2$-$C_{12}$)alkenyl optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, -(3- to 12-membered)carbocyclic ring, -(5- to 12-membered)heterocycle, phenyl, and benzyl;
- (($C_3$-$C_{12}$)cycloalkyl)-($C_1$-$C_6$)alkyl- optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, CN, SH, or SR$^{11}$;
- -(5- to 12-membered)aryl, optionally substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, and NH($C_1$-$C_6$)alkyl-;
- ((5- to 12-membered)aryl)-($C_1$-$C_6$)alkyl- optionally substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, and NH($C_1$-$C_6$)alkyl-;
- -(5- to 12-membered)heteroaryl, ((5- to 12-membered)heteroaryl)-($C_1$-$C_6$)alkyl-, optionally substituted with 1, 2 or 3 substituents independently selected from the group consisting of —($C_1$-$C_6$)alkyl, OH, halo, —C(halo)$_3$, —CH(halo)$_2$, —CH$_2$(halo), NH$_2$, and NH($C_1$-$C_6$)alkyl-;
- -alkyl-acids, alkyl-esters or alkyl-amides like ($C_1$-$C_6$)alkyl-COOR$^7$ or —($C_1$-$C_6$)alkyl-CONR$^9$R$^{10}$, optionally substituted with 1 or 2 substituents independently selected from the group consisting of —($C_1$-$C_6$)alkyl, OH, halo, —C(halo)$_3$, —CH(halo)$_2$, —CH$_2$(halo), NH$_2$, NH(C$_1$-C$_6$)alkyl-, SH, SR$^{11}$, -(3- to 12-membered)carbocyclic ring, -(5- to 12-membered)heterocycle, phenyl, and benzyl;

hydroxy(C$_1$-C$_6$)alkyl-, optionally substituted with 1 or 2 substituents independently selected from the group consisting of —(C$_1$-C$_6$)alkyl, OH, halo, —C(halo)$_3$, —CH(halo)$_2$, —CH$_2$(halo), NH$_2$, and NH(C$_1$-C$_6$)alkyl-.

In another embodiment, R$^{17}$ taken together with R$^{18}$ or R$^{19}$ and the N to which they are attached may form a 3- to 12-membered heterocycle, which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl. Such heterocycles (unsubstituted) include, for example, thiazolidinyl, pyrrolidinyl, piperidinyl, and tetrahydrofuranyl.

Substituents R$^{18}$ and R$^{19}$ each appear in the structure of an "alpha-amino compound" found among the options for R$^{15}$ via R$^{21}$ above, and also in the structure of a "peptide-forming moiety" found among the options for R$^{19}$ discussed below. By virtue of the peptide-forming moiety, R$^{18}$ may also repeat. R$^{19}$ and each R$^{18}$ are independently selected from the group consisting of hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, ((C$_3$-C$_{12}$)cycloalkenyl)-(C$_1$-C$_6$)alkyl-, and —C(=O)—(C$_1$-C$_6$)alkyl; any of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; or R$^{19}$ may optionally be a peptide-forming moiety having the structure

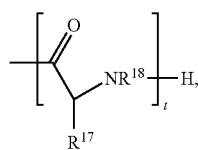

wherein t is an integer 1, 2 or 3; and wherein each R$^{17}$ is independently defined as above.

In some embodiments, R$^{19}$ and R$^{18}$ are both hydrogen; while in some embodiments at least one of R$^{19}$ and R$^{18}$ is hydrogen. In other embodiments, at least one of R$^{19}$ and R$^{18}$ is —(C$_1$-C$_6$)alkyl or —(C$_2$-C$_6$)alkenyl, optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl. In yet another embodiment, at least one of R$^{19}$ and R$^{18}$ is —C(=O)—(C$_1$-C$_6$)alkyl, such as acetyl (ethanoyl) or propanoyl, or the like.

In one embodiment, at least R$^{19}$ is a peptide-forming moiety having the structure

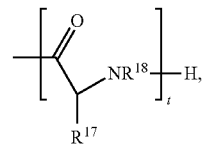

where t is an integer 1, 2 or 3; and wherein each R$^{17}$ is independently defined as above. In other such embodiments, t is 1 or 2. In still other such embodiments, each R$^{18}$ is independently hydrogen or —(C$_1$-C$_6$)alkyl.

In one embodiment, R$^{19}$ is a peptide-forming moiety having the structure

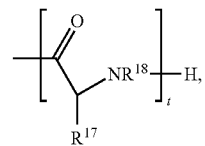

where t is an integer 1 or 2; and wherein each R$^{17}$ is independently selected from the group consisting of hydrogen, —(C$_1$-C$_6$)alkyl, hydroxy(C$_1$-C$_6$)alkyl-, ((5- to 12-membered)aryl)-(C$_1$-C$_6$)alkyl-, -(5- to 12-membered)heteroaryl, and ((5- to 12-membered)heteroaryl)-(C$_1$-C$_6$)alkyl-, optionally substituted with 1 or 2 substituents independently selected from the group consisting of —(C$_1$-C$_6$)alkyl, OH, NH$_2$, —SR$^{11}$, and —CONR$^9$R$^{10}$. In other such embodiments, each R$^{18}$ is independently hydrogen or —(C$_1$-C$_6$)alkyl In another embodiment, R$^{19}$ is a peptide-forming moiety having the structure

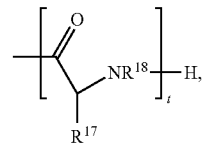

where t is an integer 1 or 2; and wherein at least one R$^{17}$ together with R$^{18}$ or R$^{19}$ and the N to which they are attached may form a 3- to 12-membered heterocycle.

In certain embodiments G is C(=O), Z is —CH$_2$—, R$^{3a}$, R$^{3b}$ and R$^{16}$ are all hydrogen (Formula II);

and R$^{15}$ is an alpha-amino compound of structure:

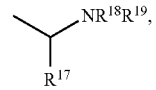

wherein:

R$^{17}$ is selected from the group consisting of hydrogen, (C$_1$-C$_{10}$)alkyl, OH, hydroxy(C$_1$-C$_6$)alkyl-, —(C$_1$-C$_6$)alkyl-CONR$^9$R$^{10}$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, and ((3- to 12 membered)heterocycle)-(C$_1$-C$_6$) alkyl-; or R$^{17}$ taken together with R$^{18}$ or R$^{19}$ and the N to which they are attached form a 3- to 12-membered heterocycle; any of which is optionally substituted with 1 or 2 substituents independently selected from the group consisting of —(C$_1$-C$_6$)alkyl, OH, halo, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and R$^{18}$ and R$^{19}$ are each independently hydrogen or —(C$_1$-C$_6$) alkyl.

In certain embodiments G is C(═O), Z is —CH$_2$—, R$^{3a}$, R$^{3b}$ and R$^{16}$ are all hydrogen (Formula II);
and R$^{15}$ is an alpha-amino compound of structure:

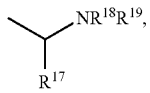

wherein:
R$^{17}$ is selected from the group consisting of hydrogen, —(C$_1$-C$_6$)alkyl, hydroxy(C$_1$-C$_6$)alkyl-, ((5- to 12-membered)aryl)-(C$_1$-C$_6$)alkyl-, -(5- to 12-membered)heteroaryl, and ((5- to 12-membered)heteroaryl)-(C$_1$-C$_6$)alkyl-; or R$^{17}$ together with R$^{18}$ or R$^{19}$ and the N to which they are attached may form a 3- to 12-membered heterocycle; any of which is optionally substituted with 1 or 2 substituents independently selected from the group consisting of —(C$_1$-C$_6$)alkyl, OH, NH$_2$, —SR$^{11}$, and —CONR$^9$R$^{10}$; and R$^{18}$ and R$^{19}$ are each independently hydrogen or —(C$_1$-C$_6$) alkyl.

In certain other embodiments G is C(═O), Z is —CH$_2$—, R$^{3a}$, R$^{3b}$ and R$^{16}$ are all hydrogen (Formula II);
and R$^{15}$ is an alpha-amino compound of structure:

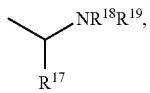

wherein:
R$^{17}$ is selected from the group consisting of hydrogen, —(C$_1$-C$_6$)alkyl, hydroxy(C$_1$-C$_6$)alkyl-, ((5- to 12-membered)aryl)-(C$_1$-C$_6$)alkyl-, -(5- to 12-membered)heteroaryl, and ((5- to 12-membered)heteroaryl)-(C$_1$-C$_6$)alkyl-; or R$^{17}$ together with R$^{18}$ or R$^{19}$ and the N to which they are attached may form a 3- to 12-membered heterocycle; any of which is optionally substituted with 1 or 2 substituents independently selected from the group consisting of —(C$_1$-C$_6$)alkyl, OH, NH$_2$, —SR$^{11}$, and —CONR$^9$R$^{10}$; and R$^{18}$ is hydrogen or —(C$_1$-C$_6$)alkyl; R$^{19}$ is a peptide-forming moiety having the structure

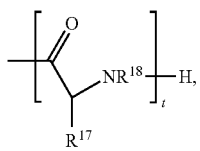

wherein t is an integer 1, 2 or 3.

In certain other embodiments G is C(═O), Z is —CH$_2$—, R$^{3a}$, R$^{3b}$ and R$^{16}$ are all hydrogen (Formula II);

and R$^{15}$ is selected from the group consisting of —(C$_1$-C$_{10}$) alkyl, —(C$_2$-C$_{12}$)alkenyl, —(C$_2$-C$_{12}$)alkynyl, —NH$_2$, —NH(C$_1$-C$_6$)alkyl, —CONR$^5$R$^6$, —(C$_1$-C$_6$)alkyl-CO—NR$^5$R$^6$, —(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(7- to 12-membered)bicyclic aryl, ((7- to 12-membered)bicyclic aryl)-(C$_1$-C$_6$) alkyl-, -(5- to 12-membered)heteroaryl, ((5- to 12-membered)heteroaryl)-(C$_1$-C$_6$)alkyl-, -(3- to 12-membered) heterocycle, ((3- to 12 membered)heterocycle)-(C$_1$-C$_6$) alkyl-, phenyl, benzyl and naphthyl; each of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$) alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl.

In some embodiments G is S(═O)$_2$, Z is —CH$_2$—, R$^{3a}$, R$^{3b}$ and R$^{16}$ are all hydrogen (Formula III); and R$^{15}$ is selected from the group consisting of —(C$_1$-C$_{10}$)alkyl, —(C$_2$-C$_{12}$) alkenyl, —(C$_2$-C$_{12}$)alkynyl, —NH$_2$, —NH(C$_1$-C$_6$)alkyl, —CONR$^5$R$^6$, —(C$_1$-C$_6$)alkyl-CO—NR$^5$R$^6$, —(C$_1$-C$_6$) alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(7- to 12-membered)bicyclic aryl, ((7- to 12-membered)bicyclic aryl)-(C$_1$-C$_6$) alkyl-, -(5- to 12-membered)heteroaryl, ((5- to 12-membered)heteroaryl)-(C$_1$-C$_6$)alkyl-, -(3- to 12-membered) heterocycle, ((3- to 12 membered)heterocycle)-(C$_1$-C$_6$) alkyl-, phenyl, benzyl or naphthyl; each of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl.

In some other embodiments G is S(═O) or S(═O)$_2$, Z is —CH$_2$—, R$^{3a}$, R$^{3b}$ and R$^{16}$ are all hydrogen;
and R$^{15}$ is selected from —(C$_1$-C$_{10}$)alkyl, —(C$_2$-C$_{12}$)alkenyl, —(C$_2$-C$_{12}$)alkynyl, —NH$_2$, —NH(C$_1$-C$_6$)alkyl, —CONR$^5$R$^6$, —(C$_1$-C$_6$)alkyl-CO—NR$^5$R$^6$, —(C$_1$-C$_6$) alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(7- to 12-membered)bicyclic aryl, ((7- to 12-membered)bicyclic aryl)-(C$_1$-C$_6$) alkyl-, -(5- to 12-membered)heteroaryl, ((5- to 12-membered)heteroaryl)-(C$_1$-C$_6$)alkyl-, -(3- to 12-membered) heterocycle, ((3- to 12 membered)heterocycle)-(C$_1$-C$_6$) alkyl-, phenyl, benzyl or naphthyl; each of which is optionally substituted with 1 or 2 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl.

In some other embodiments G is S(═O) or S(═O)$_2$, Z is —CH$_2$—, R$^{3a}$, R$^{3b}$ and R$^{16}$ are all hydrogen; and R$^{15}$ is selected from —(C$_1$-C$_{10}$)alkyl, —(C$_2$-C$_{12}$)alkenyl, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$) alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, benzyl or naphthyl; each of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl.

In some embodiments of structures IV and V, R$^{22}$ may be an amino group substituted one or two times with —($C_1$-$C_{10}$)alkyl, —($C_2$-$C_{12}$)alkenyl, —($C_3$-$C_{12}$)cycloalkyl, (($C_3$-$C_{12}$)cycloalkyl)-($C_1$-$C_6$)alkyl-, -(5- to 12-membered)aryl (e.g. phenyl or naphthyl), ((5- to 12-membered)aryl)-($C_1$-$C_6$)alkyl- (e.g. benzyl), -(5- to 12-membered)heteroaryl, ((5- to 12-membered)heteroaryl)-($C_1$-$C_6$)alkyl-, -(3- to 12-membered)heterocycle, or ((3- to 12 membered)heterocycle)-($C_1$-$C_6$)alkyl-; each of which is optionally substituted with 1 or 2 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered) carbocyclic ring, and -(5- to 12-membered)heterocycle.

In some embodiments, when R$^1$ is cyclopropylmethyl, G is C=O, Q and X are both —OCH$_3$, Z is —CH$_2$—, and R$^{3a}$, R$^{3b}$ and R$^{16}$ are all hydrogen, then either:

a) R$^{15}$ is a substituent other than —CH(NH$_2$)CH$_3$; or b) at least one of R$^{18}$ and R$^{19}$ is a substituent other than hydrogen.

In some embodiments, when R$^1$ is cyclopropylmethyl, G is S(=O)$_2$, Q is —OCH$_3$, X is OCH$_3$ or OH, Z is —CH$_2$—, R$^{3a}$ and R$^{3b}$ are both hydrogen, then either:

a) R$^{15}$ is a substituent other than —CH$_3$; or b) R$^{16}$ is a substituent other than benzyl.

Specific compounds of the invention include:

(S)-2-amino-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)propanamide;

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-phenylpropanamide;

(2S,3S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-methylpentanamide;

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)propanamide;

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-hydroxypropanamide;

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-4-methylpentanamide;

(S)-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)pyrrolidine-2-carboxamide;

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(4-hydroxyphenyl)propanamide;

(S)-3-amino-4-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)amino)-4-oxobutanoic acid;

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(1H-imidazol-4-yl)propanamide;

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)propanamide;

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-phenylpropanamide;

2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)acetamide;

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(4-hydroxyphenyl)propanamide;

(2S,3S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-methylpentanamide;

(S)-1-acetyl-N-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)pyrrolidine-2-carboxamide;

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(1H-imidazol-4-yl)propanamide;

2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)acetamide;

(S)-3-acetamido-4-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)amino)-4-oxobutanoic acid;

(S)-2-acetamido-N$^1$-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)succinamide;

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-4-methylpentanamide;

(S)-2-amino-N$^1$-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)succinamide;

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-hydroxypropanamide; and N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-1H-indole-3-carboxamide.

Specific compounds of the invention further include:

4-((((4R,4aS,6R,7R,7aR,12bS)-3-(cyclopropylmethyl)-9-hydroxy-7-methoxy-1,2,3,4,5,6,7,7a-octahydro-4a,7- ethano-4,12-methanobenzofuro[3,2-e]isoquinolin-6-yl)methyl)amino)-4-oxobutanoic acid;

N1-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)succinamide;

6-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)amino)-6-oxohexanoic acid;

N1-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)adipamide;

3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)carbamoyl)pyrazine-2-carboxylic acid;

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)pyrazine-2,3-dicarboxamide;

2-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)carbamoyl)benzoic acid;

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(1H-tetrazol-5-yl)propanamide;

1-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-phenylurea; and 1-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(m-tolyl)urea.

Specific compounds of the invention further include:

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-4-methylbenzenesulfonamide;

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-benzenesulfonamide;

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-1,1,1-trifluoromethanesulfonamide; and N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)methanesulfonamide.

Compounds of the Invention encompass all salts of the disclosed compounds of the above formulas. The present invention preferably includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicylohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

Compounds of the Invention also encompass solvates of the disclosed compounds of any one of the above formulas. The term "solvate" as used herein is a combination, physical association and/or solvation of a compound of Formula I, Formula IA, or Formula IB with a solvent molecule such as, e.g. a disolvate, monosolvate or hemisolvate, where the ratio of solvent molecule to a compound of any one of the above formulas, is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A compound of any one of the above formulas may be present as a solvated form with a pharmaceutically acceptable solvent, such as water, methanol, ethanol, and the like, and it is intended that the invention includes both solvated and unsolvated forms of compounds of any one of the above formulas. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.*, 603-604 (2001). A typical, non-limiting, process of preparing a solvate would involve dissolving a compound of any one of the above formulas in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides the use of a Compound of the Invention in the manufacture of a medicament for treating or preventing a Condition. In one embodiment, the Condition is pain, such as acute or chronic pain. In one embodiment, a Compound of the Invention has agonist activity at the μ, δ and/or κ receptors. In another embodiment a Compound of the Invention has agonist activity at the μ receptor. In another embodiment, a Compound of the Invention has antagonist activity at the ORL-1 receptor. In another embodiment, certain Compounds of the invention can stimulate one receptor (e.g., a μ, δ and/or κ agonist) and inhibit a different receptor (e.g., an ORL-1 antagonist). In another embodiment, the Compound of the Invention is an agonist at the μ receptor, and an antagonist at the ORL-1 receptor.

Definitions And Glossary

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including books, journal articles, published U.S. or foreign patent applications, issued U.S. or foreign patents, and any other references, are each incorporated by reference in their entireties, including all data, tables, figures, and text presented in the cited references.

As used herein, the term "—$(C_1-C_6)$alkyl" refers to straight-chain and branched non-cyclic saturated hydrocarbons having 1, 2, 3, 4, 5, or 6 carbon atoms. Representative straight chain —$(C_1-C_6)$alkyl groups include methyl, -ethyl, -n-propyl, -n-butyl, -n-pentyl, and -n-hexyl. Representative branched-chain —$(C_1-C_6)$alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like.

More generally, the subscript refers to the number of carbon atoms in the chain. Thus, the term "—$(C_1-C_{10})$alkyl" refers to straight-chain and branched non-cyclic saturated hydrocarbons having 1, 2, 3, 4, 5, 6, 7, 8, 9 or 10 carbon atoms. Representative straight chain —$(C_1-C_{10})$ alkyl groups include, in addition to $C_1-C_6$ alkyl groups mentioned above, include n-heptyl, n-octyl, n-nonyl and n-decyl (as straight chains) and 5-methylhexyl, 6-methylheptyl, and the like (as branched chains). In like manner, "—$(C_2-C_{10})$alkyl" refers to straight-chain and branched non-cyclic saturated hydrocarbons having from 2 to 10 carbon atoms (thereby excluding methyl).

As used herein, the term "—$(C_2-C_{12})$alkenyl" refers to straight chain and branched non-cyclic hydrocarbons having 2, 3, 4, 5, 6, 7, 8, 9, 10, 11 or carbon atoms and including at least one carbon-carbon double bond. Representative straight chain and branched —$(C_2-C_{12})$alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

As used herein, the term "—$(C_2-C_6)$alkenyl" refers to straight chain and branched non-cyclic hydrocarbons having from 2 to 6 carbon atoms and including at least one carbon-carbon double bond. Representative straight chain and branched —$(C_2-C_6)$alkenyl groups include -vinyl, allyl, -1-butenyl, -2-butenyl, -isobutylenyl, -1-pentenyl, -2-pentenyl, -3-methyl-1-butenyl, -2-methyl-2-butenyl, and the like.

As used herein, the term "—$(C_2-C_{12})$alkynyl" refers to straight chain and branched non-cyclic hydrocarbons having from 2 to 12 carbon atoms and including at least one carbon-carbon triple bond. Representative straight chain and branched —$(C_2-C_{12})$alkynyl groups include -acetylenyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

As used herein, the term "—$(C_2-C_6)$alkynyl" refers to straight chain and branched non-cyclic hydrocarbons having from 2 to 6 carbon atoms and including at least one carbon-carbon triple bond. Representative straight chain and branched $(C_2-C_6)$alkynyl groups include -acetylenyl, -propynyl, -1 butynyl, -2-butynyl, -1-pentynyl, -2-pentynyl, -3-methyl-1-butynyl, -4-pentynyl, and the like.

As used herein, "—$(C_1-C_{10})$alkoxy" means a straight chain or branched non-cyclic hydrocarbon having one or more ether groups and from 1 to 10 carbon atoms. Representative straight chain and branched $(C_1-C_{10})$alkoxys include -methoxy, -ethoxy, -propoxy, -butyloxy, -pentyloxy, -hexyloxy, -heptyloxy, -methoxymethyl, -2-methoxyethyl, -5-methoxypentyl, -3-ethoxybutyl and the like.

As used herein, "—$(C_1-C_6)$alkoxy" means a straight chain or branched non-cyclic hydrocarbon having one or more ether groups and from 1 to 6 carbon atoms. Representative straight chain and branched $(C_1-C_5)$alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, "—$(C_1-C_5)$alkoxy" means a straight chain or branched non-cyclic hydrocarbon having one or more ether groups and from 1 to 5 carbon atoms. Representative straight chain and branched $(C_1-C_5)$alkoxys include -methoxy, -ethoxy, -propoxy, -butyloxy, -pentyloxy, -methoxymethyl, -2-methoxyethyl, -5-methoxypentyl, -3-ethoxybutyl and the like.

As used herein, the term "—$(C_3-C_{12})$cycloalkyl" refers to cyclic saturated hydrocarbon having from 3 to 12 carbon atoms. Representative $(C_3-C_{12})$cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, "—$(C_6-C_{14})$bicycloalkyl" means a bicyclic hydrocarbon ring system having from 6 to 14 carbon atoms and at least one saturated cyclic alkyl ring. Representative —$(C_6-C_{14})$bicycloalkyls include -indanyl, -norbornyl, -1,2,3,4-tetrahydronaphthalenyl, -5,6,7,8-tetrahydronaphthalenyl, -perhydronaphthalenyl, and the like.

As used herein, "—$(C_8-C_{20})$tricycloalkyl" means a tricyclic hydrocarbon ring system having from 8 to 20 carbon atoms and at least one saturated cyclic alkyl ring. Representative —$(C_8-C_{20})$tricycloalkyls include -pyrenyl, -adamantyl, -1,2,3,4-tetrahydroanthracenyl, -perhydroanthracenyl, -aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

As used herein, the term "—$(C_4-C_{12})$cycloalkenyl" refers to a cyclic hydrocarbon having from 4 to 12 carbon atoms, and including at least one carbon-carbon double bond. Representative —$(C_3-C_{12})$cycloalkenyls include cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As used herein, "—$(C_7-C_{14})$bicycloalkenyl" means a bicyclic hydrocarbon ring system having at least one carbon-carbon double bond in at least one of the rings and from 7 to 14 carbon atoms. Representative —$(C_7-C_{14})$bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, and the like.

As used herein, "—$(C_8-C_{20})$tricycloalkenyl" means a tricyclic hydrocarbon ring system having at least one carbon-carbon double bond in one of the rings and from 8 to 20 carbon atoms. Representative —$(C_8-C_{20})$tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a,c]cyclooctenyl, 2,3,4,5,6,7,8,9,10,11,12,13-dodecahydro-1H-dibenzo[a,d]cyclononenyl, and the like.

As used herein, "-(3- to 12-membered)heterocycle" or "-(3- to 12-membered)heterocyclo" means a 3- to 12-membered monocyclic heterocyclic ring which is either saturated, or unsaturated, non-aromatic. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(3- to 12-membered)heterocycle can be attached via a nitrogen or carbon atom. Representative -(3- to 12-membered) heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(4- to 8-membered)heterocycle" or "-(4- to 8-membered)heterocyclo" means a 4- to 8-membered monocyclic heterocyclic ring which is either saturated or unsaturated, non-aromatic. A 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(4- to 8-membered)heterocycle can be attached via a nitrogen or carbon atom. Representative -(4- to 8-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(7- to 12-membered)bicycloheterocycle" or "-(7- to 12-membered)bicycloheterocyclo" means a 7- to 12-membered bicyclic, heterocyclic ring which is either saturated, unsaturated, non-aromatic, or aromatic. At least one ring of the bicycloheterocycle contains at least one heteroatom. A -(7- to 12-membered)bicycloheterocycle contains from 1 to 4 heteroatoms independently selected from nitrogen (which can be quaternized), oxygen, and sulfur (including sulfoxide and sulfone). The -(7- to 12-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl and the like.

As used herein a "-(5- to 12-membered)aryl" means an aromatic carbocyclic ring containing 5 to 12 carbon atoms, including both mono- and bicyclic ring systems. Representative (5- to 12-membered)aryl groups include indenyl, -phenyl, -naphthyl, and the like.

As used herein, a "-(6- to 14-membered)aryl" means an aromatic carbocyclic ring containing 6, 7, 8, 9, 10, 11, 12, 13 or 14 carbon atoms, including both mono- and bicyclic ring systems. Representative (6- to 14-membered)aryl groups include indenyl, -phenyl, -naphthyl, anthracenyl and the like. Preferably, the (6- to 14-membered)aryl groups according to the present invention are (6- to 12-membered)aryl groups.

As used herein a "-(7- to 12-membered)bicyclic aryl" means an bicyclic aromatic carbocyclic ring containing 7 to 12 carbon atoms. Representative (7- to 12-membered) bicyclic aryl groups include indenyl, -naphthyl, and the like.

As used herein a "-(5- to 12-membered)aryloxy" means an oxygen substituted by an aromatic carbocyclic ring containing 5 to 12 carbon atoms, including both mono- and bicyclic ring systems. Representative (5- to 12-membered)aryloxy groups include phenoxy and 4-fluorophenoxy, and the like.

As used herein a "hydroxy$(C_1-C_6)$alkyl" means any of the above-mentioned $C_{1-6}$ alkyl groups substituted by one or more hydroxy groups. Representative hydroxy$(C_1-C_6)$alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein a "dihydroxy$(C_1-C_6)$alkyl" means any of the above-mentioned $C_{1-6}$ alkyl groups substituted by two hydroxy groups. Representative dihydroxy$(C_1-C_6)$alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein a "-(3- to 12-membered)carbocyclic ring" means a hydrocarbon ring system having from 3 to 12 carbon atoms, which is either saturated (e.g. cycloalkyl), unsaturated (e.g. cycloakenyl, bicycloakenyl or tricloakenyl), non-aromatic or aromatic. A carbocyclic ring may be monocyclic with 3 to 12 carbons (or also subsets of this range, such as 3-5, 3-6, 5-12, etc.), bicyclic with 5 to 12 carbons (or also subsets of this range, such as 5-9, 6-9, 7-12, etc.), or tricyclic with 7 to 12 carbons.

As used herein a "-(7- to 12-membered)bicyclic ring system" means a 7- to 12-membered a carbocyclic or heterocyclic ring, which may be either unsaturated, saturated, non-aromatic or aromatic.

As used herein, "-(5- to 12-membered)heteroaryl" means an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the bicyclic -(5- to 12-membered)heteroaryl rings contains at least one carbon atom. In another embodiment, both of the bicyclic -(5- to 12-membered)heteroaryl rings contain at least one carbon atom. Representative -(5- to 12-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazinyl, triazinyl, thienyl, thiadiazolyl, cinnolinyl, phthalazinyl, quinazolinyl, and the like.

As used herein, the phrase "tetrazolyl group" means

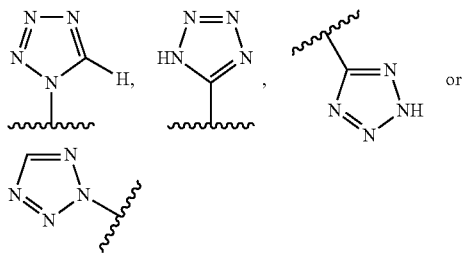

In one embodiment, the tetrazolyl group is

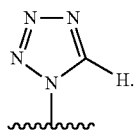

In another embodiment, the tetrazolyl group is

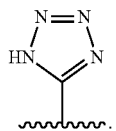

In another embodiment, the tetrazolyl group is

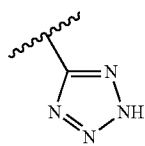 [SMILES: *c1nn[nH]n1]

In another embodiment, the tetrazolyl group is

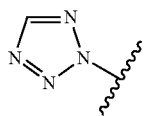

As used herein, the term "(($C_3$-$C_{12}$)cycloalkyl)-($C_1$-$C_6$)alkyl" refers to a ($C_1$-$C_6$)alkyl group as defined above substituted with a ($C_3$-$C_{12}$)cycloalkyl group as defined above. Exemplary cycloalkylalkyl groups include cyclooctylmethyl, cycloheptylmethyl, cyclohexylmethyl, cyclopentylmethyl and the like.

As used herein, the term "(($C_4$-$C_{12}$)cycloalkenyl)-($C_1$-$C_6$)alkyl" refers to a ($C_1$-$C_6$)alkyl group as defined above substituted with a ($C_4$-$C_{12}$)cycloalkenyl group as defined above. Exemplary cycloalkylalkyl groups include cyclooctenylmethyl, cycloheptenylmethyl, cyclohexenylmethyl, cyclopentenylmethyl and the like.

As used herein, the term "(($C_3$-$C_{12}$)cycloalkyl)-($C_1$-$C_6$)alkoxy" refers to a ($C_1$-$C_6$)alkoxy group as defined above substituted with at least one, preferably one, ($C_3$-$C_{12}$)cycloalkyl group as defined above. Exemplary cycloalkylalkoxy groups include cyclooctylmethyl, cycloheptylmethyloxy, cyclohexylmethyloxy, cyclopentylmethyloxy and the like.

As used herein, the terms "((6- to 14-membered)aryl)-($C_1$-$C_6$)alkyl", "((6- to 12-membered)aryl)-($C_1$-$C_6$)alkyl" and "((5- to 12-membered)aryl)-($C_1$-$C_6$)alkyl" refer to a ($C_1$-$C_6$)alkyl group as defined above substituted with a (6- to 14-membered)aryl group, (6- to 12-membered)aryl group and (5- to 12-membered)aryl group, respectively, as defined above. Exemplary arylalkyl groups include benzyl, naphthylmethyl, anthracenylmethyl and the like.

As used herein, the terms "((6- to 14-membered)aryl)-($C_1$-$C_6$)alkoxy", "((6- to 12-membered)aryl)-($C_1$-$C_6$)alkoxy" and "((5- to 12-membered)aryl)-($C_1$-$C_6$)alkoxy" refer to a ($C_1$-$C_6$)alkoxy group as defined above substituted with a (6- to 14-membered)aryl group, (6- to 12-membered)aryl group and (5- to 12-membered)aryl group, respectively, as defined above. Exemplary arylalkoxy groups include benzyloxy, naphthylmethyloxy, anthracenylmethyloxy and the like.

As used herein, the term "((5- to 12-membered)heteroaryl)-($C_1$-$C_6$)alkyl", refers to a ($C_1$-$C_6$)alkyl group as defined above substituted with a (5- to 12-membered)heteroaryl group as defined above. Exemplary heteroarylalkyl groups include tetrazolylmethyl, pyridylmethyl, pyrrolylmethyl and the like.

As used herein, the term "((5- to 12-membered)heteroaryl)-($C_1$-$C_6$)alkoxy", refers to a ($C_1$-$C_6$)alkoxy group as defined above substituted with a (5- to 12-membered)heteroaryl group as defined above. Exemplary heteroarylalkyloxy groups include tetrazolylmethyloxy, pyridylmethyloxy, pyrrolylmethyloxy and the like.

As used herein, the term "(($C_6$-$C_{14}$)bicycloalkyl)-($C_1$-$C_6$)alkyl" refers to a ($C_1$-$C_6$)alkyl group as defined above substituted with a ($C_6$-$C_{14}$)bicycloalkyl group as defined above.

As used herein, the term "(($C_6$-$C_{14}$)bicycloalkenyl)-($C_1$-$C_6$)alkyl" refers to a ($C_1$-$C_6$)alkyl group as defined above substituted with a ($C_6$-$C_{14}$)bicycloalkenyl group as defined above.

As used herein, the term "(($C_8$-$C_{20}$)tricycloalkyl)-($C_1$-$C_6$)alkyl" refers to a ($C_1$-$C_6$)alkyl group as defined above substituted with a ($C_8$-$C_{20}$)tricycloalkyl group as defined above.

As used herein, the term "(($C_8$-$C_{20}$)tricycloalkenyl)-($C_1$-$C_6$)alkyl" refers to a ($C_1$-$C_6$)alkyl group as defined above substituted with a ($C_8$-$C_{20}$)tricycloalkenyl group as defined above.

As used herein, the term "((3- to 12-membered)heterocycle)-($C_1$-$C_6$)alkyl", refers to a ($C_1$-$C_6$)alkyl group as defined above substituted with a (3- to 12-membered)heterocyclo group as defined above.

As used herein, the term "((3- to 12-membered)heterocycle)-($C_1$-$C_6$)alkoxy", refers to a ($C_1$-$C_6$)alkoxy group as defined above substituted with a (3- to 12-membered)heterocyclo group as defined above.

As used herein, the term "((7- to 12-membered)bicycloheterocycle)-($C_1$-$C_6$)alkyl", refers to a ($C_1$-$C_6$)alkyl group as defined above substituted with a (7- to 12-membered)bicycloheterocyclo group as defined above.

As used herein, the term "((7- to 12-membered)bicycloheterocycle)-($C_1$-$C_6$)alkoxy", refers to a ($C_1$-$C_6$)alkoxy group as defined above substituted with a (7- to 12-membered)bicycloheterocyclo group as defined above.

As used herein, the term "((7- to 12-membered)bicyclic ring system)-($C_1$-$C_6$)alkyl", refers to a ($C_1$-$C_6$)alkyl group as defined above substituted with a (7- to 12-membered)bicyclic ring system as defined above.

As used herein, the term "((7- to 12-membered)bicyclic aryl)-($C_1$-$C_6$)alkyl", refers to a ($C_1$-$C_6$)alkyl group as defined above substituted with a (7- to 12-membered)bicyclic aryl group as defined above.

As used herein, the terms "halo" and "halogen" refer to fluoro, chloro, bromo or iodo.

As used herein, "—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

As used herein, "—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —CHBrCl, —CHClI, and —$CHI_2$.

As used herein, "—C(halo)$_3$" means a methyl group where each of the hydrogens of the methyl group has been replaced with a halogen. Representative —C(halo)$_3$ groups include —$CF_3$, —$CCl_3$, —$CBr_3$, and —$CI_3$.

As used herein, the term "optionally substituted" refers to a group that is either unsubstituted or substituted.

Optional substituents on optionally substituted groups, when not otherwise indicated, include 1, 2, or 3 groups each independently selected from the group consisting of —($C_1$-$C_6$)alkyl, OH, halo, —C(halo)$_3$, —CH(halo)$_2$, —$CH_2$(halo), $NH_2$, —NH($C_1$-$C_6$)alkyl, CN, SH, -(3- to 12-membered)carbocyclic ring, -(5- to 12-membered)heterocycle, phenyl, benzyl, (=O), halo($C_1$-$C_6$)alkyl-, —($C_2$-$C_6$)alkenyl, —($C_2$-$C_6$)alkynyl, hydroxy($C_1$-$C_6$)alkyl-, $OR^{4a}$ (such as —OC(halo)$_3$ and —O($C_1$-$C_6$)alkyl), —$CONR^{5b}R^{6b}$, and —$COOR^{7a}$; where $R^{4a}$ is selected from the group consisting of —($C_1$-$C_6$)alkyl, —($C_2$-$C_6$)alkenyl, —($C_2$-$C_6$)alkynyl, —C(halo)$_3$, hydroxy($C_1$-$C_6$)alkyl-, —($C_3$-$C_{12}$)cycloalkyl, —($C_6$-$C_{14}$)bicycloalkyl, —($C_8$-$C_{20}$)tricycloalkyl, —($C_4$-$C_{12}$)cycloalkenyl, —($C_7$-$C_{14}$)bicycloalkenyl, —($C_8$-$C_{20}$)tricycloalkenyl, -(5- to 12-membered)aryl, -(5- to 12-membered)heteroaryl, -(3- to 12-membered)heterocycle, and -(7- to 12-membered)bicycloheterocycle; $R^{5b}$ and $R^{6b}$ are each independently selected from the group consisting of —($C_1$-$C_6$)alkyl, —($C_3$-$C_8$)cycloalkyl, (($C_3$-$C_8$)cycloalkyl)-($C_1$-$C_6$)alkyl-, or together with the nitrogen atom to which they may both be attached form a (4- to 8-membered)heterocycle; and $R^{7a}$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, —($C_1$-$C_6$)alkoxy-$COOR^7$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-$COOR^7$, —NH—C(=O)—($C_1$-$C_6$)alkyl-$COOR^7$, —NH—C(=O)—CH($NH_2$)—($C_1$-$C_6$)alkyl-$COOR^7$, —($C_3$-$C_{12}$)cycloalkyl, -(5- to 12-membered)aryl, -(5- to 12-membered)aryloxy, —($C_1$-$C_6$)alkoxy-$CONR^5R^6$, —NH—($C_1$-$C_6$)alkyl-$CONR^5R^6$, —C(O)NH—($C_1$-$C_6$)alkyl-$COOR^7$, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-$COOR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; wherein $R^5$, $R^6$, and $R^7$ are as defined above for Formula I.

As used herein, the term "alpha-amino compound" means an organic substituent having at least one carbon atom (the alpha- or α-carbon) bonded to the group atom which it is a substituent, and a nitrogen atom also bonded to that α-carbon. The α-carbon additionally bonds two hydrogen atoms or one hydrogen and an additional substituent, such as $R^{17}$. The nitrogen may also may bond two hydrogens or be substituted one or two times, as with $R^{18}$ and $R^{19}$.

As used herein, the term "peptide-forming moiety" means a substituent group that, when incorporated into a Compound of the Invention, forms a peptide bond having a carbonyl adjacent a nitrogen, e.g. —NC(=O)—. While not limited to any mechanism, amines and carboxylic acids are known to react to form peptide bonds in this manner. When a peptide-forming moiety is a substituent on a Nitrogen atom, the next adjacent atom is a carbon double bonded to oxygen. Some representative peptide-forming moieties include amino acids, such as but not limited to Alanine, Arginine, Asparagine, Aspartic Acid, Glutamine, Glutamic Acid, Leucine, Lysine, Phenylalanine, Proline, Serine, Threonine, Tyrosine, and Valine. The α carbon of the amino acids provide a carbonyl (C=O) that is joined to the N of Formula I to form the peptide bond.

As used herein, the term "Z is unsubstituted" means that Z is "—($CH_2$)$_m$—" and m is selected from 1, 2, 3, 4, 5, or 6.

As used herein, the term "Z is substituted" means that Z is "—$(CH_2)_m$—" and m is selected from 1, 2, 3, 4, 5, or 6 and at least one of the hydrogen atoms has been replaced by a ($C_1$-$C_6$)alkyl group.

As used herein, compounds that bind to receptors and mimic the regulatory effects of endogenous ligands are defined as "agonists". Compounds that bind to receptors and are only partly effective as agonists are defined as "partial agonists". Compounds that bind to a receptor but produce no regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics,* $10^{th}$ Ed. (J. G. Hardman, L. E. Limbird and A. Goodman-Gilman eds., 2001). The extent to which a compound binds to a receptor is known as its affinity for the receptor, which is measured by the inhibitor constant, Ki (nM). A lower Ki value indicates higher affinity. The extent to which a compound produces or blocks the production of a regulatory effect at the receptor (i.e. the degree to which it agonizes, partially agonizes or antagonizes the receptor can be measured by $E_{max}$ and $EC_{50}$. A relatively high $E_{max}$—e.g. greater than about 30%—is considered an activator or agonist; whereas a low $E_{max}$—e.g. less than about 10%—is generally considered an antagonist. A partial agonist may have an intermediate $E_{max}$.

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl, respectively, and preferably $^3$H, $^{11}$C, and $^{14}$C. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds are generally described in Filer, Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

Isotopically labeled Compounds of the Invention, as well as the pharmaceutically acceptable salts and solvates thereof, can be used as radioligands to test for the binding of compounds to an opioid or ORL-1 receptor. For example, a radio-labeled Compound of the Invention can be used to characterize specific binding of a test or candidate compound to the receptor. Binding assays utilizing such radio-labeled compounds can provide an alternative to animal testing for the evaluation of chemical structure-activity relationships. In a non-limiting embodiment, the present invention provides a method for screening a candidate compound for the ability to bind to an opioid or ORL-1 receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to enantiomers, diastereomers, and other stereoisomeric forms. The present invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Table A, below, is a list of abbreviations and acronyms that may be used in this disclosure, particularly in the schemes and examples.

TABLE A

| | List of abbreviations |
|---|---|
| ACN | acetonitrile |
| AcOH | acetic acid |
| AIBN | 2,2-azobisisobutyronitrile |
| Alloc | allyloxycarbonyl |
| aq. | aqueous |
| atm | atmosphere(s) |
| Bn | benzyl |
| Boc | tert-butoxycarbonyl |
| $Boc_2O$ | di-tert-butyl dicarbonate |
| Bz | benzoyl |
| ° C. | degrees Celsius |

TABLE A-continued

List of abbreviations

| | |
|---|---|
| CAN | ceric ammonium nitrate |
| Cbz | benzyloxycarbonyl |
| CSA | 10-camphorsulfonic acid |
| d | day(s) |
| DABCO | 1,4-diazabicyclo[2.2.2]octane |
| DBU | 1,8-diazabicyclo[5.4.0]undec-7-ene |
| DCM | dichloromethane |
| DDQ | 2,3-dichloro-5,6-dicyano-1,4-benzoquinone |
| DEAD | diethyl azodicarboxylate |
| DIAD | diisopropyl azodicarboxylate |
| DIBAL | diisobutylaluminum hydride |
| DIPEA | diisopropylethylamine |
| DMAC | dimethylacetamide |
| DMAP | 4-dimethylaminopyridine |
| DME | 1,2-dimethoxyethane |
| DMF | dimethylformamide |
| DMPU | N,N-dimethylpropyleneurea |
| DMSO | dimethylsulfoxide |
| EDCI | 1-ethyl-3-(3-dimethylaminopropyl)carbodiimide) |
| Et$_2$O | diethyl ether |
| EtOAc | ethyl acetate |
| EtOH | ethanol |
| FMOC | 9-fluorenylmethyloxycarbonyl |
| h | hour(s) |
| HATU | 2-(7-aza-1H-benzotriazole-1-yl)-1,1,3,3-tetramethyluronium hexafluorophosphate |
| HPLC | high pressure liquid chromatography |
| i-PrOH | iso-propanol |
| LAH | lithium aluminum hydride |
| LDA | lithium diisopropylamide |
| mCPBA | meta-chloroperoxybenzoic acid |
| MEM | β-methoxyethoxymethyl |
| MeOH | methanol |
| min | minute(s) |
| MOM | methoxymethyl |
| MPLC | medium pressure liquid chromatography |
| Ms | methanesulfonyl |
| MsCl | methanesulfonyl chloride |
| NaHMDS | sodium hexamethyldisilazide |
| NBS | N-bromosuccinimide |
| NMO | N-methylmorpholine N-oxide |
| NMP | N-methyl-2-pyrrolidone |
| PCC | pyridinium chlorochromate |
| Pd/C | palladium on carbon |
| Pd(dppf)Cl$_2$ | [1,1'-bis(diphenylphosphino)ferrocene]dichloropalladium(II) |
| Pd(Ph$_3$P)$_2$Cl$_2$ | bis(triphenylphosphine)palladium(II) dichloride |
| (Ph)$_3$P | triphenylphosphine |
| Piv | pivaloyl |
| PMB | p-methoxybenzyl |
| PTSA | p-toluenesulfonic acid |
| PyBOP | benzotriazol-1-yl-oxytripyrrolidinophosphonium hexafluorophosphate |
| RT | room temperature |
| TBAF | tetrabutylammonium fluoride |
| TBDMS | tert-butyldimethylsilyl |
| t-BuOH | tert-butyl alcohol |
| TEA | triethylamine |
| Tf | trifluoromethanesulfonyl |
| TFA | trifluoroacetic acid |
| TFAA | trifluoroacetic anhydride |
| THF | tetrahydrofuran |
| THP | 2-tetrahydropyranyl |
| TMS | trimethylsilyl |
| TMEDA | N,N,N',N'-tetramethylethylenediamine |

Reaction Schemes

Compounds of the Invention can be made using conventional organic synthesis in view of this disclosure, or by the illustrative methods shown in the schemes below. Starting with commercially available and well-known Thebaine, the derivatization to Compound A can be prepared using conventional organic synthesis methods found in the literature. For example, US Patent Publication 2011/0136846 to Kyle et al., incorporated by reference in its entirety, shows suitable routes to many compounds falling within the definitions of Compound A and its substituents.

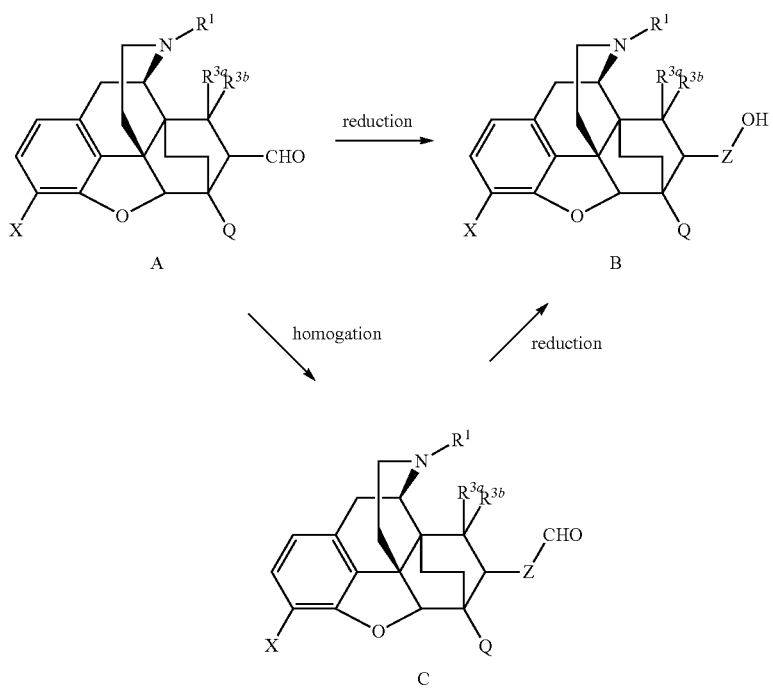

Scheme A

Compound A can be reduced to Compound B (Z is CH$_2$) by treatment with a suitable reducing agent such as sodium borohydride in a suitable solvent such as MeOH. Compound A can also be homologated to Compound C (Z is (CH$_2$)$_{m-1}$, m>1) by one or multiple treatments with a suitable set of conditions [e.g. Levine, S. J. *J. Amer. Chem. Soc.* 1958, 80, 6150] such as reaction with a suitable Wittig reagent such as methoxymethylenetriphenylphosphine followed by hydrolysis under suitable conditions such as aq. acid. Compound C can be reduced to Compound B (Z is (CH$_2$)$_m$, m>1) by treatment with a suitable reducing agent such as sodium borohydride in a suitable solvent such as MeOH.

Scheme B

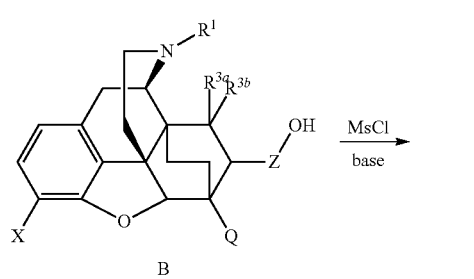

B

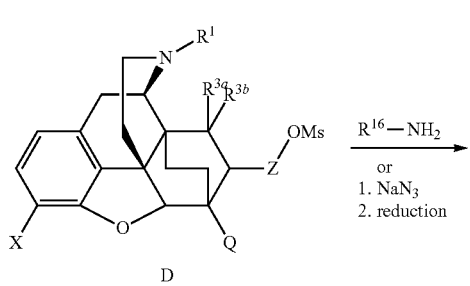

D

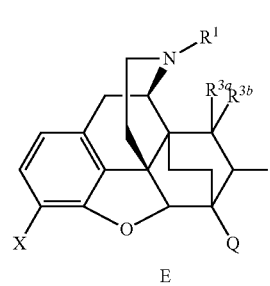

E

The alcohol in Compound B can be converted to a suitable leaving group such as a mesylate by treatment with MsCl in the presence of a suitable base such as TEA in a suitable solvent such as DCM. Compound D can be converted to Compound E either by treatment with a suitable amine in a suitable solvent such as DCM or by treatment with sodium azide in a suitable solvent such as DMF followed by reduction to the amine using suitable conditions such as reaction with Ph$_3$P in a suitable solvent such as THF or hydrogenation in the presence of a suitable catalyst such as Pd/C in a suitable solvent such as MeOH.

Scheme C

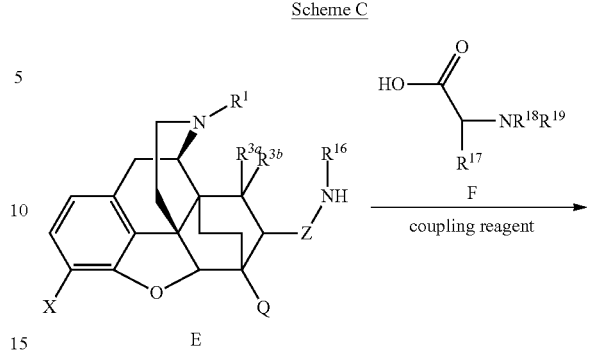

E

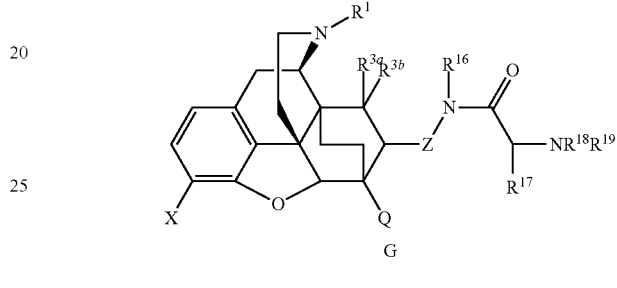

G

Compound E can be converted to Compound G by reaction with Compound F in the presence of a suitable coupling reagent such as HATU in a suitable solvent such as DCM.

Scheme D

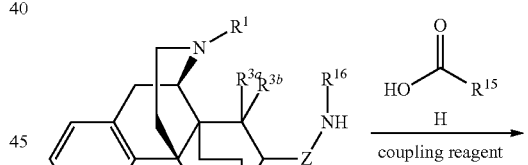

E

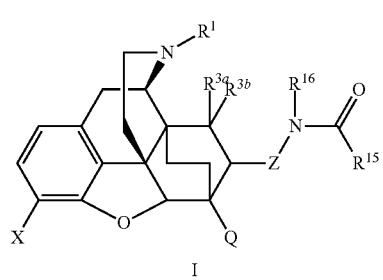

I

Compound E can be converted to Compound I by reaction with Compound H in the presence of a suitable coupling reagent such as HATU in a suitable solvent such as DCM.

Scheme E

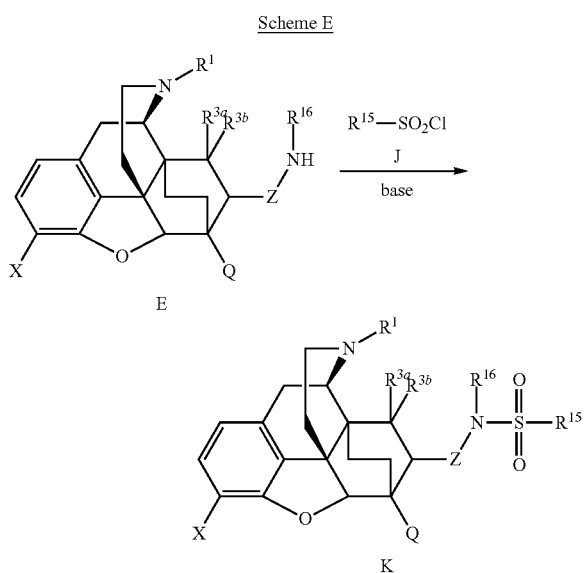

Compound E can be converted to Compound K by reaction with Compound J in the presence of a suitable base such as TEA in a suitable solvent such as DCM.

Scheme F

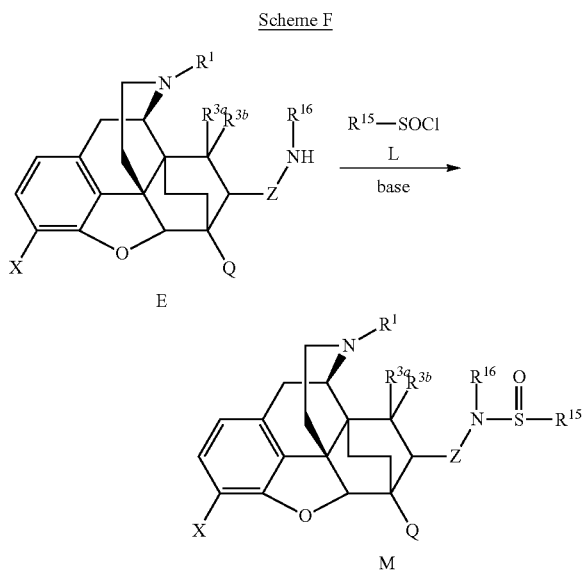

Compound E can be converted to Compound M by reaction with Compound L in the presence of a suitable base such as TEA in a suitable solvent such as DCM.

In the case of compounds where protecting groups are present and they need to be removed, they can be removed using appropriate conditions known to one skilled in the art (e.g. Wuts, P. G. M.; Greene, T. W., "Greene's Protective Groups in Organic Synthesis", 4th Ed., J. Wiley & Sons, NY, 2007).

Stereospecific compounds of Formula IA, IIA and IIIA can be made by selecting starting compound A of suitable stereochemical configuration and modifying in ways known in the art (see e.g. US patent publication 2011/0136846). Naturally occurring opiates have such configuration as shown in the Examples that follow. Compounds such as Compound F, and/or substituents within $R^{15}$ and $R^{17}$ as well as others, may also be obtained in suitable stereochemical configuration for reaction with Compound E to produce Compound G with the desired stereochemistry. For example amino acids (other than glycine) have a chiral a carbon and naturally occurring amino acids have an L optical rotation stereoconfiguration that is useful in this regard.

Testing of Compounds

μ-Opioid Receptor Binding Assay Procedures: Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hr at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISMTM v. 3.0 or higher (San Diego, Calif.), or an in-house function for one-site competition curve-fitting.

μ-Opioid Receptor Binding Data: Generally, the lower the Ki value, the more effective the Compounds of the Invention will be at treating or preventing pain, constipation or another Condition. Typically, the Compounds of the Invention will have a Ki (nM) of about 1000 or less for binding to μ-opioid receptors. In one embodiment the Compounds of the Invention will have a Ki (nM) of about 300 or less for binding to μ-opioid receptors. In one embodiment, Compounds of the Invention will have a Ki (nM) of about 100 or less. In another embodiment, Compounds of the Invention will have a Ki (nM) of about 10 or less. In still another embodiment, Compounds of the Invention will have a Ki (nM) of about 1 or less. In still another embodiment, Compounds of the Invention will have a Ki (nM) of about 0.1 or less.

μ-Opioid Receptor Functional Assay Procedures: [$^{35}$S]GTPγS functional assays were conducted using freshly thawed μ-receptor membranes (Perkin Elmer, Shelton, Conn.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 mM at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hr. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data: μ GTP $EC_{50}$ is the concentration of a compound providing 50% of the maximal response for the compound at a μ-opioid receptor. Compounds of the Invention will typically have a μ GTP $EC_{50}$ (nM) of about 5000 or less. In certain embodiments, Compounds of the Invention will have a μ GTP $EC_{50}$ (nM) of about 2000 or less; or about 1000 or less; or about 100 or less; or about 10 or less; or about 1 or less; or about 0.1 or less.

μ GTP $E_{max}$ (%) is the maximal effect elicited by a compound relative to the effect elicited by DAMGO, a standard μ agonist. Generally, the μ GTP $E_{max}$ (%) value measures the efficacy of a compound to treat or prevent pain or other Conditions. Typically, Compounds of the Invention will have a μ GTP $E_{max}$ (%) of greater than about 10%; or greater than about 20%. In certain embodiments, Compounds of the Invention will have a μ GTP $E_{max}$ (%) of greater than about 50%; or greater than about 65%; or greater than about 75%; or greater than about 85%; or greater than about 100%.

κ-Opioid Receptor Binding Assay Procedures: Membranes from recombinant HEK-293 cells expressing the human κ opioid receptor (κ) (cloned in house) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 mM at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at −80° C.

Radioligand dose displacement assays used 0.4 nM [$^3$H]-U69,593 (GE Healthcare, Piscataway, N.J.; 40 Ci/mmole) with 15 μg membrane protein (recombinant lc opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-Opioid Receptor Binding Data: In certain embodiments, the Compounds of the Invention will have a Ki (nM) for K receptors of about 10,000 or more (which, for purposes of this invention, is interpreted as having no binding to the κ receptors). Certain Compounds of the Invention will have a Ki (nM) of about 20,000 or less for κ receptors. In certain embodiments, Compounds of the Invention will have a Ki (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less.

κ-Opioid Receptor Functional Assay Procedures: Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 mM at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data: κ GTP $EC_{50}$ is the concentration of a compound providing 50% of the maximal response for the compound at a κ receptor. Certain Compounds of the Invention will have a κ GTP $EC_{50}$ (nM) of about 20,000 or less to stimulate κ opioid receptor function. In certain embodiments, Compounds of the Invention will have a κ GTP $EC_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

κ GTP $E_{max}$ (%) is the maximal effect elicited by a compound relative to the effect elicited by U69,593. Certain Compounds of the Invention will have a κ GTP $E_{max}$ (%) of greater than about 1%; or greater than about 5%; or greater than about 10%; or greater than about 20%. In certain embodiments, Compounds of the Invention will have a GTP $E_{max}$ (%) of greater than about 50%; or greater than about 75%; or greater than about 90%; or greater than about 100%.

δ-Opioid Receptor Binding Assay Procedures: δ-opioid Receptor Binding Assay Procedures were conducted as follows. Radioligand dose-displacement assays used 0.3 nM [$^3$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM $MgCl_2$, 5% DMSO, 50 mM Trizma base, pH 7.4). Non-specific binding was determined in the presence of 25 μM unlabeled naloxone. All reactions were performed in 96-deep well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 500 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

δ-Opioid Receptor Binding Data: In certain embodiments, the Compounds of the Invention will have a Ki (nM) for δ receptors of about 10,000 or more (which, for the purposes of this invention, is interpreted as having no binding to the δ receptors). Certain Compounds of the Invention will have a Ki (nM) of about 20,000 or less for δ receptors. In one embodiment, the Compounds of the Invention will have a Ki (nM) of about 10,000 or less; or of about 9000 or less. In another embodiment, the Compounds of the Invention will have a Ki (nM) of about 7500 or less; or of about 6500 or less; or of about 5000 or less; or of about 3000 or less; or of about 2500 or less. In another embodiment, the Compounds of the Invention will have a Ki (nM) of about 1000 or less; or of about 500 or less; or of about 350 or less; or of about 250 or less; or of about 100 or less; or of about 10 or less.

δ-Opioid Receptor Functional Assay Procedures: Functional [$^{35}$S]GTPγS binding assays were conducted as follows. δ opioid receptor membrane solution was prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 mM at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 1-2 hours. Fifty μl/well scintillation cocktail (Perkin Elmer, Shelton, Conn.) was added and plates were counted in a Packard Top-count for 1 min/well.

δ-Opioid Receptor Functional Data: δ GTP EC$_{50}$ is the concentration of a compound providing 50% of the maximal response for the compound at a δ receptor. Certain Compounds of the Invention will have a δ GTP EC$_{50}$ (nM) of about 20,000 or less; or about 10,000 or less. In certain embodiments, the Compounds of the Invention will have a δ GTP EC$_{50}$ (nM) of about 3500 or less; or of about 1000 or less; or of about 500 or less; or of about 100 or less; or of about 90 or less; or of about 50 or less; or of about 25 or less; or of about 10 or less.

δ GTP E$_{max}$ (%) is the maximal effect elicited by a compound relative to the effect elicited by met-enkephalin. Certain Compounds of the Invention of the invention will have a δ GTP E$_{max}$ (%) of greater than about 1%; or of greater than about 5%; or of greater than about 10%. In one embodiment, the Compounds of the Invention will have a δ GTP E$_{max}$ (%) of greater than about 30%. In other embodiments, the Compounds of the Invention will have a δ GTP E$_{max}$ (%) of greater than about 50%; or of greater than about 75%; or of greater than about 90%. In another embodiment, the Compounds of the Invention will have a δ GTP E$_{max}$ (%) of about 100% or greater.

ORL-1 Receptor Binding Assay Procedure: Membranes from recombinant HEK-293 cells expressing the human opioid receptor-like receptor (ORL-1) (Perkin Elmer, Shelton, Conn.) were prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes were collected by centrifugation at 30,000×g for 15 mM at 4° C. and pellets resuspended in hypotonic buffer to a final concentration of 1-3 mg/ml. Protein concentrations were determined using the BioRad protein assay reagent with bovine serum albumen as standard. Aliquots of the ORL-1 receptor membranes were stored at –80° C.

Radioligand binding assays (screening and dose-displacement) used 0.1 nM [$^3$H]-nociceptin (Perkin Elmer, Shelton, Conn.; 87.7 Ci/mmole) with 12 μg membrane protein in a final volume of 500 μl binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at room temperature. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by three filtration washes with 500 μl ice-cold binding buffer. Filter plates were subsequently dried at 50° C. for 2-3 hours. Fifty μl/well scintillation cocktail (Perkin Elmer, Shelton, Conn.) was added and plates were counted in a Packard Top-Count for 1 min/well. The data from screening and dose-displacement experiments were analyzed using Microsoft Excel and the curve fitting functions in GraphPad PRISM™, v. 3.0 or higher, respectively, or an in-house function for one-site competition curve-fitting.

ORL-1 Receptor Binding Data: Certain Compounds of the Invention will have a Ki (nM) of about 1000 or less. In one embodiment, the Compounds of the Invention will have a Ki (nM) of about 500 or less. In other embodiments, the Compounds of the Invention will have a Ki (nM) of about 300 or less; or of about 100 or less; or of about 50 or less; or of about 20 or less. In yet other embodiments, the Compounds of the Invention will have a Ki (nM) of about 10 or less; or of about 1 or less; or of about 0.1 or less.

ORL-1 Receptor Functional Assay Procedure: Membranes from recombinant HEK-293 cells expressing the human opioid receptor-like (ORL-1) (Perkin Elmer, Shelton, Conn.) are prepared by lysing cells in ice-cold hypotonic buffer (2.5 mM Mg Cl$_2$, 50 mM HEPES, pH 7.4) (10 ml/10 cm dish) followed by homogenization with a tissue grinder/Teflon pestle. Membranes are collected by centrifugation at 30,000×g for 15 mM at 4° C., and pellets are resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at –80° C.

Functional [$^{35}$S]GTPγS binding assays are conducted as follows. ORL-1 membrane solution is prepared by sequentially adding final concentrations of 0.026 μg/μl ORL-1 membrane protein, 10 μg/ml saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) is transferred to 96-shallow well polypropylene plates containing 10 μl of 20× concentrated stock solutions of agonist/nociceptin prepared in DMSO. Plates are incubated for 30 mM at room temperature with shaking. Reactions are then terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates are subsequently dried at 50° C. for 2-3 hours. Fifty μl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data: ORL-1 GTP EC$_{50}$ is the concentration of a compound providing 50% of the maximal response for the compound at an ORL-1 receptor. In certain embodiments, the Compounds of the Invention that have a high binding affinity (i.e. low K$_i$ value) will have an ORL-1 GTP EC$_{50}$ (nM) of greater than about 10,000 (i.e. will not stimulate at therapeutic concentrations) In certain embodiments Compounds of the Invention will have an ORL-1 GTP EC$_{50}$ (nM) of about 20,000 or less. In one embodiment, the Compounds of the Invention will have an ORL-1 GTP EC$_{50}$ (nM) of about 10,000 or less; or of about 5000 or less; or of about 1000 or less. In still other embodiments, the Compounds of the Invention will have an ORL-1 GTP EC$_{50}$ (nM) of about 100 or less; or of about 10 or less; or of about 1 or less; or of about 0.1 or less.

ORL-1 GTP E. % is the maximal effect elicited by a compound relative to the effect elicited by nociceptin, a standard ORL-1 agonist. In certain embodiments, Compounds of the Invention will have an ORL-1 GTP E$_{max}$ of less than 10% (which, for the purposes of this invention, is interpreted as having antagonist activity at ORL-1 receptors). Certain Compounds of the Invention will have an ORL-1 GTP E$_{max}$ (%) of greater than 1%; or of greater than 5%; or of greater than 10%. In other embodiments the Compounds of the Invention will have an ORL-1 GTP E$_{max}$ of greater than 20%; or of greater than 50%; or of greater than 75%; or of greater than 88%; or of greater than 100%.

The following Tables provide results on the efficacy of binding and activity response of exemplified Compounds of the Invention at the ORL1, μ-, δ- and κ-opioid receptors.

In TABLE 1, binding affinity of certain Compounds of the Invention to the ORL-1, μ-, δ- and κ-opioid receptors was determined as described above.

TABLE 1

Binding Affinity of Buprenorphine Analog Compounds

| Cmpd. No. | Compound | K$_i$ (nM) Opioid Receptor | | | |
|---|---|---|---|---|---|
| | | ORL-1 | μ | κ | δ |
| 100 | [structure] | | 189.66 ± 59.44 | 13.80 ± 1.25 | |
| 101 | [structure] | 228.55 ± 34.91 | 3.66 ± 1.64 | 0.06 ± 0.01 | 2.01 ± 0.25 |
| 102 | [structure] | | | 0.09 ± 0.03 | |
| 103 | [structure] | | | 0.14 ± 0.03 | |

TABLE 1-continued

Binding Affinity of Buprenorphine Analog Compounds

| Cmpd. No. | Compound | ORL-1 | μ | κ | δ |
|---|---|---|---|---|---|
| 104 | | | | 0.18 ± 0.03 | |
| 105 | | | | 0.06 ± 0.01 | |
| 106 | | | | 0.07 ± 0.02 | |
| 107 | | 0.77 ± 0.24 | | 0.13 ± 0.03 | |
| 108 | | 4.89 ± 2.27 | | 3.05 ± 0.78 | 60.40 ± 16.17 |

$K_i$ (nM)

Opioid Receptor

TABLE 1-continued

Binding Affinity of Buprenorphine Analog Compounds

| Cmpd. No. | Compound | ORL-1 | μ | κ | δ |
|---|---|---|---|---|---|
| 109 | | | 3.18 ± 1.15 | 0.25 ± 0.04 | 58.79 ± 18.32 |
| 110 | | | | 0.35 ± 0.07 | |
| 111 | | | 0.36 ± 0.16 | 0.16 ± 0.03 | |
| 112 | | | 0.53 ± 0.15 | 0.07 ± 0.01 | 16.21 ± 3.69 |
| 113 | | | | 0.13 ± 0.02 | |

$K_i$ (nM) — Opioid Receptor

TABLE 1-continued

Binding Affinity of Buprenorphine Analog Compounds

| Cmpd. No. | Compound | ORL-1 | μ | κ | δ |
|---|---|---|---|---|---|
| 114 | | | | 0.40 ± 0.17 | |
| 115 | | | | 0.16 ± 0.05 | |
| 116 | | | | 0.95 ± 0.34 | |
| 117 | | | | 0.22 ± 0.07 | |
| 118 | | | | 7.10 ± 2.46 | |

TABLE 1-continued

Binding Affinity of Buprenorphine Analog Compounds

| Cmpd. No. | Compound | $K_i$ (nM) Opioid Receptor | | | |
|---|---|---|---|---|---|
| | | ORL-1 | μ | κ | δ |
| 119 | | | | 0.62 ± 0.23 | |
| 120 | | | | 0.35 ± 0.10 | |
| 121 | | | | 0.09 ± 0.04 | |
| 122 | | 5.83 ± 1.45 | | 0.61 ± 0.13 | 20.32 ± 2.94 |
| 123 | Chiral | | | 0.11 ± 0.02 | |

TABLE 1-continued

Binding Affinity of Buprenorphine Analog Compounds

| Comd. No. | Compound | $K_i$ (nM) Opioid Receptor | | | |
|---|---|---|---|---|---|
| | | ORL-1 | μ | κ | δ |
| 124 | Chiral | | | 0.07 ± 0.01 | |
| 125 | Chiral | | | 0.08 ± 0.01 | |
| 126 | Chiral | | | 0.37 ± 0.09 | |
| 127 | Chiral | | | 0.74 ± 0.04 | |
| 128 | | | | 2.62 ± 0.57 | |

TABLE 1-continued

Binding Affinity of Buprenorphine Analog Compounds

| Comd. No. | Compound | ORL-1 | μ | κ | δ |
|---|---|---|---|---|---|
| 129 | | | | 0.17 ± 0.05 | |
| 130 | | | | 13.52 ± 3.07 | |
| 131 | | | | 0.47 ± 0.15 | |
| 132 | | | | 15.28 ± 4.15 | |
| 133 | | | | 0.48 ± 0.13 | |
| 134 | | 1.51 ± 0.06 | 0.32 ± 0.08 | 6.46 ± 1.40 | |

Note: $K_i$ (nM) values for Opioid Receptor.

TABLE 1-continued

Binding Affinity of Buprenorphine Analog Compounds

| Cmpd. No. | Compound | $K_i$ (nM) Opioid Receptor | | | |
|---|---|---|---|---|---|
| | | ORL-1 | μ | κ | δ |
| 135 | (structure) | | | 1.15 ± 0.38 | |
| 136 | (structure) | | | 0.08 ± 0.01 | |
| 137 | (structure) | | | 0.10 ± 0.01 | |

In TABLE 2, the activity response of certain Compounds of the Invention to the μ-, δ- and κ-opioid receptors was determined as described above for functional assays.

TABLE 2

Activity Response of Buprenorphine Analog Compounds

| Cmpd. No. | GTPγS ($EC_{50}$: nM, $E_{max}$: %) Opioid Receptor | | | | | |
|---|---|---|---|---|---|---|
| | μ | | κ | | δ | |
| | $EC_{50}$ | $E_{max}$ | $EC_{50}$ | $E_{max}$ | $EC_{50}$ | $E_{max}$ |
| 100 | >20 μM | | 1606.34 ± 608.92 | 36.67 ± 7.17 | | |
| 101 | >20 μM | | 0.60 ± 0.13 | 49.00 ± 3.56 | >20 μM | |
| 102 | | | >20 μM | | | |
| 103 | | | 4.21 ± 1.39 | 29.33 ± 1.76 | | |
| 104 | | | 6.08 ± 1.85 | 23.50 ± 4.21 | | |
| 105 | | | 10.69 ± 2.17 | 27.00 ± 2.65 | | |
| 106 | | | 2.68 ± 0.53 | | | |
| 107 | >20 μM | | 4.37 ± 1.90 | | | |
| 108 | >20 μM | −1.00 ± 0.00 | 48.83 ± 10.06 | 32.67 ± 0.67 | 21.58 ± 5.05 | 38.00 ± 2.65 |
| 109 | 6454.78 ± 1184.69 | 18.25 ± 3.33 | 1.63 ± 0.29 | 35.00 ± 3.06 | >20 μM | |
| 110 | | | 6.23 ± 1.54 | 25.67 ± 1.76 | | |
| 111 | 29.77 ± 8.32 | 9.60 ± 0.51 | >20 μM | −1.00 ± 0.00 | | |
| 112 | >20 μM | | 3.80 ± 1.17 | 43.00 ± 1.53 | 3.37 ± 0.67 | 55.67 ± 6.57 |
| 113 | | | >20 μM | | | |
| 114 | | | >20 μM | | | |
| 115 | | | >20 μM | | | |
| 116 | | | >20 μM | | | |
| 117 | | | >20 μM | | | |
| 118 | | | 57.96 ± 16.72 | 14.33 ± 2.03 | | |
| 119 | | | >20 μM | | | |
| 120 | | | >20 μM | | | |
| 121 | | | 5.61 ± 1.64 | 16.00 ± 1.15 | | |
| 122 | >20 μM | | 2.64 ± 0.15 | 38.00 ± 2.52 | >20 μM | 0.50 ± 0.50 |
| 123 | 1.41 ± 0.15 | 33.50 ± 1.19 | 1.67 ± 0.25 | 14.67 ± 1.45 | | |
| 124 | 3.44 ± 1.58 | 12.00 ± 1.00 | 2.36 ± 0.45 | 20.75 ± 1.65 | | |

TABLE 2-continued

Activity Response of Buprenorphine Analog Compounds

GTPγS (EC$_{50}$: nM, E$_{max}$: %)
Opioid Receptor

| Cmpd. No. | μ EC$_{50}$ | μ E$_{max}$ | κ EC$_{50}$ | κ E$_{max}$ | δ EC$_{50}$ | δ E$_{max}$ |
|---|---|---|---|---|---|---|
| 125 | 0.82 ± 0.05 | 34.25 ± 3.59 | 1.28 ± 0.40 | 17.75 ± 1.65 | | |
| 126 | 1.85 ± 0.31 | 39.50 ± 2.63 | 2.95 ± 0.60 | 28.33 ± 1.86 | | |
| 127 | 2.42 ± 0.53 | 12.00 ± 0.58 | >20 μM | | | |
| 128 | | | 62.17 ± 12.18 | 22.25 ± 3.35 | | |
| 129 | | | 9.19 ± 3.58 | 26.33 ± 1.45 | | |
| 130 | | | 57.63 ± 13.05 | 21.00 ± 0.91 | | |
| 131 | 4.69 ± 1.46 | 16.25 ± 1.03 | >20 μM | −0.33 ± 0.67 | | |
| 132 | >20 μM | | | | | |
| 133 | >20 μM | | | | | |
| 134 | 6.51 ± 2.49 | 23.75 ± 5.22 | 9.75 ± 2.75 | 40.25 ± 2.25 | 5.71 ± 0.95 | 76.67 ± 5.24 |
| 135 | | | 26.25 ± 10.07 | 16.67 ± 0.88 | | |
| 136 | 0.52 ± 0.06 | 67.67 ± 6.89 | 0.94 ± 0.37 | 33.00 ± 3.61 | | |
| 137 | 1.30 ± 0.44 | 34.75 ± 3.47 | 1.63 ± 0.32 | 35.00 ± 5.13 | | |

The in vitro test results of Tables 1 and 2 show that representative Compounds of the Invention generally have high binding affinity for opioid receptors, and that these compounds activate these receptors as partial to full agonists. Compounds of the Invention are therefore expected to be useful to treat Conditions, particularly pain, that are responsive to the activation of one or more opioid receptors.

In-Vivo Assays for Prevention or Treatment of Pain

Test Animals: Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain: assess the actions of a Compound of the Invention for the treatment or prevention of acute pain, the rat tail flick test was used. Rats were gently restrained by hand and the tail exposed to a focused beam of radiant heat at a point 5 cm from the tip using a tail flick unit (Model 7360, commercially available from Ugo Basile of Italy). Tail flick latencies were defined as the interval between the onset of the thermal stimulus and the flick of the tail. Animals not responding within 20 seconds were removed from the tail flick unit and assigned a withdrawal latency of 20 seconds. Tail flick latencies were measured immediately before (pre-treatment) and 1, 3, and 5 hours following administration of a Compound of the Invention. Data were expressed as tail flick latency(s) and the percentage of the maximal possible effect (% MPE), i.e., 20 seconds, is calculated as follows:

$$\% \, MPE = \frac{\left[ \begin{array}{c} \text{(post administration latency)} - \\ \text{(pre-administration latency)} \end{array} \right]}{(20 \, s - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test was also used. Rats were tested using a hot plate apparatus consisting of a clear plexiglass cylinder with a heated metal floor maintained at a temperature of 48-52° C. (Model 7280, commercially available from Ugo Basile of Italy). Rats were placed into the cylinder on the hot plate apparatus for a maximum duration of 30 s, or until it exhibited a nocifensive behavior (behavioral endpoint), at which time it was removed from the hot plate, and response latency recorded. Hot plate latencies were measured immediately before (pre-treatment) and 1, 3, and 5 hours following administration of a Compound of the Invention. The nocifensive behavioral endpoint was defined as any of the following: 1) paw withdrawal, either as a sustained lift or with shaking or licking; 2) alternating foot lifting; 3) escape or attempted escape from the testing device; or 4) vocalization. Data were expressed as response latency(s) and the percentage of the maximal possible effect was calculated as described above for the tail flick test. The hot plate test is described in G. Woolfe and A. D. Macdonald, *J. Pharmacol. Exp. Ther.* 80:300-307 (1944).

Inflammatory Pain: To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \, \text{Reversal} = \frac{\left[ \begin{array}{c} \text{(post administration } PWT) - \\ \text{(pre-administration } PWT) \end{array} \right]}{[(\text{baseline } PWT) - (\text{pre-administration } PWT)]} \times 100$$

Neuropathic Pain: To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{\left[\begin{array}{c}(\text{post administration } PWT) - \\ (\text{pre-administration } PWT)\end{array}\right]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression: To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., 2000 *Intensive Care Med.* (26) 585-591).

Assessment of Gastric Motility: Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions and Administration

Due to their activity, the Compounds of the Invention are advantageously useful in human and veterinary medicine. As described above, the Compounds of the Invention are useful for treating or preventing a Condition in an animal in need thereof. The Compounds of the Invention can be administered to any animal requiring modulation of the opioid and/or ORL-1 receptors.

When administered to an animal, a Compound of the Invention can be administered as a component of a composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, suppositories, aerosols, sprays, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., $16^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release*, Vol. 2, *Applications and Evaluation*, R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, *Science* 249:1527-1533 (1990); Sefton, *CRC Crit. Ref. Biomed. Eng.* 14:201 (1987); Buchwald et al., Surgery 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each animal's circumstances. Variations in dosing may occur depending upon typical factors such as the weight, age, gender and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Compound of the Invention, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Compound of the Invention is administered, the effective dosage amounts correspond to the total amount administered.

Where a cell capable of expressing the ORL-1 receptor is contacted with a Compound of the Invention in vitro, the amount effective for inhibiting or activating the ORL-1 receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the µ-opioid receptors is contacted with a Compound of the Invention in vitro, the amount effective for inhibiting or activating the µ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the δ-opioid receptors is contacted with a Compound of the Invention in vitro, the amount effective for inhibiting or activating the δ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the κ-opioid receptors is contacted with a Compound of the Invention in vitro, the amount effective for inhibiting or activating the κ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

The Compounds of the Invention can be assayed in vitro or in vivo for the desired therapeutic or prophylactic activity prior to use in humans. Animal model systems can be used to demonstrate safety and efficacy. Certain Compounds of the Invention will have an $ED_{50}$ for treating inflammatory pain ranging from about 0.5 mg/kg to about 20 mg/kg. Certain Compounds of the Invention will produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the invention, methods for treating or preventing a Condition in an animal in need thereof can further comprise co-administering to the animal an effective amount of a second therapeutic agent in addition to a Compound of the Invention (i.e., a first therapeutic agent). An effective amount of the second therapeutic agent will be known or determinable by a medical practitioner in view of this disclosure and published clinical studies. In one embodiment of the invention, where a second therapeutic agent is administered to an animal for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-IA inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Inset, *Analgesic-Antipyretic and Anti-inflammatory Agents and Drugs Employed in the Treatment of Gout*, in *Goodman & Gilman's The Pharmacological Basis of Therapeutics* 617-57 (Perry B. Molinhoff and Raymond W. Ruddon eds., 9$^{th}$ ed 1996); and Glen R. Hanson, *Analgesic, Antipyretic and Anti-Inflammatory Drugs* in *Remington: The Science and Practice of Pharmacy* Vol IA 1196-1221 (A. R. Gennaro ed. 19$^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocominine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the invention is prepared by a method comprising admixing a Compound of the Invention (or a pharmaceutically acceptable salt or solvate thereof) with a pharmaceutically acceptable carrier or excipient. Admixing can be accomplished using methods known for admixing a compound (or derivative) and a pharmaceutically acceptable carrier or excipient. In one embodiment, the Compound of the Invention (or pharmaceutically acceptable salt or solvate thereof) is present in the composition in an effective amount.

EXAMPLES

The following examples serve to further illustrate the invention.

Example 1

((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methanamine (Compound 4)

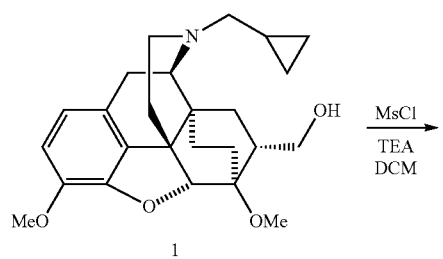

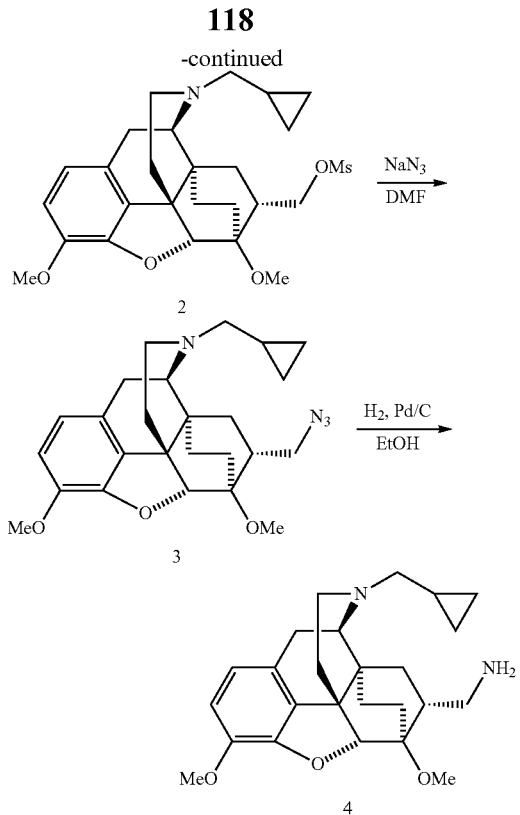

Preparation of Compound 1 proceeds from thebaine (Noramco, Inc, Wilmington, Del.) according to Example 1 of US Patent publication 2011/0136846, previously incorporated (up to Compound 5 of that Example 1, which is the same as Compound 1 herein). MsCl (0.15 mL, 1.5 eq.) was added to a solution of Compound 1 (500 mg, 1.2 mmol) and TEA (0.53 mL, 3.6 mmol) in DCM (25 mL) at 0° C. The reaction mixture was stirred at RT for 14 h. The reaction mixture was then diluted with DCM and washed with water. The organic layer was washed with brine and dried over $Na_2SO_4$. The solvent was concentrated to provide 630 mg of crude Compound 2. This material was used in the next step without further purification.

To a solution of Compound 2 (550 mg, 1.13 mmol) in DMF (10 mL) was added sodium azide (220 mg, 3.36 mmol). The mixture was heated at 65° C. for 16 h. The reaction was quenched with water and extracted with DCM. The organic layer was washed with water, brine and dried over $MgSO_4$. After concentration Compound 3 was obtained which was used in the next step without further purification.

$^1$H NMR $\delta_H$ (300 MHz, $CDCl_3$): 6.70 (d, J=8.0 Hz, 1H), 6.56 (d, J=8.0 Hz, 1H), 4.54-4.48 (m, 1H), 3.86 (s, 3H), 3.70 (dd, J=12.1 Hz, 4.1 Hz, 1H), 3.40 (s, 3H), 3.26-3.18 (m, 1H), 3.06-2.92 (m, 3H), 2.65 (dd, J=11.8 Hz, 5.0 Hz, 1H), 2.37-2.18 (m, 4H), 2.10-1.98 (m, 2H), 1.71-1.46 (m, 1H), 1.58-1.30 (m, 2H), 1.28-1.20 (m, 1H), 1.12-1.00 (m, 1H), 0.85-0.68 (m, 2H), 0.51-0.43 (m, 2H), 0.12-0.03 (m, 2H).

LC/MS, m/z=437 [M+H]$^+$ (Calc: 436).

To a solution of Compound 3 (398 mg, 0.91 mmol) in MeOH (15 mL) and DCM (3 mL) was added 10% Pd/C (398 mg; 50% wet). The reaction mixture was stirred under one atmosphere of $H_2$ for 4 h, filtered through Celite and concentrated. Purification by flash chromatography ($SiO_2$, 1-5% MeOH (with 7% ammonia)/DCM) gave Compound 4 as a white solid.

$^1$H NMR $\delta_H$ (300 MHz, CDCl$_3$): 6.69 (d, J=8.25 Hz, 1H), 6.55 (d, J=8.25 Hz, 1H), 4.50 (d, J=1.92 Hz, 1H), 3.84 (s, 3H), 3.40 (s, 3H), 2.92-3.13 (m, 4H), 2.53-2.69 (m, 2H), 2.17-2.40 (m, 4H), 2.03 (dt, J=12.63, 5.76 Hz, 1H), 1.79-1.93 (m, 1H), 1.66 (dd, J=12.90, 2.46 Hz, 1H), 1.33-1.60 (m, 4H), 0.95-1.11 (m, 2H), 0.67-0.85 (m, 2H), 0.41-0.52 (m, 2H), 0.05-0.12 (m, 2H).

LC/MS, m/z=411 [M+H]$^+$ (Calc: 410).

In a similar manner the following compound was prepared.

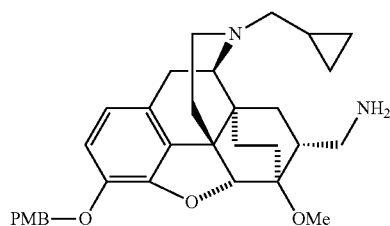

(((4R,4aS,6R,7R,7aR,12bS)-3-(cyclopropylmethyl)-7-methoxy-9-((4-methoxybenzyl)oxy)-1,2,3,4,5,6,7,7a-octahydro-4a,7-ethano-4,12-methanobenzofuro[3,2-e]isoquinolin-6-yl)methanamine (Compound 5)

$^1$H NMR $\delta_H$ (300 MHz, CDCl$_3$): 7.35 (d, J=8.3 Hz, 2H), 6.89 (d, J=8.3 Hz, 2H), 6.71 (d, J=8.0 Hz, 1H), 6.49 (d, J=8.3 Hz, 1H), 5.11 (m, 2H), 4.49 (d, J=1.7 Hz, 1H), 3.79 (s, 3H), 3.42 (s, 3H), 2.90-3.15 (m, 4H), 2.54-2.69 (m, 2H), 2.15-2.38 (m, 4H), 1.97-2.11 (m, 1H), 1.80-1.93 (m, 1H), 1.63 (m, 1H), 1.33-1.56 (m, 4H), 0.94-1.10 (m, 2H), 0.63-0.84 (m, 2H), 0.35-0.51 (m, 2H), 0.06-0.12 (m, 2H).

Example 2

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-phenylpropanamide (Compound 101)

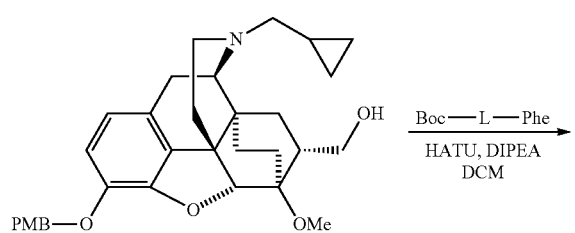

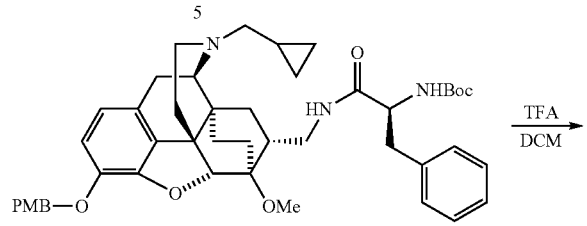

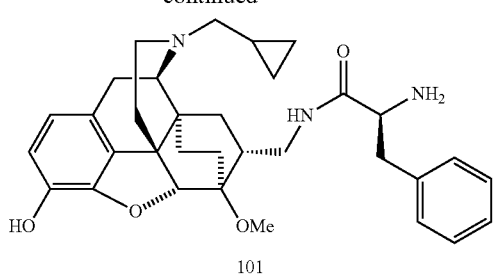

101

A mixture of Compound 5 (248 mg, 0.48 mmol), Boc-(L)-phenylalanine (152 mg, 0.58 mmol, 1.2 eq.), HATU (274 mg, 0.72 mmol, 1.5 eq.) and DIPEA (0.418 mL, 2.4 mmol, 5 eq.) in DCM (10 mL) was stirred at RT overnight. The volatiles were removed and the residue purified by flash chromatography (SiO$_2$, 10-50% EtOAc/hexanes) to give 367 mg (86%) of Compound 6.

$^1$H NMR $\delta_H$ (300 MHz, CDCl$_3$): 7.26-7.41 (m, 2H), 7.15-7.25 (m, 5H), 6.87 (d, J=8.5 Hz, 1H), 6.72 (d, J=8.3 Hz, 1H), 6.54-6.65 (m, 1H), 6.49 (d, J=8.0 Hz, 1H), 5.09 (m, 2H), 4.28 (s, 1H), 3.80 (s, 3H), 3.40-3.59 (m, 2H), 3.31 (s, 3H), 2.82-3.16 (m, 2H), 2.58-2.69 (m, 2H), 2.08-2.35 (m, 2H), 1.89-2.02 (m, 2H), 1.59 (s, 9H), 1.42 (s, 9H), 0.56-1.04 (m, 3H), 0.41-0.55 (m, 2H), 0.08 (m, 2H).

A mixture of Compound 6 (300 mg, 0.39 mmol), TFA (3 mL) and DCM (3 mL) was stirred at 0° C. for 1 h and the residue, after evaporating the solvent, was purified by flash chromatography (SiO$_2$, 1-5% MeOH (with 7% ammonia)/DCM) to provide 200 mg (93%) of Compound 101 as the free base. The free base (190 mg) was dissolved in DCM (1 mL) and 1M HCl in Et$_2$O (1 mL) was added and the mixture stirred at 0° C. for 1 h. The solvents were evaporated and the residue was triturated with Et$_2$O to give 165 mg of (S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-phenylpropanamide (Compound 101) as the HCl salt.

$^1$H NMR $\delta_H$ (300 MHz, DMSO-d$_6$): 9.18-9.44 (m, 2H), 8.72-8.81 (m, 1H), 8.36 (br. s., 3H), 7.18-7.46 (m, 5H), 6.70 (d, J=8.3 Hz, 1H), 6.55 (d, J=8.3 Hz, 1H), 4.63 (s, 21H), 3.93-4.09 (m, 1H), 3.84 (d, J=6.1 Hz, 1H), 3.25 (s, 4H), 2.65-3.16 (m, 7H), 2.09-2.29 (m, 2H), 1.76-1.94 (m, 1H), 1.28-1.51 (m, 1H), 1.10-1.29 (m, 4H), 0.47-0.83 (m, 13H), 0.31-0.47 (m, 2H).

LC/MS, m/z=544.2 [M+H]$^+$ (Calc: 543.7).

In a similar manner the following compounds were prepared and protecting groups removed where necessary.

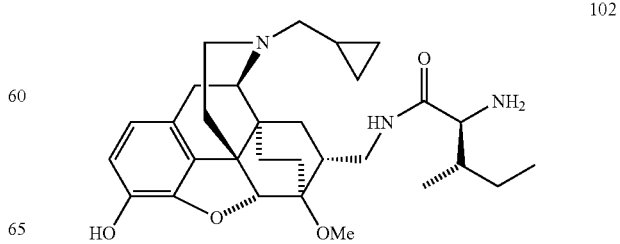

102

103
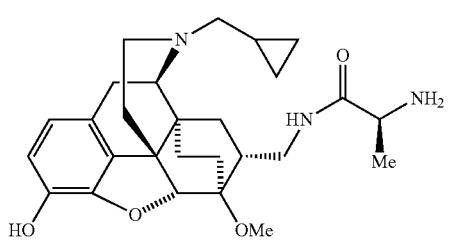
104
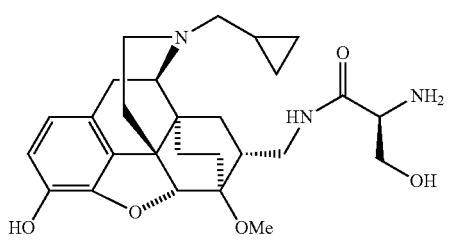
105
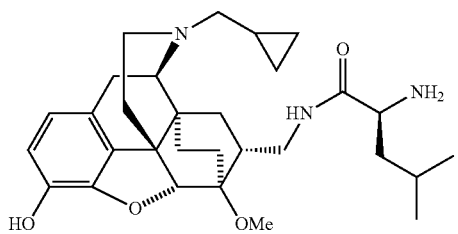
106
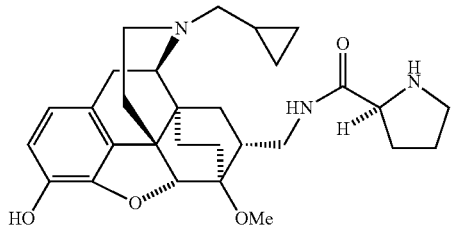
107
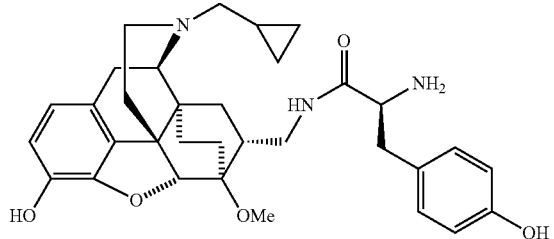
108
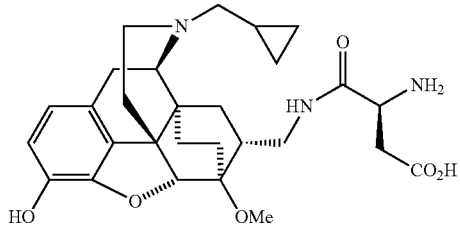
109
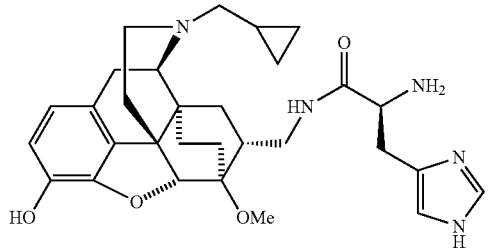
110
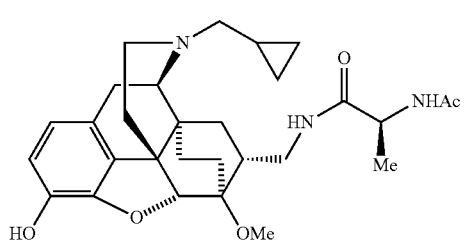
111
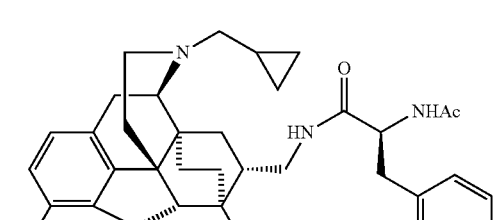
112
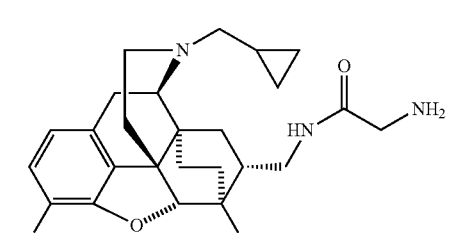
113
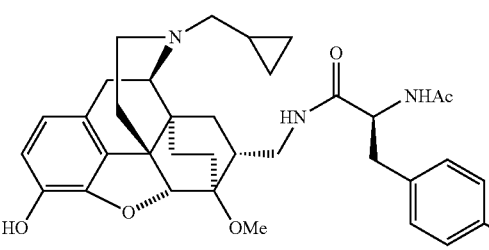
114
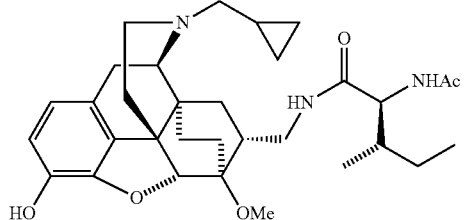

-continued

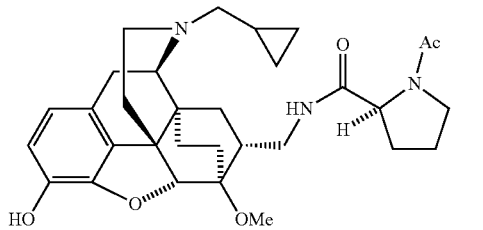
115

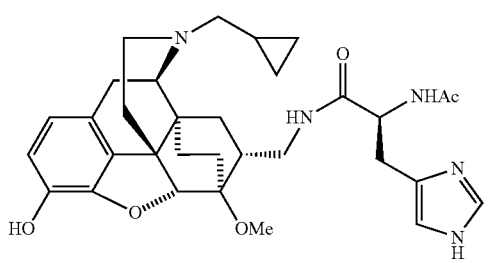
116

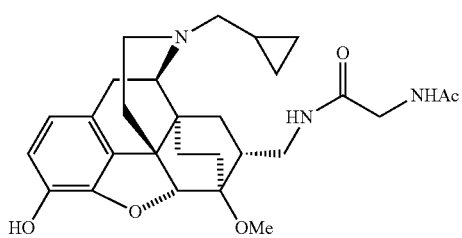
117

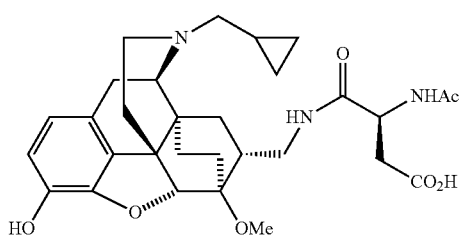
118

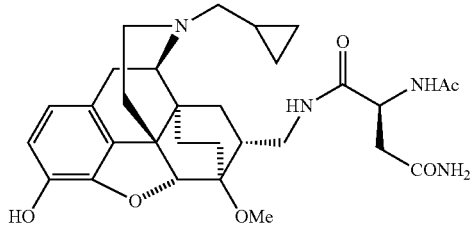
119

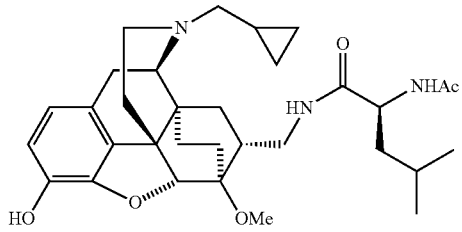
120

-continued

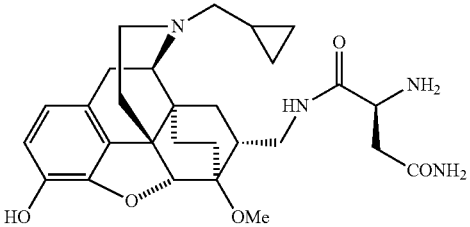
121

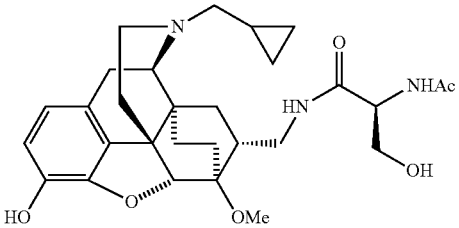
122

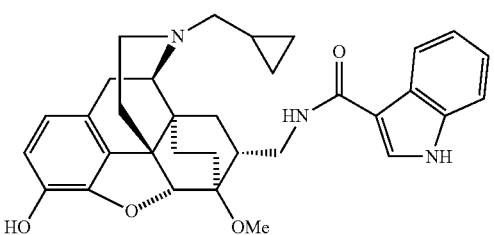
123

(2S,3S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-methylpentanamide (Compound 102)

$^1$H NMR $\delta_H$ (300 MHz, DMSO-d$_6$): 9.32 (s, 1H), 9.21 (br.s, 1H), 8.63-8.66 (m, 1H), 8.15-8.29 (m, 3H), 6.70 (d, J=8.0 Hz, 1H), 6.56 (d, J=8.0 Hz, 1H), 4.65 (s, 1H), 3.84 (d, J=6.0 Hz, 1H), 3.61 (br.s, 1H), 3.35 (s, 3H), 3.00-3.17 (m, 1H), 3.08-3.06 (m, 2H), 2.69-2.95 (m, 3H), 2.09-2.39 (m, 2H), 1.66-2.01 (m, 2H), 1.34-1.66 (m, 2H), 1.05-1.30 (m, 6H), 0.80-0.98 (m, 6H), 0.60-0.74 (m, 3H), 0.53 (m, 1H), 0.33-0.47 (m, 1H).

LC/MS, m/z=510.3 [M+H]$^+$ (Calc: 509.7).

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)propanamide (Compound 103)

$^1$H NMR $\delta_H$ (300 MHz, DMSO-d$_6$): 9.42 (br.s, 1H), 9.31 (s, 1H), 8.60-8.64 (m, 1H), 8.25 (br.s, J 3H), 6.70 (d, J=8.0 Hz, 1H), 6.55 (d, J=8.0 Hz, 1H), 4.66 (s, 1H), 3.82 (d, J=6.1 Hz, 1H), 3.27-3.38 (m, 6H), 3.03-3.27 (m, 1H), 2.86-3.00 (m, 1H), 2.72-2.86 (m, 1H), 1.97-2.32 (m, 2H), 1.85 (d, J=10.7 Hz, 1H), 1.42 (d, J=6.9 Hz, 4H), 0.99-1.30 (m, 4H), 0.55-0.81 (m, 3H), 0.51-0.59 (m, 1H), 0.35-0.49 (m, 1H).

LC/MS, m/z=468.2 [M+H]$^+$ (Calc: 467.6).

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-hydroxypropanamide (Compound 104)

$^1$H NMR $\delta_H$ (300 MHz, DMSO-d$_6$): 9.33 (s, 1H), 8.44-8.71 (m, 2H), 8.16 (br. s., 3H), 6.69 (d, J=8.0 Hz, 1H), 6.56 (d, J=8.0 Hz, 1H), 5.56 (br.s, 1H), 4.70 (s, 1H), 3.68-4.06 (m, 8H), 3.34-3.66 (m, 7H), 3.05-3.24 (m, 2H), 2.62-3.01 (m, 4H), 2.05-2.31 (m, 2H), 1.77-2.01 (m, 1H), 1.34-1.56 (m, 1H), 1.12-1.34 (m, 3H), 0.96-1.09 (m, 1H), 0.50-0.80 (m, 3H), 0.31-0.47 (m, 2H).
LC/MS, m/z=484.2 [M+H]$^+$ (Calc: 483.6).

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-4-methylpentanamide (Compound 105)

$^1$H NMR $\delta_H$ (300 MHz, DMSO-d$_6$): 9.33 (s, 1H), 9.25 (br.s, 1H), 8.65-8.85 (m, 1H), 8.31 (br.s, 3H), 6.70 (d, J=8.0 Hz, 1H), 6.56 (d, J=8.0 Hz, 1H), 4.66 (s, 1H), 3.84 (d, J=6.3 Hz, 1H), 3.65-3.79 (m, 1H), 3.38-3.51 (m, 5H), 3.19-3.27 (m, 2H), 2.64-2.94 (m, 4H), 2.05-2.41 (m, 2H), 1.74-1.98 (m, 1H), 1.33-1.73 (m, 4H), 1.02-1.34 (m, 4H), 0.87-1.00 (m, 7H), 0.59-0.84 (m, 3H), 0.47-0.59 (m, 1H), 0.31-0.47 (m, 1H).
LC/MS, m/z=510.2 [M+H]$^+$ (Calc: 509.7).

(S)-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)pyrrolidine-2-carboxamide (Compound 106)

$^1$H NMR $\delta_H$ (300 MHz, DMSO-d$_6$): 9.36 (br.s, 1H), 9.33 (s, 1H), 8.63-8.79 (m, 1H), 8.39-8.63 (m, 2H), 6.69 (d, J=8.0 Hz, 1H), 6.55 (d, J=8.0 Hz, 1H), 4.72 (s, 1H), 3.99-4.28 (m, 1H), 3.82 (d, J=7.2 Hz, 1H), 3.36-3.62 (m, 5H), 3.05-3.23 (m, 4H), 2.59-3.00 (m, 4H), 2.04-2.37 (m, 4H), 1.63-2.01 (m, 4H), 1.11-1.49 (m, 4H), 0.95-1.09 (m, 1H), 0.61-0.76 (m, 2H), 0.51-0.60 (m, 1H), 0.30-0.51 (m, 2H).
LC/MS, m/z=494.2 [M+H]$^+$ (Calc: 493.6).

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(4-hydroxyphenyl)propanamide (Compound 107)

$^1$H NMR $\delta_H$ (300 MHz, DMSO-d$_6$): 9.43 (br.s, 1H), 9.33 (br.s, 1H), 8.49-8.66 (m, 1H), 8.35-8.50 (m, 1H), 7.91-8.27 (m, 3H), 7.07 (d, J=8.5 Hz, 2H), 6.66-6.82 (m, 3H), 6.56 (d, J=8.0 Hz, 1H), 4.66 (s, 1H), 3.83-3.94 (m, 1H), 3.78 (d, J=2.2 Hz, 1H), 3.38-3.72 (m, 1H), 3.08-3.20 (m, 6H), 2.64-2.99 (m, 5H), 2.22-2.34 (m, 1H), 2.05-2.20 (m, 2H), 1.79-1.99 (m, 1H), 1.39-1.48 (m, 1H), 1.09-1.35 (m, 3H), 0.97-1.09 (m, 1H), 0.49-0.75 (m, 3H), 0.37-0.49 (m, 2H).
LC/MS, m/z=560.3 [M+H]$^+$ (Calc: 599.7).

(S)-3-amino-4-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)amino)-4-oxobutanoic acid (Compound 108)

$^1$H NMR $\delta_H$ (300 MHz, DMSO-d$_6$): 9.30 (br. s, 1H), 8.60 (m, 1H), 8.23 (br. s., 3H), 6.68 (d, J=8.3 Hz, 1H), 6.54 (d, J=8.3 Hz, 1H), 4.66 (s, 1H), 3.93-4.17 (m, 1H), 3.44-3.87 (m, 4H), 3.22-3.43 (m, 5H), 2.63-2.95 (m, 6H), 1.87-2.21 (m, 2H), 1.81-1.94 (m, 1H), 1.32-1.49 (m, 1H), 1.10-1.22 (m, 3H), 0.91-1.11 (m, 1H), 0.56-0.73 (m, 3H), 0.28-0.50 (m, 2H).
LC/MS, m/z=512.2 [M+H]$^+$ (Calc: 511.6).

(S)-2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(1H-imidazol-4-yl)propanamide (Compound 109)

$^1$H NMR $\delta_H$ (300 MHz, DMSO-d$_6$): 9.22-9.50 (m, 1H), 8.75-9.09 (m, 1H), 8.58-8.72 (m, 1H), 8.36 (hr. s, 2H), 7.41 (s, 1H), 6.69 (d, J=8.0 Hz, 1H), 6.54 (d, J=8.0 Hz, 1H), 4.66 (s, 1H), 4.01-4.15 (m, 1H), 3.73-3.88 (m, 1H), 3.04-3.53 (m, 10H), 2.68-3.04 (m, 4H), 1.99-2.33 (m, 2H), 1.81-1.99 (m, 1H), 1.33-1.55 (m, 1H), 1.14-1.33 (m, 3H), 0.96-1.14 (m, 1H), 0.52-0.78 (m, 3H), 0.33-0.50 (m, 2H).
LC/MS, m/z=534.2 [M+H]$^+$ (Calc: 533.7).

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)propanamide (Compound 110)

$^1$H NMR $\delta_H$ (300 MHz, DMSO-d$_6$): 9.30 (hr. s, 1H), 8.35 (hr. s, 1H), 8.04 (d, J=7.4 Hz, 2H), 6.68 (d, J=8.0 Hz, 1H), 6.55 (d, J=8.0 Hz, 1H), 4.71 (s, 1H), 4.14-4.42 (m, 1H), 3.82 (d, J=6.3 Hz, 1H), 3.49-3.74 (m, 4H), 3.38-3.47 (m, 5H), 2.97-3.23 (m, 1H), 2.70-2.97 (m, 3H), 2.01-2.27 (m, 2H), 1.84 (s, 4H), 0.91-1.43 (m, 6H), 0.49-0.83 (m, 3H), 0.31-0.50 (m, 2H).
LC/MS, m/z=510.3 [M+H]$^+$ (Calc: 509.6).

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-phenylpropanamide (Compound 111)

$^1$H NMR $\delta_H$ (300 MHz, DMSO-d$_6$): 9.31 (s, 1H), 8.23-8.40 (m, 1H), 8.16-8.24 (m, 1H), 8.12 (d, J=8.5 Hz, 1H), 7.12-7.38 (m, 5H), 6.67 (d, J=8.3 Hz, 1H), 6.55 (d, J=8.3 Hz, 1H), 4.72 (s, 1H), 4.34-4.61 (m, 1H), 3.82 (d, J=6.3 Hz, 1H), 3.33-3.65 (m, 4H), 3.09-3.27 (m, 4H), 2.94-3.07 (m, 2H), 2.80-2.91 (m, 2H), 2.60-2.77 (m, 2H), 2.11-2.28 (m, 2H), 1.81-1.91 (m, 1H), 1.72 (s, 3H), 0.91-1.45 (m, 3H), 0.52-0.76 (m, 3H), 0.31-0.50 (m, 2H).
LC/MS, m/z=586.3 [M+H]$^+$ (Calc: 585.7).

2-amino-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)acetamide (Compound 112)

$^1$H NMR $\delta_H$ (300 MHz, DMSO-d$_6$): 9.33 (br.s, 1H), 8.56-8.72 (m, 2H), 8.06 (br. s, 3H), 6.69 (d, J=8.0 Hz, 1H), 6.56 (d, J=8.0 Hz, 1H), 4.69 (s, 1H), 3.81 (d, J=6.6 Hz, 1H), 3.37-3.69 (m, 5H), 2.93-3.36 (m, 8H), 2.66-2.88 (m, 5H), 2.09-2.24 (m, 2H), 1.72-1.92 (m, 1H), 1.34-1.64 (m, 4H), 0.99-1.11 (m, 1H), 0.52-0.82 (m, 3H), 0.36-0.52 (m, 2H).
LC/MS, m/z=454.2 [M+H]$^+$ (Calc: 453.6).

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(4-hydroxyphenyl)propanamide (Compound 113)

$^1$H NMR $\delta_H$ (300 MHz, DMSO-d$_6$): 9.35 (br. s, 1H), 9.26 (br. s, 1H), 8.22-8.38 (m, 1H), 8.11-8.20 (m, 1H), 8.04 (d, J=8.8 Hz, 1H), 7.02 (d, J=8.3 Hz, 2H), 6.61-6.72 (m, 3H), 6.48-6.61 (m, 1H), 4.71 (s, 1H), 4.36-4.51 (m, 1H), 3.75-3.88 (m, 1H), 3.10-3.38 (m, 6H), 2.92-3.05 (m, 1H), 2.77-2.92 (m, 5H), 2.56-2.73 (m, 5H), 2.10-2.30 (m, 3H), 1.81-1.93 (m, 1H), 1.02-1.46 (m, 5H), 0.50-0.76 (m, 3H), 0.37-0.45 (m, 2H).
LC/MS, m/z=602.3 [M+H]$^+$ (Calc: 601.7).

(2S,3S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-methylpentanamide (Compound 114)

$^1$H NMR $\delta_H$ (300 MHz, DMSO-d$_6$): 9.30 (br. s, 1H), 8.21-8.29 (m, 1H), 8.13-8.20 (m, 1H), 7.92 (d, J=8.8 Hz, 1H), 6.68 (d, J=8.3 Hz, 1H), 6.54 (d, J=8.3 Hz, 1H), 4.73 (s, 1H), 4.16-4.21 (m, 1H), 3.80-3.86 (m, 1H), 3.25-3.38 (m, 6H), 2.70-3.05 (m, 5H), 2.10-2.40 (m, 2H), 1.71-1.93 (m, 4H), 1.02-1.39 (m, 8H), 0.80-0.96 (m, 7H), 0.37-0.45 (m, 2H).
LC/MS, m/z=522.3 [M+H]$^+$ (Calc: 551.7).

(S)-1-acetyl-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)pyrrolidine-2-carboxamide (Compound 115)

$^1$H NMR $\delta_H$ (300 MHz, DMSO-d$_6$): 9.31 (br. s, 1H), 8.10-8.30 (m, 2H), 7.90-7.94 (m, 1H), 6.67 (d, J=8.3 Hz, 1H), 6.55 (d, J=8.3 Hz, 1H), 4.71 (s, 1H), 4.21-4.34 (m, 1H), 3.81-3.84 (m, 1H), 3.02-3.51 (m, 10H), 2.81-2.86 (m, 3H), 1.86-2.40 (m, 11H), 1.04-1.39 (m, 5H), 0.41-0.94 (m, 5H).
LC/MS, m/z=536.3 [M+H]$^+$ (Calc: 535.7).

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(1H-imidazol-4-yl)propanamide (Compound 116)

$^1$H NMR $\delta_H$ (300 MHz, DMSO-d$_6$): 9.31 (br. s, 1H), 8.92 (s, 1H), 8.15-8.18 (m, 2H), 7.32 (s, 1H), 6.69 (d, J=8.3 Hz, 1H), 6.54 (d, J=8.3 Hz, 1H), 4.70 (s, 1H), 4.59-4.61 (m, 1H), 3.79-3.81 (m, 1H), 2.90-3.35 (m, 12H), 2.10-2.42 (m, 4H), 1.87-1.93 (m, 4H), 1.01-1.41 (m, 5H), 0.40-0.86 (m, 5H).
LC/MS, m/z=576.3 [M+H]$^+$ (Calc: 575.7).

2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)acetamide (Compound 117)

$^1$H NMR $\delta_H$ (300 MHz, DMSO-d$_6$): 9.33 (br. s, 1H), 8.37 (br. s, 1H), 8.02-8.10 (m, 2H), 6.69 (d, J=8.0 Hz, 1H), 6.55 (d, J=8.0 Hz, 1H), 4.70 (s, 1H), 3.81 (m, 1H), 3.67-3.78 (m, 2H), 3.27-3.39 (m, 5H), 3.01-3.26 (m, 2H), 2.56-3.00 (m, 4H), 2.09-2.24 (m, 2H), 1.86 (s, 3H), 1.04-1.36 (m, 5H), 0.52-0.82 (m, 3H), 0.36-0.52 (m, 2H).
LC/MS, m/z=496.3 [M+H]$^+$ (Calc: 495.6).

(S)-3-acetamido-4-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)amino)-4-oxobutanoic acid (Compound 118)

$^1$H NMR $\delta_H$ (300 MHz, DMSO-d$_6$): 9.25-9.33 (m, 1H), 8.23-8.41 (m, 1H), 8.10-8.22 (m, 1H), 7.89-8.02 (m, 1H), 6.67 (d, J=8.5 Hz, 1H), 6.55 (d, J=8.5 Hz, 1H), 4.70 (s, 1H), 4.50-4.65 (m, 1H), 3.13-3.62 (m, 5H), 2.67-3.05 (m, 5H), 2.30-2.41 (m, 3H), 2.06-2.29 (m, 3H), 1.85 (s, 4H), 0.95-1.48 (m, 6H), 0.54-0.79 (m, 3H), 0.33-0.53 (m, 2H).
LC/MS, m/z=554.2 [M+H]$^+$ (Calc: 553.6).

(S)-2-acetamido-N$^1$-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)succinamide (Compound 119)

$^1$H NMR $\delta_H$ (300 MHz, DMSO-d$_6$): 9.20-9.36 (m, 1H), 8.23-8.41 (m, 1H), 8.00-8.11 (m, 1H), 7.80-7.96 (m, 1H), 7.30 (m, 1H), 6.88 (br. s., 1H), 6.67 (d, J=8.0 Hz, 1H), 6.55 (d, J=8.0 Hz, 1H), 4.70 (s, 1H), 4.46-4.62 (m, 1H), 3.76-3.87 (m, 1H), 3.05-3.47 (m, 8H), 2.69-3.03 (m, 4H), 2.57-2.68 (m, 1H), 2.06-2.41 (m, 3H), 1.85 (s, 4H), 0.93-1.49 (m, 5H), 0.53-0.76 (m, 3H), 0.31-0.50 (m, 2H).
LC/MS, m/z=533.2 [M+H]$^+$ (Calc: 552.7).

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-4-methylpentanamide (Compound 120)

$^1$H NMR $\delta_H$ (300 MHz, DMSO-d$_6$): 9.41 (br.s, 1H), 8.34 (br. s, 1H), 8.03-8.17 (m, 1H), 7.98 (d, J=8.5 Hz, 1H), 6.71 (d, J=8.3 Hz, 1H), 6.55 (d, J=8.3 Hz, 1H), 4.72 (s, 1H), 4.27-4.50 (m, 1H), 3.82 (d, J=6.3 Hz, 1H), 3.37-3.49 (m, 1H), 3.31 (s, 3H), 3.11-3.26 (m, 2H), 2.97-3.09 (m, 1H), 2.73-2.96 (m, 2H), 2.56-2.68 (m, 1H), 2.12-2.27 (m, 2H), 1.85 (s, 3H), 1.53-1.65 (m, 1H), 0.97-1.49 (m, 6H), 0.77-0.92 (m, 6H), 0.62-0.77 (m, 2H), 0.50-0.64 (m, 1H), 0.33-0.52 (m, 2H).
LC/MS, m/z=552.7 [M+H]$^+$ (Calc: 551.7).

(S)-2-amino-N$^1$-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)succinamide (Compound 121)

$^1$H NMR $\delta_H$ (300 MHz, DMSO-d$_6$): 9.33 (br. s, 1H), 8.43-8.69 (m, 2H), 8.14 (br. s., 3H), 7.68 (br. s, 1H), 7.29 (br. s, 1H), 6.69 (d, J=8.0 Hz, 1H), 6.56 (d, J=8.0 Hz, 1H), 4.68 (s, 1H), 3.89-4.09 (m, 1H), 3.82 (d, J=7.2 Hz, 1H), 3.46-3.70 (m, 4H), 3.35-3.46 (m, 6H), 2.96-3.15 (m, 2H), 2.57-2.98 (m, 6H), 2.04-2.27 (m, 2H), 1.82-2.00 (m, 1H), 0.97-1.41 (m, 4H), 0.54-0.80 (m, 3H), 0.32-0.52 (m, 2H).
LC/MS, m/z=511.6 [M+H]$^+$ (Calc: 510.6).

(S)-2-acetamido-N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-hydroxypropanamide (Compound 122)

$^1$H NMR $\delta_H$ (300 MHz, DMSO-d$_6$): 9.30 (br. s, 1H), 8.84 (br. s, 1H), 7.83-8.04 (m, 2H), 6.68 (d, J=8.0 Hz, 1H), 6.54 (d, J=8.0 Hz, 1H), 4.69 (s, 1H), 4.17-4.37 (m, 1H), 3.80 (d, J=7.2 Hz, 1H), 3.57 (d, J=5.2 Hz, 1H), 3.38 (br. s., 12H), 3.01-3.22 (m, 2H), 2.74-2.96 (m, 3H), 2.10-2.30 (m, 2H), 1.88 (s, 3H), 0.97-1.50 (m, 4H), 0.63-0.77 (m, 2H), 0.49-0.65 (m, 2H), 0.30-0.48 (m, 1H).

LC/MS, m/z=526.2 [M+H]$^+$ (Calc: 525.6).

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-1H-indole-3-carboxamide (Compound 123)

LC/MS, m/z=540.2 [M+H]$^+$ (Calc: 539.7).

Example 3

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-4-methylbenzenesulfonamide (Compound 124)

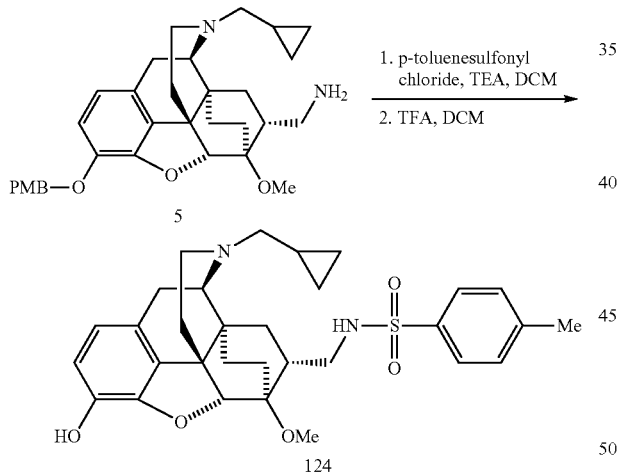

To a solution of Compound 5 (31 mg, 0.06 mmol, 1 eq) in DCM (2 mL) at 0° C. was added triethylamine (86 µL, 6.0 mmol, 10 eq.) followed by p-toluenesulfonyl chloride (34.3 mg, 0.18 mmol, 3 eq.). The reaction mixture was stirred at RT for 16 h. The reaction mixture was diluted with DCM and washed with saturated sodium bicarbonate solution. The organic layer was washed with brine and dried over anhydrous Na$_2$SO$_4$. The solvent was evaporated and the crude material dissolved in DCM (2 mL), TFA (0.5 mL) was added and the mixture stirred at 0° C. for 1 h. The residue, after evaporating the solvent, was purified by flash chromatography (SiO$_2$, 1-5% MeOH (with 7% ammonia)/DCM) to provide Compound 124 as the free base. The free base was dissolved in DCM (1 mL) and 1M HCl in Et$_2$O (1 mL) was added and the mixture stirred at 0° C. for 1 h. The solvents were evaporated and the residue was triturated with Et$_2$O to give Compound 124 HCl salt as a white solid LC/MS, m/z=551.2 [M+H]$^+$ (Calc: 550.7).

In a similar manner the following compounds were prepared.

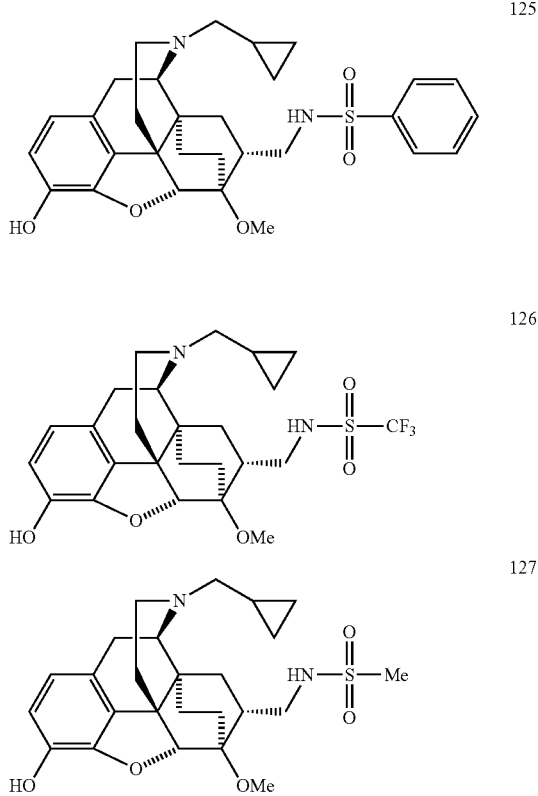

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-benzenesulfonamide (Compound 125)

LC/MS, m/z=537.2 [M+H]$^+$ (Calc: 536.7).

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-1,1,1-trifluoromethanesulfonamide (Compound 126)

LC/MS, m/z=529.2 [M+H]$^+$ (Calc: 528.6)

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)methanesulfonamide (Compound 127)

LC/MS, m/z=475.2 [M+H]$^+$ (Calc: 474.6)

Example 4

The following compounds were prepared in a manner similar to that described in Example 2

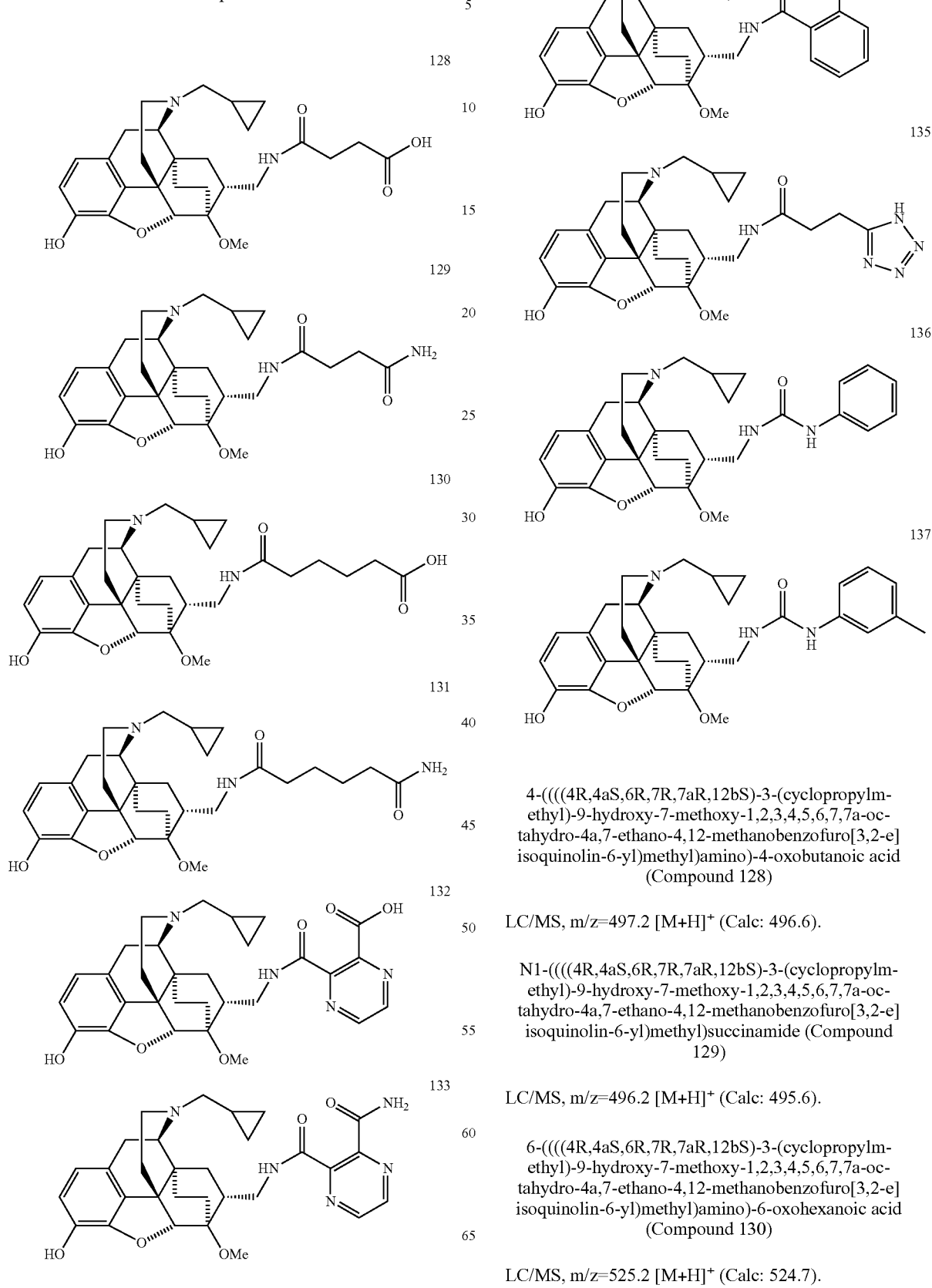

4-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)amino)-4-oxobutanoic acid (Compound 128)

LC/MS, m/z=497.2 [M+H]$^+$ (Calc: 496.6).

N1-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)succinamide (Compound 129)

LC/MS, m/z=496.2 [M+H]$^+$ (Calc: 495.6).

6-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)amino)-6-oxohexanoic acid (Compound 130)

LC/MS, m/z=525.2 [M+H]$^+$ (Calc: 524.7).

N1-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)adipamide (Compound 131)

LC/MS, m/z=524.3 [M+H]⁺ (Calc: 523.7).

3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)carbamoyl)pyrazine-2-carboxylic acid (Compound 132)

LC/MS, m/z=547.2 [M+H]⁺ (Calc: 546.6).

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)pyrazine-2,3-dicarboxamide (Compound 133)

LC/MS, m/z=546.2 [M+H]⁺ (Calc: 545.6).

2-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)carbamoyl)benzoic acid (Compound 134)

LC/MS, m/z=545.2 [M+H]⁺ (Calc: 544.6).

N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(1H-tetrazol-5-yl)propanamide (Compound 135)

LC/MS, m/z=521.2 [M+H]⁺ (Calc: 520.6).

1-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-phenylurea (Compound 136)

LC/MS, m/z=516.2 [M+H]⁺ (Calc: 515.6).

1-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-3-(m-tolyl)urea (Compound 137)

LC/MS, m/z=530.3 [M+H]⁺ (Calc: 529.7).

The foregoing description of the various aspects and embodiments of the present invention has been presented for purposes of illustration and description. It is not intended to be exhaustive or all embodiments or to limit the invention to the specific aspects disclosed. Obvious modifications or variations are possible in light of the above teachings and such modifications and variations may well fall within the scope of the invention as determined by the appended claims when interpreted in accordance with the breadth to which they are fairly, legally and equitably entitled.

What is claimed is:
1. A compound of Formula I:

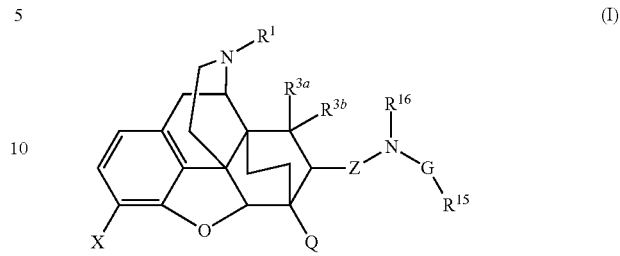

wherein
G is selected from carbonyl C(=O), sulfonyl S(=O)$_2$, or sulfinyl S(=O);
Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$) alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$)$_s$—OH, —O(C=O)R$^9$, —O—(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl -C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ or R$^{14}$; any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;
X is selected from OH, hydroxy(C$_1$-C$_6$)alkyl-, dihydroxy(C$_1$-C$_6$)alkyl-, halogen, —NH$_2$, —NR$^{20}$(C=O)R$^{12}$, —CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O(C$_1$-C$_6$)alkyl, —(OCH$_2$CH$_2$)$_s$—OH, —(CH$_2$)$_p$CHOHCH$_2$OH, CN, —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl,((5- to 12-membered)aryl)-(C$_1$-C$_6$)alkyl-, ((5- to 12-membered)aryl) -(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle,((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, or ((7- to 12-membered)bicycloheterocycle)-(C$_1$-C$_6$)alkoxy-;
any of which may optionally be substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl;

Z is $-(CH_2)_m-$, optionally substituted with 1 or 2 $-(C_1-C_6)$alkyl;

m is an integer 1, 2, 3, 4, 5, or 6;

p is an integer 0, 1 or 2;

s is an integer 1, 2, 3, 4, 5, 6, 7, 8, 9, 10, 11, 12, or 13;

$R^1$ is selected from hydrogen, $-(C_1-C_{10})$alkyl, $-(C_2-C_{12})$alkenyl, $-(C_2-C_{12})$alkynyl, $-(C_1-C_{10})$alkoxy, $-(C_3-C_{12})$cycloalkyl, $-(C_4-C_{12})$cycloalkenyl, $((C_3-C_{12})$cycloalkyl)-$(C_1-C_6)$alkyl-, $((C_4-C_{12})$cycloalkenyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, phenyl, and benzyl; any of which is optionally substituted with 1, 2, or 3 substituents independently selected from the group consisting of $-(C_1-C_6)$alkyl, OH, halo, $-C(halo)_3$, $-CH(halo)_2$, $-CH_2(halo)$, $-(C_1-C_6)$alkyl-$COOR^7$, $-COOR^7$, $NH_2$, $-NH(C_1-C_6)$alkyl, $-NR^9R^{10}$, $-CN$, $-OR^4$, $-CONR^9R^{10}$, $-NR^9COR^{10}$, $-SR^{11}$, -(3- to 12-membered)carbocyclic ring, -(5- to 12-membered)heterocycle, phenyl, and benzyl;

$R^{3a}$ and $R^{3b}$ are each independently selected from hydrogen, $-(C_1-C_{10})$alkyl, $-(C_2-C_{10})$alkenyl, $-(C_2-C_{10})$alkynyl, $-(C_1-C_{10})$alkoxy, OH, hydroxy$(C_1-C_6)$alkyl-, $-C(halo)_3$, $-CH(halo)_2$, $-CH_2(halo)$, $-(C_1-C_6)$alkyl-C(=O)-$(C_1-C_6)$alkoxy, $-(C_1-C_6)$alkoxy-C(=O)-$(C_1-C_6)$alkyl, $-(C_1-C_6)$alkyl-CN, $-(C_1-C_6)$alkyl-$COOR^7$, $-(C_1-C_6)$alkoxy-$COOR^7$, $-(C_3-C_{12})$cycloalkyl, $((C_3-C_{12})$cycloalkyl)-$(C_1-C_6)$alkyl-, $((C_3-C_{12})$cycloalkyl)-$(C_1-C_6)$alkoxy-, $((C_3-C_{12})$cycloalkyl)-$(C_1-C_6)$alkoxy-$(C_1-C_6)$alkyl-, $-(C_4-C_{12})$cycloalkenyl, $((C_4-C_{12})$cycloalkenyl)-$(C_1-C_6)$alkyl-, $((C_4-C_{12})$cycloalkenyl)-$(C_1-C_6)$alkoxy-, $((C_4-C_{12})$cycloalkenyl)-$(C_1-C_6)$alkoxy-$(C_1-C_6)$alkyl-, -(5- to 12-membered)aryl, ((5- to 12-membered)aryl)-$(C_1-C_6)$alkyl-, ((5- to 12-membered)aryl)-$(C_1-C_6)$alkoxy-, ((5- to 12-membered)aryl)-$(C_1-C_6)$alkoxy-$(C_1-C_6)$alkyl-, -(5- to 12-membered)heteroaryl, ((5- to 12-membered)heteroaryl)-$(C_1-C_6)$alkyl-, ((5- to 12-membered)heteroaryl)-$(C_1-C_6)$alkoxy-, ((5- to 12-membered)heteroaryl)-$(C_1-C_6)$alkoxy-$(C_1-C_6)$alkyl-, -(3- to 12-membered)heterocycle, ((3- to 12 membered)heterocycle)-$(C_1-C_6)$alkyl-, ((3- to 12 membered)heterocycle)-$(C_1-C_6)$alkoxy-, ((3- to 12 membered)heterocycle)-$(C_1-C_6)$alkoxy-$(C_1-C_6)$alkyl-, or together form (=O);

$R^4$ is selected from $-(C_1-C_6)$alkyl, $-(C_2-C_6)$alkenyl, $-(C_2-C_6)$alkynyl, $-C(halo)_3$, $-CH(halo)_2$, $-CH_2(halo)$, hydroxy$(C_1-C_6)$alkyl-, $-(C_3-C_{12})$cycloalkyl, $((C_3-C_{12})$cycloalkyl)-$(C_1-C_6)$alkyl-, $-(C_6-C_{14})$bicycloalkyl, $((C_6-C_{14})$bicycloalkyl)-$(C_1-C_6)$alkyl-, $-(C_8-C_{20})$tricycloalkyl, $((C_8-C_{20})$tricycloalkyl)-$(C_1-C_6)$alkyl-, $-(C_4-C_{12})$cycloalkenyl, $((C_4-C_{12})$cycloalkenyl)-$(C_1-C_6)$alkyl-, $-(C_7-C_{14})$bicycloalkenyl, $((C_7-C_{14})$bicycloalkenyl)-$(C_1-C_6)$alkyl-, $-(C_8-C_{20})$tricycloalkenyl, $((C_8-C_{20})$tricycloalkenyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, or ((7- to 12-membered)bicycloheterocycle)-$(C_1-C_6)$alkyl-;

$R^5$ and $R^6$ are each independently hydrogen, $-(C_1-C_6)$alkyl, $-(C_3-C_8)$cycloalkyl, $((C_3-C_8)$cycloalkyl)-$(C_1-C_6)$alkyl-, $-COOR^7$, $-(C_1-C_6)$alkyl-CO-$OR^7$, $-CONH_2$, or $(C_1-C_6)$alkyl-$CONH-$, or $R^5$ and $R^6$ together with the nitrogen atom to which they are attached form a (4- to 8-membered)heterocycle; any of which is optionally substituted with 1 or 2 substituents independently selected from the group consisting of $-(C_1-C_6)$alkyl, OH, halo, $-C(halo)_3$, $-CH(halo)_2$, $-CH_2(halo)$, $-(C_1-C_6)$alkyl-$COOR^7$, $-COOR^7$, $NH_2$, $-NH(C_1-C_6)$alkyl, $-NR^9R^{10}$, $-CN$, $-OR^4$, $-CONR^9R^{10}$, $-NR^9COR^{10}$, $-SR^{11}$, -(3- to 12-membered)carbocyclic ring, -(5- to 12-membered)heterocycle, phenyl, and benzyl;

$R^7$ is selected from hydrogen, $-(C_1-C_6)$alkyl, $-(C_2-C_6)$alkenyl, $-(C_2-C_6)$alkynyl, $-(C_3-C_{12})$cycloalkyl, $-(C_4-C_{12})$cycloalkenyl, $((C_3-C_{12})$cycloalkyl)-$(C_1-C_6)$alkyl-, or $((C_4-C_{12})$cycloalkenyl)-$(C_1-C_6)$alkyl-;

$R^9$ and $R^{10}$ are each independently selected from hydrogen, $-(C_1-C_6)$alkyl, $-(C_2-C_6)$alkenyl, $-(C_2-C_6)$alkynyl, $-(C_1-C_{10})$alkoxy, $-(C_3-C_{12})$cycloalkyl, $-(C_3-C_{12})$cycloalkenyl, $((C_3-C_{12})$cycloalkyl)-$(C_1-C_6)$alkyl-, $((C_3-C_{12})$cycloalkenyl)-$(C_1-C_6)$alkyl-;

each $R^{11}$ is independently selected from hydrogen, $-(C_1-C_{10})$alkyl, $-(C_2-C_{10})$alkenyl, $-(C_2-C_{10})$alkynyl, $-(C_1-C_{10})$alkoxy, $((C_1-C_6)$alkyl)sulfonyl$(C_1-C_6)$alkyl-, $-(C_3-C_{12})$cycloalkyl, $((C_3-C_{12})$cycloalkyl)-$(C_1-C_6)$alkyl-, $-(C_4-C_{12})$cycloalkenyl, or $((C_4-C_{12})$cycloalkenyl)-$(C_1-C_6)$alkyl-;

$R^{12}$ and $R^{13}$ are each independently selected from hydrogen, $-(C_1-C_{10})$alkyl, $-(C_2-C_{12})$alkenyl, $-(C_2-C_{12})$alkynyl, $-(C_1-C_{10})$alkoxy, $-(OCH_2CH_2)_s-O(C_1-C_6)$alkyl, $-(C_3-C_{12})$cycloalkyl, $((C_3-C_{12})$cycloalkyl)-$(C_1-C_6)$alkyl-, $-(C_4-C_{12})$cycloalkenyl, $((C_4-C_{12})$cycloalkenyl)-$(C_1-C_6)$alkyl-, $-(C_6-C_{14})$bicycloalkyl, $((C_6-C_{14})$bicycloalkyl)-$(C_1-C_6)$alkyl-, $-(C_8-C_{20})$tricycloalkyl, $((C_8-C_{20})$tricycloalkyl)-$(C_1-C_6)$alkyl-, $-(C_7-C_{14})$bicycloalkenyl, $((C_7-C_{14})$bicycloalkenyl)-$(C_1-C_6)$alkyl-, $-(C_8-C_{20})$tricycloalkenyl, $((C_8-C_{20})$tricycloalkenyl)-$(C_1-C_6)$alkyl-, -(5- to 12-membered)aryl, ((5- to 12-membered)aryl)$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)hererocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl or naphthyl; each of which is optionally substituted with one or two substituents independently selected from the group consisting of OH, (=O), halo, $-C(halo)_3$, $-CH(halo)_2$, $-CH_2(halo)$, $-(C_1-C_6)$alkyl, halo$(C_1-C_6)$alkyl-, $-(C_2-C_6)$alkenyl, $-(C_2-C_6)$alkynyl, hydroxy$(C_1-C_6)$alkyl-, phenyl, benzyl, $NH_2$, $-NH(C_1-C_6)$alkyl, CN, SH, $OR^4$, $-CONR^5R^6$, $-COOR^7$, $-(C_3-C_{12})$cycloalkyl, $((C_3-C_{12})$cycloalkyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^{14}$ is selected from $-COOR^7$, $-(C_1-C_6)$alkyl-CO-$OR^7$, $-C(=O)-(C_1-C_6)$alkyl-$COOR^7$, $-(C_1-C_6)$alkyl-C(=O)-$(C_1-C_6)$alkyl-$COOR^7$, $-CONH_2$, or $(C_1-C_6)$alkyl-$CONH-$;

$R^{15}$ is selected from $R^{20}$ or $R^{21}$;

$R^{16}$ is hydrogen, —$(C_1$-$C_6)$alkyl, —$(C_3$-$C_{12})$cycloalkyl, $((C_3$-$C_{12})$cycloalkyl)-$(C_1$-$C_6)$alkyl-, (5- to 12-membered)heteroaryl, or ((5- to 12-membered)heteroaryl)-$(C_1$-$C_6)$alkyl-;

$R^{20}$ is selected from hydrogen, —$(C_1$-$C_{10})$alkyl, —$(C_2$-$C_{12})$alkynyl, —$(C_1$-$C_{10})$alkoxy, —$(OCH_2CH_2)_s$—O$(C_1$-$C_6)$alkyl, —$(CH_2CH_2O)_s$—$(C_1$-$C_6)$alkyl, —$NH_2$, —$NH(C_1$-$C_6)$alkyl, CN, —$CONR^5R^6$, —$(C_1$-$C_6)$alkyl-CO—$NR^5R^6$, —$COOR^7$, —$(C_1$-$C_6)$alkyl-CO—$OR^7$, —$(C_1$-$C_6)$alkoxy-$COOR^7$, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered) bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of —OH, (=O), halo, —$C(halo)_3$, —$CH(halo)_2$, —$CH_2(halo)$, —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$alkyl-, —$(C_1$-$C_6)$alkoxy, $((C_1$-$C_6)$alkoxy)CO$(C_1$-$C_6)$alkoxy-, phenyl, benzyl, —$NH_2$, —$NH(C_1$-$C_6)$alkyl, —$(C_1$-$C_6)$alkyl-NH$(C_1$-$C_6)$alkyl-$R^{14}$, —CN, —SH, —$OR^4$, —$CONR^5R^6$, —$(C_1$-$C_6$alkyl)-CO—$NR^5R^6$, —$COOR^7$, —$(C_1$-$C_6)$alkyl-CO—$OR^7$, —$(C_1$-$C_6)$alkoxy-$COOR^7$, —$(OCH_2CH_2)_s$—$O(C_1$-$C_6)$alkyl, —$(CH_2CH_2O)_s$—$(C_1$-$C_6)$alkyl, $((C_1$-$C_6)$alkyl)sulfonyl $(C_1$-$C_6)$alkyl-, —NH—$SO_2(C_1$-$C_6)$alkyl-, —$N(SO_2(C_1$-$C_6)$alkyl$)_2$, —C(=NH)$NH_2$, —NH—CO—$(C_1$-$C_6)$alkyl, —NH—CO—$NH_2$, —NH—C(=O)—NH—$(C_1$-$C_6)$alkyl, —NH—C(=O)-(5- to 12-membered)aryl, —NH—C(=O)—$(C_1$-$C_6)$alkyl-(5- to 12-membered)aryl, —NH—$(C_1$-$C_6)$alkyl-CO—$OR^7$, —NH—C(=O)—$(C_1$-$C_6)$alkyl-CO—$OR^7$, —NH—C(=O)—CH($NH_2$)—$(C_1$-$C_6)$alkyl-CO—$OR^7$, —$(C_3$-$C_{12})$cycloalkyl, $((C_3$-$C_{12})$cycloalkyl)-$(C_1$-$C_6)$alkyl-, -(5- to 12-membered)aryl, -(5- to 12-membered)aryloxy, —$(C_1$-$C_6)$alkoxyC(O)$NR^5R^6$, —NH—$(C_1$-$C_6)$alkylC(O)—$NR^5R^6$, —C(O)NH—$(C_1$-$C_6)$alkyl-$COOR^7$, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{21}$ is selected from $R^{20}$ or an alpha-amino compound of structure:

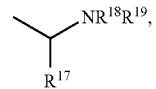

wherein
each $R^{17}$ is independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, OH, hydroxy$(C_1$-$C_6)$alkyl-, —$C(halo)_3$, —$CH(halo)_2$, —$CH_2(halo)$, —$(C_1$-$C_6)$alkyl-C(=O)—$(C_1$-$C_6)$alkoxy, —$(C_1$-$C_6)$alkoxy-C(=O)—$(C_1$-$C_6)$alkyl, —$(C_1$-$C_6)$alkyl-CN, —$(C_1$-$C_6)$alkyl-$COOR^7$, —$(C_1$-$C_6)$alkyl-CN, —$(C_1$-$C_6)$alkyl-CON $R^9R^{10}$, —$(C_1$-$C_6)$alkoxy-$COOR^7$, —$(C_3$-$C_{12})$cycloalkyl, $((C_3$-$C_{12})$cycloalkyl)-$(C_1$-$C_6)$alkyl-, $((C_3$-$C_{12})$cycloalkyl)-$(C_1$-$C_6)$alkoxy-, $((C_3$-$C_{12})$cycloalkyl)-$(C_1$-$C_6)$alkoxy-$(C_1$-$C_6)$alkyl-, —$(C_4$-$C_{12})$cycloalkenyl, $((C_4$-$C_{12})$cycloalkenyl)-$(C_1$-$C_6)$alkyl-, $((C_4$-$C_{12})$cycloalkenyl)-$(C_1$-$C_6)$alkoxy-, $((C_4$-$C_{12})$cycloalkenyl)-$(C_1$-$C_6)$alkoxy-$(C_1$-$C_6)$alkyl-, -(5- to 12-membered)aryl, ((5- to 12-membered)aryl)-$(C_1$-$C_6)$alkyl-, ((5- to 12-membered)aryl)-$(C_1$-$C_6)$alkoxy-, ((5- to 12-membered)aryl)-$(C_1$-$C_6)$alkoxy-$(C_1$-$C_6)$alkyl-, -(5- to 12-membered)heteroaryl, ((5- to 12-membered)heteroaryl)-$(C_1$-$C_6)$alkyl-, ((5- to 12-membered)heteroaryl)-$(C_1$-$C_6)$alkoxy-, ((5- to 12-membered)heteroaryl)-$(C_1$-$C_6)$alkoxy-$(C_1$-$C_6)$alkyl-, -(3- to 12-membered)heterocycle, ((3- to 12 membered)heterocycle)-$(C_1$-$C_6)$alkyl-, ((3- to 12 membered)heterocycle)-$(C_1$-$C_6)$alkoxy-, ((3- to 12 membered)heterocycle)-$(C_1$-$C_6)$alkoxy-$(C_1$-$C_6)$alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —$(C_1$-$C_6)$alkyl, OH, halo, —$C(halo)_3$, —$CH(halo)_2$, —$CH_2(halo)$, —$(C_1$-$C_6)$alkyl-$COOR^7$, —$COOR^7$, $NH_2$, —$NH(C_1$-$C_6)$alkyl, —$NR^9R^{10}$, —CN, —$OR^4$, —$CONR^9R^{10}$, —$NR^9COR^{10}$, —$SR^{11}$, -(3- to 12-membered)carbocyclic ring, -(5- to 12-membered)heterocycle, phenyl, and benzyl; and $R^{18}$ and $R^{19}$ are each independently selected from hydrogen, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_3$-$C_{12})$cycloalkenyl, $((C_3$-$C_{12})$cycloalkyl)-$(C_1$-$C_6)$alkyl-, $((C_3$-$C_{12})$cycloalkenyl)-$(C_1$-$C_6)$alkyl-, —C(=O)—$(C_1$-$C_6)$alkyl; any of which is optionally substituted with 1 or 2 substituents independently selected from the group consisting of —$(C_1$-$C_6)$alkyl, OH, halo, —$C(halo)_3$, —$CH(halo)_2$, —$CH_2(halo)$, —$(C_1$-$C_6)$alkyl-$COOR^7$, —$COOR^7$, $NH_2$, —$NH(C_1$-$C_6)$alkyl, —$NR^9R^{10}$, —CN, —$OR^4$, —$CONR^9R^{10}$, —$NR^9COR^{10}$, —$SR^{11}$, -(3- to 12-membered)carbocyclic ring, -(5- to 12-membered)heterocycle, phenyl, and benzyl; or $R^{19}$ may optionally be a peptide-forming moiety having the structure

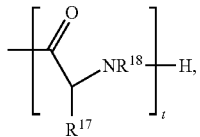

where t is an integer 1, 2 or 3;
provided that when $R^1$ is cyclopropylmethyl, G is C=O, Q and X are both —$OCH_3$, Z is —$CH_2$—, $R^{15}$ is —$C(NH_2)$ $CH_3$, and $R^{16}$ is hydrogen, then either:
a) at least one of $R^{3a}$ and $R^{3b}$ is a substituent other than hydrogen; or
b) at least one of $R^{18}$ and $R^{19}$ is a substituent other than hydrogen;
or a pharmaceutically acceptable salt or solvate thereof.

2. The compound of claim 1 having the general formula IA:

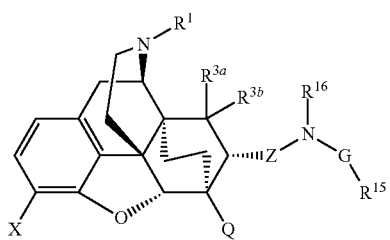

or a pharmaceutically acceptable salt or solvate thereof.

3. The compound of claim 1 wherein Q is selected from —OH or $OCH_3$.

4. The compound of claim 1 wherein X is —OH or —$OCH_3$.

5. The compound of claim 1 wherein m is an integer 1, 2 or 3.

6. The compound of claim 5 wherein Z is unsubstituted.

7. The compound of claim 1 wherein $R^1$ is selected from hydrogen, methyl, cyclopropylmethyl, —$CH_2CH=CH_2$, —$CH_2CH_2C(O)NH_2$, $CH_2CH_2C(O)OH$, $CH_2C(O)OH$, $CH_2C(O)NH_2$, or —$CH_2$-tetrazolyl.

8. The compound of claim 1 wherein $R^{3a}$ and $R^{3b}$ are each hydrogen.

9. The compound of claim 1 wherein $R^{16}$ is hydrogen.

10. The compound of claim 1 wherein $R^{15}$ is $R^{20}$ selected from —$(C_1$-$C_{10})$alkyl, —$(C_2$-$C_{12})$alkynyl, —$NH_2$, —NH $(C_1$-$C_6)$alkyl, —$CONR^5R^6$, —$(C_1$-$C_6)$alkyl-CO—$NR^5R^6$, —$(C_1$-$C_6)$alkyl-CO—$OR^7$, —$(C_3$-$C_{12})$cycloalkyl, $((C_3$-$C_{12})$cycloalkyl)-$(C_1$-$C_6)$alkyl-, -(5- to 12-membered)aryl, ((5- to 12-membered)aryl)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, phenyl, benzyl or naphthyl; each of which is optionally substituted with 1 or 2 substituents independently selected from the group consisting of —$(C_1$-$C_6)$alkyl, OH, halo, —$C(halo)_3$, —$CH(halo)_2$, —$CH_2(halo)$, —$(C_1$-$C_6)$alkyl-$COOR^7$, —$COOR^7$, $NH_2$, —$NH(C_1$-$C_6)$alkyl, —$NR^9R^{10}$, —CN, —$CONR^9R^{10}$, —$NR^9COR^{10}$, —$SR^{11}$, -(3- to 12-membered)carbocyclic ring, -(5- to 12-membered)heterocycle, phenyl, and benzyl.

11. The compound of claim 1 wherein $R^{15}$ is $R^{21}$, and $R^{17}$ is selected from hydrogen, —$(C_1$-$C_6)$alkyl, hydroxy$(C_1$-$C_6)$alkyl-, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —$(C_1$-$C_6)$alkyl, OH, $NH_2$, —$SR^{11}$, or —$CONR^9R^{10}$.

12. The compound of claim 11 wherein $R^{18}$ and $R^{19}$ are each independently selected from hydrogen, —$(C_1$-$C_6)$alkyl, or —C(=O)—$(C_1$-$C_6)$alkyl.

13. A compound having the general formula II:

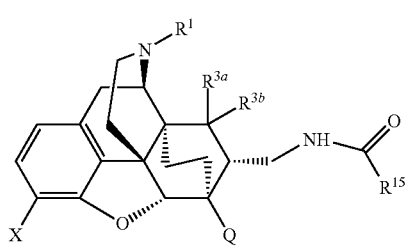

wherein
Q and X are OH or —$(C_1$-$C_6)$alkoxy;
$R^1$ is selected from hydrogen, —$(C_1$-$C_6)$alkyl, —$(C_3$-$C_6)$ cycloalkyl, and $((C_3$-$C_6)$cycloalkyl)-$(C_1$-$C_6)$alkyl;
$R^{15}$ is selected from an alpha-amino compound of structure:

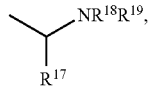

wherein
wherein each $R^{17}$ is independently selected from hydrogen, —$(C_1$-$C_{10})$alkyl, —$(C_2$-$C_{10})$alkenyl, —$(C_2$-$C_{10})$ alkynyl, —$(C_1$-$C_{10})$alkoxy, OH, hydroxy$(C_1$-$C_6)$alkyl-, —$C(halo)_3$, —$CH(halo)_2$, —$CH_2(halo)$, —$(C_1$-$C_6)$ alkyl-C(=O)—$(C_1$-$C_6)$alkoxy, —$(C_1$-$C_6)$alkoxy-C(=O)—$(C_1$-$C_6)$alkyl, —$(C_1$-$C_6)$alkyl-CN, —$(C_1$-$C_6)$ alkyl-$COOR^7$, —$(C_1$-$C_6)$alkyl-CN, —$(C_1$-$C_6)$alkyl-CON $R^9R^{10}$, —$(C_1$-$C_6)$alkoxy-$COOR^7$, —$(C_3$-$C_{12})$ cycloalkyl, $((C_3$-$C_{12})$cycloalkyl)-$(C_1$-$C_6)$alkyl-, $((C_3$-$C_{12})$cycloalkyl)-$(C_1$-$C_6)$alkoxy-, $((C_3$-$C_{12})$cycloalkyl)-$(C_1$-$C_6)$alkoxy-$(C_1$-$C_6)$alkyl-, —$(C_4$-$C_{12})$cycloalkenyl, $((C_4$-$C_{12})$cycloalkenyl)-$(C_1$-$C_6)$alkyl-,$((C_4$-$C_{12})$cycloalkenyl)-$(C_1$-$C_6)$alkoxy-, $((C_4$-$C_{12})$cycloalkenyl)-$(C_1$-$C_6)$alkoxy-$(C_1$-$C_6)$alkyl-, -(5- to 12-membered) aryl, ((5- to 12-membered)aryl)-$(C_1$-$C_6)$alkyl-, ((5- to 12-membered)aryl)-$(C_1$-$C_6)$alkoxy-, ((5- to 12-membered)aryl)-$(C_1$-$C_6)$alkoxy-$(C_1$-$C_6)$alkyl-, -(5- to 12-membered)heteroaryl, ((5- to 12-membered)heteroaryl)-$(C_1$-$C_6)$alkyl-, ((5- to 12-membered)heteroaryl)-$(C_1$-$C_6)$alkoxy-, ((5- to 12-membered)heteroaryl)-$(C_1$-$C_6)$alkoxy-$(C_1$-$C_6)$alkyl-, -(3- to 12-membered)heterocycle, ((3- to 12 membered)heterocycle)-$(C_1$-$C_6)$alkyl-, ((3- to 12 membered)heterocycle)-$(C_1$-$C_6)$alkoxy-, ((3- to 12 membered)heterocycle)-($C_1$-$C_6$)alkoxy-($C_1$-$C_6$)alkyl-; or $R^{17}$ together with $R^{18}$ or $R^{19}$ and the N to which they are attached may form a 3- to 12-membered heterocycle; any of which is optionally substituted with 1 or 2 substituents independently selected from the group consisting of —($C_1$-$C_6$) alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —OR$^4$, —CONR$^9$R$^{10}$, —NR$^9$COR$^{10}$, —SR$^{11}$, -(3- to 12-membered)carbocyclic ring, -(5- to 12-membered)heterocycle, phenyl, and benzyl; and wherein R$^{18}$ and R$^{19}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, —C(=O)—($C_1$-$C_6$)alkyl; or R$^{19}$ may optionally be a peptide-forming moiety having the structure

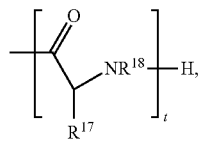

where t is an integer 1 or 2;
provided that when R$^1$ is cyclopropylmethyl, Q and X are both —OCH$_3$, and R$^{15}$ is —C(NH$_2$)CH$_3$, then either:
a) at least one of R$^{3a}$ and R$^{3b}$ is a substituent other than hydrogen; or
b) at least one of R$^{18}$ and R$^{19}$ is a substituent other than hydrogen;
or a pharmaceutically acceptable salt or solvate thereof.

14. A compound having the general formula III:

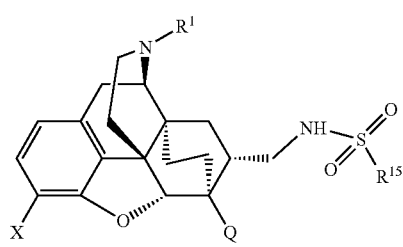

(III)

wherein
Q and X are OH or —($C_1$-$C_6$)alkoxy;
R$^1$ is selected from hydrogen, —($C_1$-$C_6$)alkyl, —($C_3$-$C_6$)cycloalkyl, and (($C_3$-$C_6$)cycloalkyl)-($C_1$-$C_6$)alkyl;
R$^{15}$ is R$^{20}$ selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —CN, —SH, —OR$^4$, —CONR$^5$R$^6$, —($C_1$-$C_6$alkyl)-CO —NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl ($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO —OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;
or a pharmaceutically acceptable salt or solvate thereof.

15. A compound of claim 1 selected from the group consisting of:
N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-4-methylbenzenesulfonamide;
N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-benzenesulfonamide;
N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)-1,1,1-trifluoromethanesulfonamide;
N-(((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl)methanesulfonamide;
(S)-2-amino-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)propanamide;
S-2-amino-N-(((4R,4aS,6R,7R,7aR,12bS)-3-cyclopropylmethyl)-9-hydroxy-7-methoxy-1,2,3,4,5,6,7,7a-octahydro-4a,7-ethano-4,12-methanobenzofuro[3,2-e]
isoquinolin-6-yl)-methyl)-3-phenylpropanamide;
(2S,3S)-2-amino-N-(((4R,4aS,6R,7a,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl-3-methylpentanamide;
(S)-2-amino-N-(((4R,4aS,6R,7R,7aR,12bS)-3-(cyclopro-
pylmethyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)propanamide;
(S)-2-amino-N-(((4R,4aS,6R,7R,7aR,12bS)-3-(cyclopro-
pylmethyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)-3-hydroxypropanamide;
(S)-2-amino-N-(((4R,4aS,6R,7R,7aR,12bS)-3-(cyclopro-
pylmethyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)-4-methylpentanamide;
(S)—N-(((4R,4aS,6R,7R,7aR,12bS)-3-(cyclopropylm-
ethyl)-9-hydroxy-7-methoxy-1,2,3,4,5,6,7,7a-octahy-
dro-4a,7-ethano-4,12-methanobenzofuro[3,2-e]iso-
quinolin-6-yl)methyl)pyrrolidine-2-carboxamide;
(S)-2-amino-N-(((4R,4aS,6R,7R,7aR,12bS)-3-(cyclopro-
pylmethyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)-3-(4-hydroxyphenyl)
propanamide;
(S)-3-amino-N-(((4R,4aS,6R,7R,7aR,12bS)-3-(cyclopro-
pylmethyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)amino)-4-oxobutanoic acid;
(S)-2-amino-N-(((4R,4aS,6R,7R,7aR,12bS)-3-(cyclopro-
pylmethyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)-3-(1H-imidazol-4-yl)
propanamide;
(S)-2-acetamido-N-(((4R,4aS,6R,7R,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl)propanamide;
(S)-2-acetamido-N-(((4R,4aS,6R,7R,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl)-3-phenylpropanamide;
2-amino-N-(((4R,4aS,6R,7R,7aR,12bS)-3-(cyclopropyl-
methyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)acetamide;
(S)-2-acetamido-N-(((4R,4aS,6R,7R,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl)-3-(4-hydroxyphenyl)
propanamide;
(2S,3S)-2-acetamido-N-(((4R,4aS,6R,7a,7aR,12bS)-3-
(cyclopropylmethyl)-9-hydroxy-7-methoxy-1,2,3,4,5,
6,7,7a-octahydro-4a,7-ethano-4,12-methanobenzofuro
[3,2-e]isoquinolin-6-yl)methyl)-3-methylpentanamide;
(S)-1-acetyl-N-(((4R,4aS,6R,7a,7aR,12bS)-3-(cyclopro-
pylmethyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)pyrrolidine-2-carboxamide;
(S)-2-acetamido-N-(((4R,4aS,6R,7R,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl)-3-(1H-imidazol-4-yl)
propanamide;
2-acetamido-N-(((4R,4aS,6R,7R,7aR,12bS)-3-(cyclopro-
pylmethyl)-9-hydroxy-7-methoxy-1,2,3,4,5,6,7,7a-oc-
tahydro-4a,7-ethano-4,12-methanobenzofuro[3,2-e]
isoquinolin-6-yl)methyl)acetamide;
(S)-3-acetamido-4-(((4a,4R,4aS,6R,7R,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl)amino)-4-oxobutanoic
acid;
(S)-2-acetamido-N$^1$-(((4R,4aS,6R,7R,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl)succinamide;
(S)-2-acetamido-N-(((4R,4aS,6R,7R,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl)-4-methylpentanamide;
(S)-2-amino-N$^1$-(((4R,4aS,6R,7R,7aR,12bS)-3-(cyclo-
propylmethyl)-9-hydroxy-7-methoxy-1,2,3,4,5,6,7,7a-
octahydro-4a,7-ethano-4,12-methanobenzofuro[3,2-e]
isoquinolin-6-yl)methyl)succinamide:
(S)-2-acetamido-N-(((4R,4aS,6R,7R,7aR,12bS)-3-(cy-
clopropylmethyl)-9-hydroxy-7-methoxy-1,2,3,4,5,6,7,
7a-octahydro-4a,7-ethano-4,12-methanobenzofuro[3,
2-e]isoquinolin-6-yl)methyl)-3-hydroxypropanamide;
and
N-(((4R,4aS,6R,7R,7aR,12bS)-3-(cyclopropylmethyl)-9-
hydroxy-7-methoxy-1,2,3,4,5,6,7,7a-octahydro-4a,7-
ethano-4,12-methanobenzofuro[3,2-e]isoquinolin-6-
yl)methyl)-1H-indole-3-carboxamide;
and a pharmaceutically acceptable salt or solvate thereof.

16. A pharmaceutical composition comprising an effective amount of a compound of claim 1, and a pharmaceutically acceptable carrier or excipient.

17. A method for modulating opioid receptor function in a cell, comprising contacting a cell capable of expressing an opioid receptor with an effective amount of a compound of claim 1 or a pharmaceutically acceptable salt or solvate thereof.

18. A method of treating a condition in a mammal comprising administering to such mammal in need thereof an effective amount of a compound of claim 1 or a pharmaceutically acceptable salt or solvate thereof, wherein said condition is selected from the group consisting of pain, alcohol withdrawal, drug withdrawal, addictive disorders, pruritis, constipation, and diarrhea.

19. The method of claim 18 wherein the condition is pain.

20. The method of claim 18 wherein the condition is constipation.

* * * * *